(12) United States Patent
Barrall et al.

(10) Patent No.: US 10,228,347 B2
(45) Date of Patent: Mar. 12, 2019

(54) HIGH CONTRAST SIGNAL TO NOISE RATIO DEVICE COMPONENTS

(75) Inventors: Geoffrey A. Barrall, San Diego, CA (US); Eric N. Ervin, Salt Lake City, UT (US); Prithwish Pal, San Diego, CA (US)

(73) Assignee: Electronic BioSciences, Inc., San Diego, CA (US)

( * ) Notice: Subject to any disclaimer, the term of this patent is extended or adjusted under 35 U.S.C. 154(b) by 620 days.

(21) Appl. No.: 14/128,587

(22) PCT Filed: Jun. 22, 2012

(86) PCT No.: PCT/US2012/043859
§ 371 (c)(1),
(2), (4) Date: Apr. 4, 2014

(87) PCT Pub. No.: WO2012/178093
PCT Pub. Date: Dec. 27, 2012

(65) Prior Publication Data
US 2014/0216933 A1 Aug. 7, 2014

Related U.S. Application Data

(60) Provisional application No. 61/621,378, filed on Apr. 6, 2012, provisional application No. 61/513,439, filed on Jul. 29, 2011, provisional application No. 61/500,971, filed on Jun. 24, 2011.

(51) Int. Cl.
*G01N 27/447* (2006.01)
*G01N 33/487* (2006.01)

(52) U.S. Cl.
CPC ..... *G01N 27/447* (2013.01); *G01N 33/48721* (2013.01)

(58) Field of Classification Search
None
See application file for complete search history.

(56) References Cited

U.S. PATENT DOCUMENTS

| | | | |
|---|---|---|---|
| 6,936,433 | B2 | 8/2005 | Akeson et al. |
| 7,608,276 | B2 | 10/2009 | Masignani et al. |
| 7,731,826 | B2 | 6/2010 | Hibbs et al. |
| 7,777,505 | B2 | 8/2010 | White et al. |
| 8,124,191 | B2 | 2/2012 | Ervin et al. |
| 8,324,914 | B2 | 12/2012 | Chen |
| 8,962,242 | B2 | 2/2015 | Chen |
| 2004/0191845 | A1 | 9/2004 | Bayley |
| 2007/0281329 | A1 | 12/2007 | Akeson et al. |
| 2009/0136958 | A1 | 5/2009 | Gershow |
| 2009/0167288 | A1 | 7/2009 | Reid et al. |
| 2009/0222216 | A1 | 9/2009 | Hibbs et al. |
| 2010/0035260 | A1 | 2/2010 | Olasagasti |
| 2010/0203024 | A1 | 8/2010 | Terman et al. |
| 2012/0255862 | A1 | 10/2012 | Dunnam et al. |
| 2014/0248608 | A1 | 9/2014 | Barrall et al. |
| 2015/0329600 | A1 | 11/2015 | Barrall et al. |

FOREIGN PATENT DOCUMENTS

| | | |
|---|---|---|
| WO | WO 08/102120 | 8/2008 |
| WO | WO 09/077734 | 6/2009 |
| WO | WO 10/034018 | 3/2010 |
| WO | WO 2010/055307 | 5/2010 |
| WO | WO 2010/081875 | 7/2010 |
| WO | WO 12/178093 | 12/2012 |
| WO | WO 12/178097 | 12/2012 |
| WO | WO 14/100481 | 6/2014 |

OTHER PUBLICATIONS

Maglia et al. PNAS, 105(50), pp. 19720-19725, 2008.*
Chu et al., "Real-Time Monitoring of DNA Polymerase Function and Stepwise Single-Nucleotide DNA Strand Translocation through a Protein Nanopore" Angewandte Chemie (Int. Ed. in English) (2010) 122(52):10304-10307.
Ervin et al., "Mapping the Sensing Zone of Alpha-Hemolysin Using Immobilized DNA Containing a Single Abasic Residue" Biophysical Journal (2011) 100(3):167a.
Li-Qun et al., "Reversal of charge selectivity in transmembrane protein pores by using noncovalent molecular adapters" PNAS USA (2000) 97(8):3959-3964.
Smeets et al., "Noise in solid-state nanopores" PNAS USA (2008) 105(2):417-421.
Extended European Search Report dated Nov. 4, 2014 in EP Application No. 12802702.6, filed on Jun. 22, 2012 and published as EP 2 724 148 on Apr. 30, 2014.
Extended European Search Report dated Nov. 4, 2014 in EP Application No. 12802737.2, filed on Jun. 22, 2012 and published as EP 2 724 150 on Apr. 30, 2014.
Barrall et al., "Quartz Nanopore Membranes for Low Noise Measurements of Ion Channel Conductance" Biophysical Journal (2010) 98(3) supp. 1:598a.
Timp et al., "Nanopore Sequencing: Electrical Measurements of the Code of Life" IEEE Transactions on Nanotechnology (2010) 9(3):281-294.
International Search Report and Written Opinion dated Nov. 2, 2012 in International Application No. PCT/US2012/043864, filed on Jun. 22, 2012 and published as WO 2012/178097 on Dec. 27, 2012.
International Preliminary Report on Patentability dated Jan. 9, 2014 in International Application No. PCT/US2012/043864, filed on Jun. 22, 2012 and published as WO 2012/178097 on Dec. 27, 2012.
Ayub and Bayley, "Individual RNA base recognition in immobilized oligonucleotides using a protein nanopore" Nano Lett (2012) 12(11):5637-5643.
Clarke et al., "Continuous base identification for single-molecule nanopore DNA sequencing" Nature Nanotechnology (2009) 4:265-270.
Lathrop et al., "Monitoring the Escape of DNA from a Nanopore Using an Alternating Current Signal" Journal of the American Chemical Society (2010) 132(6):1878-1885.

(Continued)

*Primary Examiner* — Michael L Borin
(74) *Attorney, Agent, or Firm* — Grant IP, Inc.

(57) ABSTRACT

Provided are device components, devices and methods characterized by a high contrast signal to noise ratio (CNR).

30 Claims, 16 Drawing Sheets
Specification includes a Sequence Listing.

(56) References Cited

OTHER PUBLICATIONS

Lubensky et al., "Driven Polymer Translocation Through a Narrow Pore" Biophys. J. (1999) 77(4):1824-1838.
Maglia et al., "Enhanced translocation of single DNA molecules through alpha-hemolysin nanopores by manipulation of internal charge" PNAS USA (2008) 105(50):19720-19725.
Purnell et al., "Nucleotide Identification and Orientation Discrimination of DNA Homopolymers Immobilized in a Protein Nanopore" Nano Letters (2008) 8(9):3029-34.
Sigworth, "Design of the Patch Clamp" Single-channel recording, Sakmann and Neher, eds., pp. 3-35, New York: Plenum Press (1995).
Stoddart et al., "Single-nucleotide discrimination in immobilized DNA oligonucleotides with a biological nanopore" PNAS USA (2009) 106:7702-7707.
Stoddart et al., "Nucleobase recognition in ssDNA at the central constriction of the alpha-hemolysin pore" Nano Lett. (2010) 10(9):3633-3637.
Walker and Bayley, "Key residues for membrane binding, oligomerization, and pore forming activity of staphylococcal alpha-hemolysin identified by cysteine scanning mutagenesis and targeted chemical modification" Journal of Biological Chemistry (1995) 270(39):23065-23071.
Zhang et al., "Bench-Top Method for Fabricating Glass-Sealed Nanodisk Electrodes, Glass Nanopore Electrodes, and Glass Nanopore Membranes of Controlled Size" Anal. Chem. (2007) 79(13):4778-4787.
International Search Report and Written Opinion dated Sep. 21, 2012 in International Application No. PCT/US2012/043859, filed on Jun. 22, 2012 and published as WO 2012/178093 on Dec. 27, 2012.
International Preliminary Report on Patentability dated Jan. 9, 2014 in International Application No. PCT/US2012/043859, filed on Jun. 22, 2012 and published as WO 2012/178093 on Dec. 27, 2012.
International Search Report and Written Opinion dated May 21, 2014 in International Application No. PCT/US2013/076698, filed on Dec. 19, 2013 and published as WO 2014/100481 on Jun. 26, 2014.
International Preliminary Report on Patentability dated on Jul. 5, 2015 in International Application No. PCT/US2013/076698, filed on Dec. 19, 2013 and published as WO 2014/100481 on Jun. 26, 2014.
Office Action dated Nov. 25, 2015 in U.S. Appl. No. 14/128,588, filed May 9, 2014 and published as U.S. 2014-0248608 on Sep. 4, 2014.
Office Action dated May 11, 2017 in U.S. Appl. No. 14/653,246, filed Jun. 17, 2015 and published as U.S. 2015-0329600 on Nov. 19, 2015.
GenBank Accession No. M90536.1, *Staphylococcus aureus* alpha-hemolysin gene, 3' end, Apr. 26, 1993.
Office Action dated Apr. 6, 2018 in U.S. Appl. No. 14/653,246, filed Jun. 17, 2015 and published as U.S. 2015-0329600 on Nov. 19, 2015.
Office Action dated Sep. 27, 2017 in U.S. Appl. No. 14/653,246, filed Jun. 17, 2015 and published as U.S. 2015-0329600 on Nov. 19, 2015.
Kasianowicz et al., "Genetically Engineered Metal Ion Binding Sites on the Outside of a Channel's Transmembrane β-Barral" Biophysical Journal (1999) 76:837-845.

\* cited by examiner

HIGH CONTRAST SIGNAL TO NOISE RATIO DEVICE COMPONENTS

RELATED PATENT APPLICATIONS

This patent application is a national stage application of international patent application no. PCT/US2012/043859, filed on Jun. 22, 2012, entitled HIGH CONTRAST SIGNAL TO NOISE RATIO DEVICE COMPONENTS, naming Geoffrey A. Barrall, Eric N. Ervin, and Prithwish Pal as inventors, which claims the benefit of U.S. provisional patent application No. 61/621,378 filed Apr. 6, 2012, entitled HIGH CONTRAST SIGNAL TO NOISE RATIO NANO-PORES naming Geoffrey Barrall, Eric N. Ervin, and Prithwish Pal as inventors. This patent application also claims the benefit of U.S. provisional patent application No. 61/513,439 filed Jul. 29, 2011, entitled HIGH CONTRAST SIGNAL TO NOISE RATIO NANOPORES naming Geoffrey Barrall, Eric N. Ervin, and Prithwish Pal as inventors. This patent application claims the benefit of U.S. provisional patent application No. 61/500,971 filed Jun. 24, 2011, entitled HIGH CONTRAST SIGNAL TO NOISE RATIO NANOPORES naming Geoffrey Barrall, Eric N. Ervin, Prithwish Pal, as inventors. This patent application is related to U.S. Provisional Patent Application No. 61/513,458 filed on Jul. 29, 2011, entitled METHODS FOR CHARACTERIZING A NANOPORE BASED ON A CONTRAST SIGNAL TO NOISE RATIO naming Geoffrey Barrall, Eric N. Ervin, and Prithwish Pal as inventors. The entire contents of each of the foregoing provisional patent applications is incorporated herein by reference, including all text, tables and drawings.

STATEMENT OF GOVERNMENT SUPPORT

This invention was made with government support under Contract No. 1R01HG005095 awarded by the National Institutes of Health, specifically the National Human Genome Research institute, and Contract No. HSHQDC-09-C-00091 awarded by the Department of Homeland Security. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jul. 27, 2012, is named EBS1003P.txt and is 16,984 bytes in size.

FIELD

The technology relates in part to device components, devices and methods having a high contrast signal to noise ratio.

SUMMARY

The general concept of using a nanopore for polymer sequencing is to electrophoretically drive a polymer (e.g. single stranded nucleic acid (e.g., DNA)) through a nanopore under aqueous conditions, and identify each individual monomer (e.g. nucleotide) of the strand as it passes through the sensing region of the nanopore based on its characteristic current modulation.

As a single stranded polymer (e.g. DNA) translocates a nanopore, excess noise is produced that can mask the transition between nucleotides. As shown herein, modifications to a protein nanopore can significantly improve the ratio between the contrast between monomers (e.g. nucleotides) and the excess noise herein termed the contrast signal to noise ratio (CNR). Provided herein are nanopores, devices and methods that exhibit a high contrast signal to noise ratio (CNR) for sensing molecules, or portions thereof. The nanopores, devices and methods described herein have the potential to become an accurate and efficient method for polymer sequencing (e.g. DNA sequencing).

Described herein are high contrast signal to noise ratio (CNR) nanopores, devices comprising nanopores and methods of use. In some embodiments, a high CNR nanopore comprises at least one mutagenesis modification of a protein pore. The CNR is determined as a contrast signal divided by a total noise value. The contrast signal is determined as the absolute difference between a first discrete level and a second discrete level within a measured residual current of the nanopore as a polymer translocates through the nanopore, in some embodiments. In certain embodiments, the first discrete level and the second discrete level can be calculated from at least 20 measurements of the same type of polymer as it translocates the nanopore. In some embodiments, the first discrete level and the second discrete level can be calculated from at least 50 measurements of the same type of polymer as it translocates the nanopore in some embodiments. In certain embodiments, the contrast signal is determined, without averaging, as the absolute difference between a first discrete level and a second discrete level within a measured residual current of the nanopore as a polymer translocates through the nanopore.

The total noise value is the square root of the sum of the squares of a first average root mean square noise value of the first discrete level at a set filter frequency and a second average root mean square noise value of the second discrete level at the set filter frequency, in some embodiments. The polymer is comprised of at least two sections where each section is comprised of at least a part of a monomer. To remove the potential effect of measurement artifacts, the discrete levels used to calculate the CNR are correlated to the composition of the sections of the polymer. A high CNR nanopore meets a set CNR threshold value of at least 2 at the set filter frequency, in some embodiments. In addition, at least one of the discrete levels used to calculate the CNR that meets the set threshold value for the CNR has an average duration at or below a set threshold value of 1 millisecond.

In some embodiments, a nanopore comprises one or more amino acid modifications that permit measurement of a first level and a second level within a residual current of the nanopore, as a polymer translocates through the nanopore, with a contrast signal to noise ratio (CNR) of two (2) or greater computed at a predetermined or set filter frequency; where the polymer comprises two or more sections, each of which sections comprises at least a portion of a monomer and which CNR is calculated as a contrast signal divided by a total noise value; the contrast signal is calculated as the absolute difference between the first level and the second level; each level used for calculation of the CNR correlates to a composition of a section of the polymer; at least one of the first level and the second level has an average duration of one millisecond or less; and which total noise value is the square root of the sum of the squares of a first average root mean square noise value of the first level at the predetermined filter frequency and a second average root mean square noise value of the second level at the predetermined filter frequency.

In some embodiments a method for determining the sequence of a polymer, comprises (a) contacting a polymer with a device of embodiment B1 or B2, (b) measuring the residual current of the nanopore under conditions in which the polymer translocates the nanopore, and (c) determining the sequence of at least a portion of the polymer based on levels within the residual current measurement.

In some embodiments, a nanopore comprises one or more amino acid modifications that permit measurement of a first level and a second level within a residual current of the nanopore, as a polymer translocates through the nanopore, with a contrast signal to noise ratio (CNR) of two (2) or greater computed at a predetermined filter frequency. In some embodiments, a nanopore with a CNR of two (2) or greater is a high CNR nanopore.

In some embodiments a polymer comprises two or more sections, each of which sections comprises at least a portion of a monomer. In some embodiments a CNR is calculated as a contrast signal divided by a total noise value. In some embodiments a CNR is calculated as a contrast signal divided by a total noise value and the contrast signal is calculated as the absolute difference between the first level and the second level. In some embodiments, each level used for calculation of a CNR correlates to a composition of a section of a polymer. In some instances, at least one of the first level and the second level has an average duration of one millisecond (ms) or less. In some embodiments the total noise value is the square root of the sum of the squares of a first average root mean square noise value of the first level at the predetermined filter frequency and a second average root mean square noise value of the second level at the predetermined filter frequency.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

DETAILED DESCRIPTION

Figure 1A:
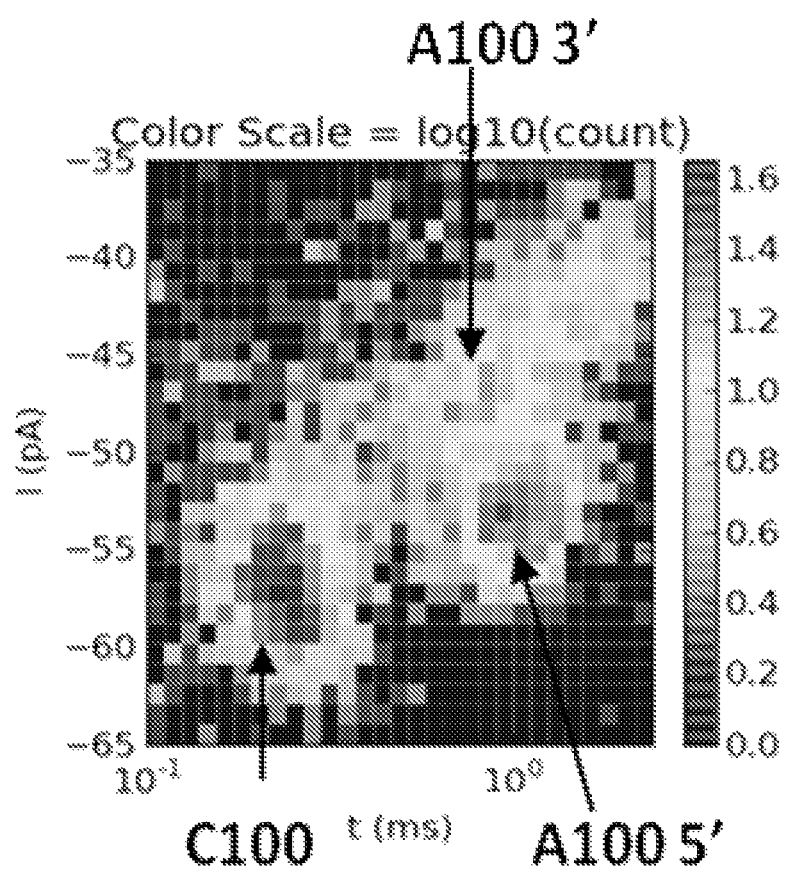
FIG. 1A shows the joint probability density plot of the amplitude and duration for polyA100 (SEQ ID NO: 2) and polyC100 (SEQ ID NO: 3) translocating through the 4SL135I nanopore.

In certain embodiments, the nanopores, devices and methods described herein can be used to detect polymers or portions thereof. In some embodiments the nanopores, devices and methods described herein can be used to detect the monomeric units (e.g. monomers) that make up a polymer. In some embodiments the nanopores, devices and methods described herein can be used to detect or determine the sequence of monomeric units (e.g. nucleotides) that make up a polymer (e.g. a strand of DNA or RNA). Such device components, devices and methods are useful for sensing target molecules, and may be used to sequence molecular polymers.

Polymers and Monomers

A polymer, as referred to herein, can be any molecular polymer. Some common molecular polymers are polynucleotides and polypeptides. A polymer can be a nucleic acid polymer, a protein polymer or a peptide polymer. A polymer can be a single stranded or double stranded DNA or RNA. A polymer can be a protein or peptide. Non-limiting examples of a polymer include a single stranded DNA, a double stranded DNA, a single stranded RNA, a double stranded RNA, a protein and a peptide. In certain embodiments, the polymer is single stranded DNA. In certain embodiments, the polymer is double stranded DNA.

A polymer can include two or more polymer sections and a polymer section can include at least a portion of a monomer. A monomer, as referred to herein, can be any molecule that may bind chemically to another molecule to form a polymer. A monomer can be naturally occurring, modified or synthetic. A monomer can be a nucleic acid or amino acid, for example. A nucleic acid monomer can be phosphorylated, oxidized, acetylated, methylated or sulfonated. A nucleic acid monomer can be a monophosphate nucleotide, modified nucleotide, methylated nucleotide, acetylated nucleotide or oxidized nucleotide. Non-limiting examples of a monomer include nucleotides, monophosphate nucleotides, modified nucleotides, methylated nucleotides and oxidized nucleotides. A nucleic acid monomer can be adenine (A), cytosine (C), thymine (T), guanine (G), uracil (U), modified cytosine, 7-methylguanine, xanthine, hypoxanthine, 5.6-dihydrouracil, 5-methylcytosine, N4-methylcytosine, hydroxymethylcytosine, or N6-methyladenine. In certain embodiments, a nucleotide can be selected from the non-limiting group of nucleotides consisting of the bases adenine (A), cytosine (C), thymine (T), guanine (G), uracil (U), modified cytosine, 7-methylguanine, xanthine, hypoxanthine, 5.6-dihydrouracil, 5-methylcytosine, N4-methylcytosine, hydroxymethylcytosine, and N6-methyladenine.

As an example, sequences of single stranded DNA are designated according to the following format. For a polymer that is single stranded DNA and is comprised of 10 adenine (A) bases followed by 4 guanine (G) bases and then 26 adenine (A) bases, it will be written as polyA10G4A26 (SEQ ID NO: 13) for example. As another example, 100 cytosine (C) bases in single stranded DNA will be written as polyC100 (SEQ ID NO: 3).

In some embodiments, nucleic acid polymers are comprised of sections. In some embodiments a polymer comprises at least two sections A section can include at least a part of one monomer. In some embodiments a section comprises one or more monomers. In some embodiments a section comprises two or more monomers. In some embodiments a polymer comprises two or more sections. In some embodiments a polymer comprises two or more sections, each of which sections comprises at least a portion of a monomer.

A "level" as used herein refers to a measurement of electrical current or conductance, any current value or any value derived mathematically from a current value. In some embodiments, the determination of a section is based upon it providing a distinct or discrete level compared to another section within a polymer. In some embodiments, a polymer that is used to compute the CNR is comprised of at least two distinct sections and is termed a heteropolymer. Using single stranded DNA as an example, the DNA strand polyA36G4 (SEQ ID NO: 14) could have two sections noted as A36 (SEQ ID NO: 15) and G4. A level (e.g., a current level in picoamps) for a section can be denoted as I_A36 (SEQ ID NO: 15) (for A36 (SEQ ID NO: 15)), or I_G4 (for G4), for example. Thus, a composition in a first section of a heteropolymer can give rise to a first level in the residual current and a composition of a second section of the heteropolymer can give rise to a second level in the residual current. A level can be based on measurements for a section of a polymer within the residual current as the polymer translocates the nanopore. A level often is an average of multiple measurements within the residual current. A level sometimes is a particular measurement within the residual current. A first level and a second level may be used to calculate a CNR value. The first level and second level often are measurably distinct. Measurably distinct levels sometimes are detectably different levels and sometimes are statistically different levels (e.g., a difference between levels is determined to be statistically significant). Where two levels are measurably distinct, each of a first level and a second level can also be referred to as a "discrete level."

In another example, the heteropolymer polyA50C50 (SEQ ID NO: 16) is comprised of two sections, the first section comprises 50 A bases and the second section comprises 50 C bases. In some embodiments a first level is measured for the first section (e.g., A50 (SEQ ID NO: 8)) and a second level is measured for the second section (e.g., C50 (SEQ ID NO: 12)). The first level can correspond to the first section and therefore the composition of the first section (e.g., A50 (SEQ ID NO: 8)) and the second level can correspond to the second section and therefore the composition of the second section (e.g., C50 (SEQ ID NO: 12)).

The heteropolymer polyA50C100 (SEQ ID NO: 17) is also comprised of two sections, the first section comprises 50 A bases and the second comprises 100 C bases, for example. In some embodiments, the discrete current level for C50 (SEQ ID NO: 12), (denoted I_C50 (SEQ ID NO: 12)), does not differ from the discrete current level for C100 (SEQ ID NO: 3), (denoted I_C100) (SEQ ID NO: 3). Thus, in some embodiments C50 (SEQ ID NO: 12) and C100 (SEQ ID NO: 3) both comprise a single section in the above example.

However, in some embodiments it is not mandatory that the section includes the same monomer. For example, for polyACTG the sections can be A, C, T and G where each section produces a discrete level. In another example, for polyACTG the sections can be AC, CT, and TG where each section produces a discrete level due to the signal not being localized over a single monomer within the nanopore.

In another example, it is possible that the monomers comprising the section are not contiguous. For example, with the single stranded DNA polyACTG, the sections can include the combination of A and T as well as another section being comprised of C and G. Such polymers can be used when a nanopore has two or more sensing regions that are separated within the nanopore and that when combined produce the measured residual current.

Correlation of the Discrete Levels to Sections of the Polymer

In some embodiments, the discrete levels of a polymer are correlated with the actual composition of the sections of the polymer. In some embodiments, when measuring the residual current of a nanopore as a polymer is translocating through it, different levels are detected due to effects such as artifacts and protein gating. For example, these levels, if used as one of the discrete levels to calculate the CNR, could appear to produce a high CNR that is not actually related to the composition of the polymer. Thus, in some embodiments, the CNR that is relevant to polymer sequencing is correlated to actual sections of the polymer measured, and not the additional artifacts. This correlation can be determined with one of the following non-limiting methods.

In some embodiments, this correlation is determined by allowing homopolymers, a polymer comprised of only the same monomer (e.g. polyA100 (SEQ ID NO: 2) or polyC100 (SEQ ID NO: 3)), to translocate through a nanopore and the residual current is measured. For example, the homopolymers would be comprised of the monomers that are expected or known to produce the discrete levels within the heteroligomer being measured to compute the CNR.

For example, in certain embodiments, a single stranded DNA polymer, polyA40C80A40 (SEQ ID NO: 4), comprises two sections, A40 (SEQ ID NO: 5) and C80 (SEQ ID NO: 6). In some embodiments, while it is expected that the residual current will show the levels I_A40 (SEQ ID NO: 5), I_C80 (SEQ ID NO: 6) and I_A40 (SEQ ID NO: 5) in sequence, there are only two distinct sections because the two A40 (SEQ ID NO: 5) regions are expected to produce the same average level, within the accuracy of the measurement. For example, the expected number of occurrences for the discrete levels for polyA40C80A40 (SEQ ID NO: 4) can be two occurrences of I_A40 (SEQ ID NO: 5) and one occurrence of I_C80 (SEQ ID NO: 6), where the I_C80 (SEQ ID NO: 6) occurrence is between the two I_A40 (SEQ ID NO: 5) occurrences. In some instances, while a polymer is translocating a nanopore, it is affected by diffusive motion that results in the polymer moving forwards and backwards through the nanopore. In some embodiments when diffusive motion is a factor, even under an applied bias that is meant to move a polymer through a nanopore in a forward only motion, the effects can be reduced by applying a higher bias. For example, this effect from diffusive motion means that for the example of polyA40C80A40 (SEQ ID NO: 4), the actual occurrences of the discrete levels can be I_A40 (SEQ ID NO: 5), I_C80 (SEQ ID NO: 6), I_A40 (SEQ ID NO: 5), I_C80 (SEQ ID NO: 6), and then I_A40 (SEQ ID NO: 5), or I_A40 (SEQ ID NO: 5), I_C80 (SEQ ID NO: 6), I_A40 (SEQ ID NO: 5), I_C80 (SEQ ID NO: 6), I_A40 (SEQ ID NO: 5), I_C80 (SEQ ID NO: 6) and then I_A40 (SEQ ID NO: 5) or similar combinations if the polymer moves backwards and then forward near the transition region. This diffusive effect is discussed in Lathrop et al. (D. K. Lathrop, E. N. Ervin, G. A. Barrall et al., "Monitoring the Escape of DNA from a Nanopore Using an Alternating Current Signal," *Journal of the American Chemical Society*, vol. 132, no. 6, pp. 1878-1885, 2010.).

Correlation Using Translocating Homopolymers

As noted above, a composition in a first section of a heteropolymer can give rise to a first level in the residual current and a composition of a second section of the heteropolymer can give rise to a second level in the residual current. To verify that the first level correlates to a composition in the first section of the heteropolymer, and the second level correlates to a composition in the second section of the heteropolymer, the composition in the first section can be incorporated into a first homopolymer and the composition of the second section can be incorporated into a second homopolymer, and the first homopolymer and the second homopolymer can be translocated through a nanopore and analyzed. Homopolymers measured to correlate the discrete levels to the composition of the sections of a heteropolymer can be polyA100 (SEQ ID NO: 2) and polyC100 (SEQ ID NO: 3) for example. For example, the difference (e.g., the contrast) between the measured level for the homopolymer polyA100 (SEQ ID NO: 2) and the measured level of a polyC100 (SEQ ID NO: 3) can be used to calculate a contrast signal. The calculated contrast signal for the two homopolymers can be used to provide information to correlate the levels measured in a heteropolymer to the composition of the sections of the polymer. For example, the contrast signal between polyA100 (SEQ ID NO: 2) and polyC100 (SEQ ID NO: 3) can be used to correlate the levels measured for the heteropolymer polyA50C50 (SEQ ID NO: 16) to the sections A50 (SEQ ID NO: 8) and C50 (SEQ ID NO: 12). In some embodiments, the first level and the second level obtained for a heteropolymer (e.g., polyA50C50 (SEQ ID NO: 16)) are correlated to the respective sections of the heteropolymer by measuring the residual current of a first homopolymer (e.g., poly A100 (SEQ ID NO: 2)) and a second homopolymer (e.g., polyC100 (SEQ ID NO: 3)) translocating through the same nanopore. In this example the first homopolymer (e.g., polyA100 (SEQ ID NO: 2)) comprises the same composition as in the first section of the heteropolymer (e.g., polyA50C50 (SEQ ID NO: 16)) that produces the first level used to compute the CNR and the second homopolymer (e.g., polyC100 (SEQ ID NO: 3)) comprises the same composition as in the second section of the heteropolymer that produced the second level used to compute the CNR.

In certain embodiments, both the homopolymers and heteropolymer can be present in the same electrolyte solution that is being measured to compute the CNR. This can minimize the variation that is known to occur between nanopores and experimental setups. The residual current values measured for polyA100 (SEQ ID NO: 2) and polyC100 (SEQ ID NO: 3) do not have to exactly equal the respective levels seen within the heteropolymer polyA40C80A40 (SEQ ID NO: 4) for example. However, in some embodiments, it is expected that the absolute difference between discrete levels within the heteropolymer and the absolute difference between the values for the two homopolymers will be approximately equal or substantially similar (within ~30%) for the same measurement conditions. For example, the I_A40 (SEQ ID NO: 5), within polyA40C80A40 (SEQ ID NO: 4) might be 49 pA and the I_C80 (SEQ ID NO: 6) is 61 pA, giving an absolute difference of 12 pA. In this example, the average residual current for polyA100 (SEQ ID NO: 2) might be 47 pA current and the average residual current for polyC100 (SEQ ID NO: 3) might be 59 pA, providing an absolute difference of about 12 pA and thus approximately the same contrast signal. In another example, the average residual current level for polyA100 (SEQ ID NO: 2) might be 49.4 pA and the average residual current for polyC100 (SEQ ID NO: 3) might be 58.5 pA, producing a contrast signal of 9.1 pA. While this is a lower contrast signal than seen for the A40 (SEQ ID NO: 5) and C80 (SEQ ID NO: 6) sections, the values are sufficiently close and the relative blocking levels are the same relative magnitude (e.g. polyA100 (SEQ ID NO: 2) blocks more than polyC100 (SEQ ID NO: 3)), and, in this instance, the discrete levels can be correlated to the composition of the sections A40 (SEQ ID NO: 5) and C80 (SEQ ID NO: 6) of the polymer.

Correlation Using Immobilized Homopolymers

As noted above, a composition in a first section of a heteropolymer can give rise to a first level in the residual current and a composition of a second section of the heteropolymer can give rise to a second level in the residual current. To verify that the first level correlates to a composition in the first section of the heteropolymer, and the second level correlates to a composition in the second section of the heteropolymer, the composition in the first section can be incorporated into a first homopolymer and the composition of the second section can be incorporated into a second homopolymer, and the first homopolymer and the second homopolymer can be immobilized to a nanopore and analyzed. Thus, in certain embodiments, homopolymers are measured as they are immobilized within a nanopore and the residual current is measured. This can be done in a standard experimental setup as is known and as described in Purnell (R. F. Purnell, K. K. Mehta, and J. J. Schmidt, "Nucleotide Identification and Orientation Discrimination of DNA Homopolymers Immobilized in a Protein Nanopore," *Nano letters*, Aug. 13, 2008). In some embodiments, the average residual current values obtained for the immobilized homopolymers do not always have to exactly equal the levels within the heteropolymer and do not always provide the same contrast signal. However, in virtually all experiments to date, the immobilized measurements maintain the relationship between the discrete levels. For example, if the I_A40 (SEQ ID NO: 5) of polyA40C80A40 (SEQ ID NO: 4) is lower than the I_C80 (SEQ ID NO: 6) for the section C80 (SEQ ID NO: 6), then the residual current value for immobilized polyA100 (SEQ ID NO: 2) would be lower than the residual current value for polyC100 (SEQ ID NO: 3). In some embodiments, while the contrast signal may vary between the translocating and immobilized measurements, the discrete values produced by the heteropolymer are correlated to the composition of the sections of the heteropolymer using the levels from those of immobilized homopolymers using known data analysis techniques.

Correlation Using a Heteropolymer to Map the Nanopore

In certain embodiments, the CNR is computed between different sections of the polymer that cannot be measured using homopolymers. For example, it is known that a homopolymer that includes at least 40 G bases is difficult to synthesize by methods known at the time of this application. To address this problem, in certain embodiments, the discrete level can be correlated to the composition of the section of the polymer by mapping the nanopore with a polymer that contains a short region of a monomer or monomers that are within the heteropolymer being used to compute the CNR. The basic procedure for the mapping of a nanopore used in some embodiments has been previously described in D. Stoddart, A. J. Heron, E. Mikhailova, G. Maglia, and H. Bayley, "Single-nucleotide discrimination in immobilized DNA oligonucleotides with a biological nanopore," Proc. Natl. Acad. Sci. USA, vol. 106, pp. 7702-7707, 2009. In certain embodiments, the discrete level is correlated to a composition of a section of the heteropolymer used to compute the CNR by mapping a nanopore with a different polymer that comprises a short region of a monomer located within the first polymer used to compute the CNR. For example, the heteropolymer used to compute the CNR is a single strand of DNA such as polyA40G4A40 (SEQ ID NO: 18). The correlation of the levels to the composition of the sections of the polymer can be demonstrated where the section G4 is moved down the polymer sequence while each strand is immobilized in the nanopore. In some embodiments, the residual current is measured as the polymer blocks the nanopore and a map can be created with a value of the residual current as the G4 section is moved down the strand. For example, the G4 section can be placed such that it occupies every position that can be located within the nanopore. For example, for the nanopore that is wild type alpha hemolysin, the following sequences in Table 1 can be used:

TABLE 1

| NAME | SEQUENCE |
|---|---|
| BtnTg-5'-(A36)(G4)3 | BiotinTEG-5'-AAGGGGAAAAAAAAAAAAAA-A20-3' (SEQ ID NO: 19) |

TABLE 1-continued

| NAME | SEQUENCE |
|---|---|
| BtnTg-5'-(A36)(G4)4 | BiotinTEG-5'-AAAGGGGAAAAAAAAAAAAA-A20-3' (SEQ ID NO: 20) |
| BtnTg-5'-(A36)(G4)5 | BiotinTEG-5'-AAAAGGGGAAAAAAAAAAAA-A20-3' (SEQ ID NO: 21) |
| BtnTg-5'-(A36)(G4)6 | BiotinTEG-5'-AAAAAGGGGAAAAAAAAAAA-A20-3' (SEQ ID NO: 22) |

In Table 1, BtnTg-5'-(A36)(G4)$_3$ indicates that there is a Biotin TEG molecule on the 5' end of the single stranded DNA. There are 4 G bases that are moved down the strand of DNA and the 3 indicates that the first G base is located 3 bases from the TEG molecule on the 5' end. For the example of wild type alpha hemolysin, this could continue through the first G base being placed in the $21^{st}$ position. In certain embodiments, the target section is placed in every position along the single stranded DNA that can be located within the nanopore. In some embodiments, the residual current value with the largest difference from the background sections would be compared to the measured discrete level in order to determine whether the measured discrete level correlates to the polymer section of interest rather than a measurement artifact.

In certain embodiments, if the CNR is to be computed for a polymer that is comprised of polyA40GA40 (SEQ ID NO: 23), the nanopore is mapped with only a single G base being moved down the single stranded DNA. For example, BtnTg-5'-(A36)(G)3, BtnTg-5'-(A36)(G)4 and so on.

Two or More Sensing Regions in the Nanopore

In certain embodiments, the nanopore may contain more than one sensing region. In order to identify the locations of the sensing regions, the nanopore can be mapped with a single monomer within a homopolymer comprised of a different monomer, as in the case described directly above with polyA40GA40 (SEQ ID NO: 23). In some embodiments, once the map is constructed, the location of the sensing region or regions is determined. For example, for a nanopore mapped for polyA40GA40 (SEQ ID NO: 23) with BtnTg-5'-(A36)(G)3 through BtnTg-5'-(A36)(G)21, with G occupying every position from 3 to 21, the nanopore has sensitive regions at positions 6 and position 17.

In certain embodiments, once the location of the sensing regions within a given protein pore are known, the discrete levels can be correlated to the composition of the sections of the polymer by placing distinct monomers in different positions along a DNA test strand. For instance, in the example where a nanopore has a sensitive region at position 6 and another at position 17, a polymer comprised of polyA5GA10GA23 (SEQ ID NO: 24) can be used to compute the CNR. In some instances, the discrete levels for this polymer used to compute the CNR would correspond to the sections AA and GG. The immobilized polymers BtnTg-5'-polyA40 ("polyA40" disclosed as SEQ ID NO: 5) and BtnTg-5'-polyA5GA10GA23 ("polyA5GA10GA23" disclosed as SEQ ID NO: 24) can be used to correlate the discrete levels to the composition of the sections of the polymer.

In some embodiments, this method is used if a discrete level is predicted to be due to two different monomers that are not contiguous within a polymer. For example, the CNR is to be computed for the polymer polyA5GA10TA23 (SEQ ID NO: 25) and the two discrete levels are predicted to be produced by the sections AA and GT, where I_GT is due to the nanopore having sensitive regions at positions 6 and 17. To correlate these discrete levels to the composition of the sections of the polymer, the immobilized polymers comprised of BtnTg-5'-polyA40 ("polyA40" disclosed as SEQ ID NO: 5) and BtnTg-5'-polyA5GA10TA23 ("polyA5GA10TA23" disclosed as SEQ ID NO: 25) can be used.

Normalized Current

In some embodiments the current of a nanopore can vary per experiment based on the exact experimental conditions. As a result, it may be necessary to normalize the residual current values compared to the open channel current value of the nanopore. In some instances, the normalized current value is the quotient of the residual current divided by the open channel current. Thus, in some instances, the discrete levels within the residual current measured as the polymer translocates the nanopore can be correlated to the values measured for the homopolymers based on the normalized values. In some embodiments, these normalized values are used for the correlation of the discrete levels to the actual composition of the sections of the polymer rather than being used in the calculation of the CNR.

Average Durations of the Sections of the Polymer

In certain embodiments, the duration times for the discrete level for each of the residual current measurements, in certain embodiments at least 50 measurements (e.g. at least 75, at least 100, at least 200, at least 300, at least 500, or at least 1000 measurements), are averaged and this provides the average duration that is at or below the set threshold for the average duration. In certain embodiments, the duration times for the discrete level for each of the residual current measurements, in certain embodiments at least 50 measurements (e.g. at least 75, at least 100, at least 200, at least 300, at least 500, or at least 1000 measurements), are used to compute the arithmetic mean of the duration times for the discrete levels and the arithmetic mean provides the average duration that is at or below the set threshold for the average duration In certain embodiments, the polymer is single stranded DNA. In certain embodiments, the polymer is single stranded DNA and the sections are comprised of monomers. In certain embodiments, the probability distribution of duration times for the discrete level, in certain embodiments at least 50 measurements (e.g. at least 75, at least 100, at least 200, at least 300, at least 500, or at least 1000 measurements), is fit well to a mathematical model.

Exponential Model

In certain embodiments, the mathematical model is an exponential model where the average duration of the discrete level is the time constant tau of a normalized exponential distribution, (1/tau)*exp(−duration/tau). In some embodiments, the probability distribution of duration times for the discrete level of a polymer is well fit by an exponential model when the section of the polymer that has been correlated to the discrete level is comprised of a single monomer. In certain embodiments, the probability distribution of duration times for the discrete level of a polymer is well fit by an exponential model when an enzyme, exonuclease, polymerase or hybridized sections of complementary DNA to portions of the single stranded DNA are used to control the rate of translocation.

Translocation Model

In certain embodiments, the mathematical model is a translocation model of the probability distribution of durations based upon the solution to a set of n coupled first order differential equations, where n is the number of identical monomers in the section. The fit of distribution of translocation times from this solution is:

$$P(\kappa, p_f; t) = \frac{\sum_{j=1}^{n}(-1)^j \sin^2\phi_j e^{-(1-2\sqrt{p_f(1-p_f)}\cos\phi_j)\kappa t}}{\sum_{j=1}^{n}\frac{(-1)^j \sin^2\phi_j}{(1-2\sqrt{p_f(1-p_f)}\cos\phi_j)\kappa}} \text{ with } \phi_j = \frac{j\pi}{n+1}.$$

Here $\kappa$ and $p_f$ are fitting parameters representing the mean rate of moving from one monomer to a neighboring monomer and the probability that the neighboring monomer moved to is in the forward direction.

From this distribution, a Tmax value can be obtained from this type of fit and this value is set as the average duration of the discrete level. The Tmax value is the most probable duration, meaning that it is the time corresponding to the maximum in the model fit to a probability distribution of the discrete level durations. In some embodiments, the probability distribution of duration times for the discrete level is well fit by a translocation model when the section of the polymer is comprised of approximately 2 to 10 identical monomers (e.g. A2 or A10 (SEQ ID NO: 26)).

Lubensky Translocation Model

In certain embodiments, the mathematical model is a Lubensky translocation model of the distribution of durations as described in Lubensky et al. (D. K. Lubensky, and D. R. Nelson, "Driven Polymer Translocation Through a Narrow Pore," *Biophys. J.*, vol. 77, no. 4, pp. 1824-1838, Oct. 1, 1999).

From this distribution, a Tmax value can be obtained from this type of fit and this value is set as the average duration of the discrete level. In some embodiments, the Tmax value is the most probable duration, meaning that it is the time corresponding to the maximum in the model fit to a probability distribution of the discrete level durations. In some embodiments, the probability distribution of duration times for the discrete level is well fit by a Lubensky translocation model when the section of the polymer is comprised of approximately 10 or more monomers (e.g. A10 (SEQ ID NO: 26) or A20 (SEQ ID NO: 27)).

Average Duration Threshold

The average duration for at least one discrete level used to calculate the CNR that meets the CNR threshold at the set filter frequency is at or below the maximum duration threshold. In certain embodiments, this threshold can be set to about 1 millisecond or less, about 900 microseconds or less, about 800 microseconds or less, about 700 microseconds or less, about 600 microseconds or less, about 500 microseconds or less, about 400 microseconds or less, about 300 microseconds or less, about 200 microseconds or less, about 100 microseconds or less, about 50 microseconds or less, or about 10 microseconds or less. In certain embodiments, the average duration for both discrete levels used to calculate the CNR that meets the CNR threshold is at or below the maximum duration threshold.

Data Acquisition, Sampling Frequency, Effective Bandwidth and Set Filter Frequency In certain embodiments, the residual current measurements are acquired using a Direct Current (DC) measurement system. In certain embodiments, a DC bias, which is a substantially constant applied voltage, is applied across the nanopore. In some embodiments, the residual current signal is low pass filtered with an analog filter prior to digitally acquiring the residual current data at an acquisition frequency. The resulting data can then be digitally low pass filtered to an effective bandwidth and then resampled at a sampling frequency. In certain embodiments, the CNR can be computed at a set filter frequency that is equal to the effective bandwidth. In certain embodiments, the CNR can be computed at a set filter frequency that is lower than the effective bandwidth.

In certain embodiments, the residual current measurements can be acquired using an Alternating Current (AC) measurement system. In certain embodiments, the AC measurement system is the measurement system as described in U.S. Pat. No. 7,731,826, herein incorporated by reference. In certain embodiments, the AC system utilizes a source signal that is periodic (e.g. a sine wave or square wave) that is defined by an applied bias and frequency. In certain embodiments, the frequency of the source signal is equal to a center frequency. Non-limiting examples of the frequency of the source signal can be 10 kHz to 300 kHz or greater (e.g. 10 kHz, 20 kHz, 30 kHz, 40 kHz, 50 kHz, 60 kHz, 70 kHz, 80 kHz, 90 kHz, 100 kHz, 150 kHz, 200 kHz, 250 kHz, 300 kHz or greater). In some embodiments, the source signal is applied and the residual current signal is low pass filtered with an analog filter prior to digitally acquiring the residual current data at an acquisition frequency. The resulting data can then be demodulated as described in U.S. Pat. No. 7,731,826 to produce the effective DC measurement of the residual current, in some embodiments. In certain embodiments, the data can be further low pass filtered to an effective bandwidth and resampled at a sampling frequency. In certain embodiments, the CNR can be computed at a set filter frequency that is equal to the effective bandwidth. In certain embodiments, the CNR can be computed at a set filter frequency that is lower than the effective bandwidth.

In certain embodiments, a DC bias is applied while acquiring the residual current measurements using the AC measurement system. In certain embodiments, the DC bias is in the range of about 1 mV to about 300 mV (e.g. 1 mV, 2 mV, 3, mV, 4 mV, 5 mV, 6 mV, 7 mV, 8 mV, 9 mV, 10 mV, 15, mV, 20 mV, 25 mV, 30 mV, 35 mV, 40 mV, 45 mV, 50 mV, 60 mV, 70 mV, 80 mV, 90 mV, 100 mV, 110 mV, 120 mV, 130 mV, 140 mV, 150 mV, 160 mV, 170 mV, 180 mV, 190 mV, 200 mV, 210 mV, 220 mV, 230 mV, 240 mV, 250 mV, 260 mV, 270 mV, 280 mV, 290 mV or 300 mV). In certain embodiments, the DC bias is in the range of about 5 mV to about 300 mV (e.g. at least 5 mV, 6 mV, 7 mV, 8 mV, 9 mV, 10 mV, 15, mV, 20 mV, 25 mV, 30 mV, 35 mV, 40 mV, 45 mV, 50 mV, 60 mV, 70 mV, 80 mV, 90 mV, 100 mV, 110 mV, 120 mV, 130 mV, 140 mV, 150 mV, 160 mV, 170 mV, 180 mV, 190 mV, 200 mV, 210 mV, 220 mV, 230 mV, 240 mV, 250 mV, 260 mV, 270 mV, 280 mV, 290 mV or 300 mV).

Acquisition Frequency

In some embodiments, the acquisition frequency is the rate at which the data is digitally acquired.

Sampling Frequency

In some embodiments, the sampling frequency is the final number of data points per second.

Low Pass Filter

In some embodiments, a low pass filter is a filter that passes low frequency signals, but attenuates signals with frequencies approaching and higher than the cutoff frequency. In some instances, the low pass filter is defined by the cutoff frequency, the frequency at which the filter attenuates the input power by about 3 dB. For example, for a 10 kHz low pass filter, the cutoff frequency is 10 kHz and the filter attenuates the input power by about 3 dB at 10 kHz.

Effective Bandwidth

In some instances, the largest signal bandwidth that can be realized is defined as the Nyquist frequency, which is the sampling frequency divided by 2. In some instances, the residual current signal or data is filtered using a low pass or band-pass filter to an effective bandwidth that is at or below the Nyquist frequency. In certain embodiments, the sampling frequency is 5 times greater than the effective bandwidth.

In certain embodiments, the low pass filtering is done prior to acquiring the data at the acquisition frequency using an analog filter for anti-aliasing or after acquiring the data at the acquisition frequency using a digital filter. In certain embodiments, the residual current signal is low pass filtered using an analog low pass filter for anti-aliasing and then low pass filtered again after acquiring the data at the acquisition frequency using a digital low pass filter.

Set Filter Frequency for CNR Calculation

The CNR is calculated at a specific frequency, termed the set filter frequency or predetermined filter frequency, in some embodiments. In certain embodiments, the set filter frequency is equal to the effective bandwidth. In certain embodiments, the data is further filtered with a low pass filter to the set filter frequency (e.g. 10 kHz).

In certain embodiments, non-limiting examples of the set filter frequency are frequencies between 1 kHz and 500 kHz (e.g. 1 kHz, 2 kHz, 3 kHz, 4 kHz, 5 kHz, 6 kHz, 7 kHz, 8 kHz, 9 kHz, 10 kHz, 20 kHz, 30 kHz, 40 kHz, 50 kHz, 100 kHz, 200 kHz, 300 kHz, 400 kHz and 500 kHz). In certain embodiments, the set filter frequency is 10 kHz.

In certain embodiments, the signal is low pass filtered using an analog filter for anti-aliasing. In certain embodiments, the signal is low pass filtered using an analog 1-pole Bessel filter. The data can then be digitally acquired at the acquisition frequency and then low pass filtered to the effective bandwidth. In certain embodiments, the data is low pass filtered to the effective bandwidth using a digital 8-pole Bessel filter. The data is then resampled at the sampling frequency in some embodiments. In certain embodiments, the sampling frequency is equal to the acquisition frequency. In certain embodiments, the sampling frequency is lower than the acquisition frequency. In certain embodiments, the CNR is computed at a set filter frequency that equals the effective bandwidth. In certain embodiments, the CNR is computed at a set filter frequency that is lower than that of the effective bandwidth. In certain embodiments, the CNR is computed at a set filter frequency that is lower than the effective bandwidth by low pass filtering the data to the set filter frequency. In certain embodiments, the data is low pass filtered to the set filter frequency using a 3-pole Bessel filter.

As an example, the signal is low pass filtered with a 1-pole Bessel analog filter to 170 kHz for anti-aliasing. The data can then be digitally acquired at an acquisition frequency of 1.25 MHz. Then the data can be digitally low pass filtered to 100 kHz, the effective bandwidth, using a digital 8-pole Bessel filter for example. The data can then be resampled at a sampling frequency of 500 kHz, which provides a Nyquist frequency of 250 kHz. The CNR can be calculated at a set filter frequency (e.g. 10 kHz), which is lower than the effective bandwidth (e.g. 100 kHz). In some embodiments, the data is low pass filtered to the set filter frequency of 10 kHz using a 3-pole Bessel filter.

In certain embodiments, an AC source signal is applied and the AC signal is low pass filtered using an analog filter for anti-aliasing. In certain embodiments, the signal is low pass filtered using an analog 1-pole Bessel filter. The data can them be digitally acquired at the acquisition frequency in some embodiments. The data can then be demodulated as described in U.S. Pat. No. 7,731,826 to produce the effective DC measurements of the residual currents. In certain embodiments, the data is low pass filtered using a digital filter to an effective bandwidth. In certain embodiments, the data is low pass filtered to the effective bandwidth using a digital 8-pole Bessel filter and resampled at the sampling frequency. In certain embodiments, the sampling frequency is equal to the AC source frequency. In certain embodiments, the CNR will be computed at a set filter frequency that equals the effective bandwidth. In certain embodiments, the CNR is computed at a set filter frequency that is lower than that of the effective bandwidth. In certain embodiments, the CNR is computed at a set filter frequency that is lower than the effective bandwidth by low pass filtering the data to the set filter frequency. In certain embodiments, the data is low pass filtered to the set filter frequency using a 3-pole Bessel filter.

As an example, a sinusoidal source signal of 100 mV and a frequency of 50 kHz is applied. The AC signal can be low pass filtered using a 1-pole analog filter for anti-aliasing with a cutoff frequency of 175 kHz. The data can then be digitally acquired at an acquisition frequency of 800 kHz. The data can then be demodulated using the source signal to produce the effective DC measurements of the residual currents at a sampling frequency of 50 kHz (equal to the source frequency). The data can then be digitally low pass filtered using an 8-pole Bessel filter to 10 kHz. In some embodiments, the CNR is then computed at a set filter frequency of 10 kHz, which is equal to the effective bandwidth.

Contrast Signal

In some embodiments, a contrast signal typically is computed as the absolute difference between the average first level and the average second level. In certain embodiments, the contrast signal is computed as the absolute difference between an individual measurement of the first level and an individual measurement of the second level.

The contrast signal can be measured in the following manner, for example. Polymers of the same composition and sequence of monomers can be allowed to translocate through the nanopore. In some instances, the polymer of interest often is comprised of sections and contains at least two distinct sections. In some instances, the sequence of the polymer is known. In some embodiments, a residual current measurement is taken as each polymer translocates the nanopore. In some embodiments, a residual current measurement is a measurement of the reduced current that occurs as a polymer is blocking a nanopore. In certain embodiments, at least 50 measurements of the residual current of the polymer translocating the nanopore are recorded. In certain embodiments, at least 75 measurements of the residual current of the polymer translocating the nanopore are recorded. In certain embodiments, at least 100 measurements of the residual current of the polymer translocating the nanopore are recorded. In certain embodiments, at least 200 measurements of the residual current of the polymer translocating the nanopore are recorded. In certain embodiments, at least 300 measurements of the residual current of the polymer translocating the nanopore are recorded. In certain embodiments, at least 500 measurements of the residual current of the polymer translocating the nanopore are recorded. In certain embodiments, at least 1000 measurements of the residual current of the polymer translocating the nanopore are recorded. In some embodiments, the value for a discrete level is the average of the values for each of the levels for the recorded measurements.

In certain embodiments, the measured residual currents may not show the expected number of occurrences of the discrete levels in every measurement of the polymer. In some measurements, a fewer number of the expected occurrences of the discrete levels may occur, the expected number of occurrences may occur, or more than the expected number of occurrences may occur. For example, with polyA40C80A40 (SEQ ID NO: 4), the expected number of occurrences is two occurrences of I_A40 (SEQ ID NO: 5) and one occurrence of I_C80 (SEQ ID NO: 6), where the I_C80 (SEQ ID NO: 6) occurs between the two I_A40 (SEQ ID NO: 5) occurrences. An example of a fewer number of expected occurrences of the discrete levels can be just one occurrence of I_A40 (SEQ ID NO: 5) or one occurrence of I_A40 (SEQ ID NO: 5) followed by one occurrence of I_C80 (SEQ ID NO: 6). An example of more than the expected number of occurrences of the discrete levels, which is due to the previously discussed diffusive motion, can be I_A40 (SEQ ID NO: 5), I_C80 (SEQ ID NO: 6), I_A40 (SEQ ID NO: 5), I_C80 (SEQ ID NO: 6), followed by I_A40 (SEQ ID NO: 5) in sequence. In certain embodiments, at least 50 measurements that contain at least the expected number of occurrences of the discrete levels are recorded. In certain embodiments, at least 75 measurements that contain at least the expected number of occurrences of the discrete levels are recorded. In certain embodiments, at least 100 measurements that contain at least the expected number of occurrences of the discrete levels are recorded. In certain embodiments, at least 200 measurements that contain at least the expected number of occurrences of the discrete levels are recorded. In certain embodiments, at least 500 measurements that contain at least the expected number of occurrences of the discrete levels are recorded. In certain embodiments, at least 1000 measurements that contain at least the expected number of occurrences of the discrete levels are recorded. In certain embodiments, if a measurement demonstrates the expected number of occurrences of the discrete levels and the levels are correlated to the composition of the sections of the polymer, the measurement is included in the CNR calculation. In certain embodiments, if a measurement demonstrates more than the expected number of occurrences of the discrete levels and the levels are correlated to the composition of the sections of the polymer, the measurement can be included in the CNR calculation. For example, for the single stranded DNA polymer polyA40C80A40 (SEQ ID NO: 4), approximately 80% of the events might show at least the expected number of occurrences for the discrete levels, where the expected occurrences are an occurrence of I_A40 (SEQ ID NO: 5) followed by an occurrence of I_C80 (SEQ ID NO: 6) and then an occurrence of I_A40 (SEQ ID NO: 5) again. In this case, the 20% of the events that do not show at least the expected number of occurrences for the discrete levels are not used for the calculation of the CNR. In this example, approximately 80% of the 80% of the measurements that show at least the expected number of occurrences for the discrete levels show exactly the number of expected occurrences of the discrete levels and these measurements are used to calculate the CNR. In some instances, the remaining measurements that show more than the expected number of occurrences of the discrete levels can be used in addition to the measurements showing exactly the number of expected occurrences to calculate the CNR.

In some embodiments, the predicted values for the discrete levels are known before the polymer translocates the nanopore. Predicted values can be determined by the same methods described for correlating the discrete levels to the composition of the sections of the polymer (e.g. using translocating homopolymers, immobilized homopolymers or mapping targeted sequences). These values can be used with data processing techniques such as the Viterbi Algorithm based on a Hidden Markov Model to identify the discrete levels in a residual current measurement. Non-limiting alternative examples to the Viterbi Algorithm include the Forward-Backward Algorithm and the Segmental K-Means Algorithm also based on the Hidden Markov Model. These algorithmic approaches can be especially useful if the measurements do not show clearly distinguishable discrete levels by eye, but can be determined through the use of known data processing techniques.

In some embodiments, the difference between discrete levels is large enough that the levels can be clearly distinguished without additional data processing. In these embodiments, additional data processing techniques can be used or the values for the discrete levels can be computed without additional processing.

In certain embodiments, the values for the discrete levels are measured at the effective bandwidth. In certain embodiments, the values for the discrete levels are measured at the set filter bandwidth. When the values for the discrete levels are measured at the set filter bandwidth below the sampling bandwidth, the transition from one discrete level to the next can comprise one or more sample values. Including this transition between discrete levels in the computation of the average amplitude of the discrete levels can result in erroneous values for the average amplitude. In some embodiments, the effect from the transition from one discrete level to the next is negligible and no removal of data is necessary. However, if the effect from the transition is not negligible, further steps often are required. In certain embodiments, in order to eliminate this source of error in the computation of the average amplitude of each discrete level, a portion of the beginning of the discrete level and a portion of the end of the discrete level can be removed. In certain embodiments, approximately one quarter of a time period corresponding to the set filter bandwidth is removed at the beginning and end of the discrete level. In certain embodiments, approximately one half of a time period for the set filter bandwidth is removed at the beginning and end of the discrete level. For example, if the effective bandwidth is 100 kHz and the set filter frequency is 10 kHz, then the time period corresponding to the set filter bandwidth is 100 microseconds (1/frequency, 1/10,000). Thus, one quarter of a time period would be about 25 microseconds and one half of a time period would be about 50 microseconds.

In certain embodiments, the orientation of a polymer can affect the residual currents that are measured. For example, the single stranded DNA polyA100 (SEQ ID NO: 2) with the 3' end entering the nanopore first can have a different residual current value than polyA100 (SEQ ID NO: 2) entering the nanopore with the 5' end first. In embodiments where the orientation of the polymer affects the residual current measurements, the CNR is computed and correlated to the composition of the sections of the polymer being tested using polymers with the same orientation relative to the nanopore.

Total Noise Value

The root mean square noise value for each of the discrete levels within each residual current measurement used to calculate the contrast signal can be computed at the set filter frequency. The noise value for each discrete level can then be averaged over the measurements to provide an average noise value for that discrete level. The total noise value can be computed by taking the square root of the sum of the squares of the average noise value for each of the two discrete levels used to calculate the contrast signal at the set filter frequency.

In some embodiments, when the values for the discrete levels are measured at a set filter bandwidth below the sampling bandwidth, the transition from one discrete level to the next will comprise one or more sample values. Including this transition between discrete levels in the computation of the noise value of the discrete levels will result in erroneous values for the noise values. To eliminate this source of error in the computation of the noise value of each discrete level, portions of the beginning and end of the discrete level can be removed prior to the noise computation. In certain embodiments, the portion removed from the beginning or end will be equal to the time of one quarter of a time period that is determined by the set filter frequency. For example, if the set filter frequency is 10 kHz, then one time period is 100 microseconds. This would result in approximately 25 microseconds being cut from the beginning of the discrete level and 25 microseconds being cut from the end of the discrete level. In certain embodiments, the portion removed from the beginning and end will be equal to approximately one half of a time period.

Contrast Signal to Noise Ratio (CNR)

In some embodiments, the Contrast Signal to Noise Ratio (CNR) is computed at the set filter frequency by dividing the contrast signal by the total noise value.

Threshold for the CNR

In some embodiments, the CNR at the set filter frequency meets at least a set threshold value. In some embodiments a nanopore which permits measurement of two levels has a CNR of 2 or greater. In some embodiments a nanopore which permits measurement of two or more levels has a CNR of 2.0 or greater, 2.5 or greater, 3.0 or greater, 3.5 or greater, 4.0 or greater, 4.5 or greater, 5.0 or greater, 5.5 or greater, 6.0 or greater, 6.5 or greater, 7.0 or greater, 7.5 or greater, 8.0 or greater, 8.5 or greater, 9.0 or greater, 9.5 or greater, or 10.0 or greater. In certain embodiments, the set threshold value is at least 2, at least 2.5, at least 3, at least 3.5, at least 4, at least 4.5, at least 5, at least 6, at least 7, at least 8, at least 9, or at least 10.

In certain embodiments, the CNR threshold value is met for at least one set of two discrete levels. In certain embodiments, the CNR threshold value is met for at least two sets, at least 3 sets, at least 4 sets, or at least 5 sets of two discrete levels. For example, for the single stranded DNA polymer polyACTG, the CNR threshold might only be met for the contrast signal between the A section and the G section and thus would meet the CNR threshold for at least one set of two discrete levels. If the CNR met the threshold for the A section and the G section, and the A section and the C section, then this meets the threshold for at least two sets of two discrete levels.

Examples of Testing Conditions

In some embodiments a nanopore does not have to be used for sequencing or some other practical application under the conditions in which it is tested to demonstrate the high CNR. For example, if a nanopore can be shown to demonstrate a CNR that meets the threshold of at least 2 as described herein under any known conditions, it is considered a high CNR nanopore according to this patent. For example, if a polymer sequencing system is using a protein nanopore and allowing the sections of the polymer to translocate with an average duration of 5 milliseconds for a discrete level, and it can be shown that under a different set of testing conditions, the average duration is 1 millisecond or less for at least one of the discrete levels used to calculate the CNR, and the CNR threshold is met with these testing conditions, then the nanopore is considered a high CNR nanopore as defined by this patent.

This section is provided to give examples of the testing conditions that can be used to measure the CNR at a set filter frequency. However, these example testing conditions are in no way to be construed as limiting in any way.

Single Stranded DNA

In some instances, the discrete levels within a residual current measurement of a polymer translocating a nanopore will vary based on the composition and sequence of the polymer. In addition, the rate of the translocation of the sections of the polymer can also vary based on the composition and sequence of the polymer. For example, polyC100 (SEQ ID NO: 3) translocates through the protein nanopore wild type alpha hemolysin approximately 8 times faster than polyA100 (SEQ ID NO: 2). Any strand of single stranded DNA with a known sequence that is synthesized can be used to measure the CNR. In certain embodiments, the single stranded DNA is PAGE purified to ensure that there is tight control on the length of the strand and accuracy of the sequence. In certain embodiments, the sections within the single stranded DNA will not contain more than 200 monomers. In certain embodiments, the sections within the single stranded DNA will not contain more than 100 monomers. In certain embodiments, the entire length of the polymer will be at least long enough to completely fill the nanopore. For example, with the protein pore wild type alpha hemolysin, the polymer is comprised of at least 12 monomers to fill the entire beta barrel of the nanopore during the residual current measurements.

Non-limiting examples of single stranded DNA that can be used to demonstrate the CNR include polyA40C80A40 (SEQ ID NO: 4), polyA20C120A20 (SEQ ID NO: 28), polyA40C120A10 (SEQ ID NO: 29), polyA40GA40 (SEQ ID NO: 23), polyA40G4A10C60 (SEQ ID NO: 30), polyA40G4A40 (SEQ ID NO: 18), polyC40T40C40 (SEQ ID NO: 31), polyT40C40T40 (SEQ ID NO: 32), polyT50G4T50 (SEQ ID NO: 33), polyA20C40A20C40A20 (SEQ ID NO: 34), polyACACACACACACACACACACACACAC (SEQ ID NO: 35), polyA40CA40 (SEQ ID NO: 36), polyA40C2A40 (SEQ ID NO: 37), polyT40CT40 (SEQ ID NO: 38), polyT40C2T40 (SEQ ID NO: 39), polyT40GT40 (SEQ ID NO: 40), polyC40AC40 (SEQ ID NO: 41), polyC40TC40 (SEQ ID NO: 42), polyC40A2C40 (SEQ ID NO: 43), polyC40T2C40 (SEQ ID NO: 44) or any similar strand.

Solution Conditions

The electrolyte used in the nanopore residual current measurements can have some effect on the CNR measured and can significantly affect the rate of translocation of the polymer. Any solution condition generally known can be used to measure the CNR. This includes the non-limiting examples of various salts, buffers, and changes to viscosity, such as adding glycerol. Non-limiting examples of the solutions and conditions that can be used when determining the CNR follow. Non-limiting examples of electrolytes include sodium chloride, potassium chloride, lithium chloride or combinations thereof with concentration ranges from 0.1 to 6 Molar (M) (e.g. 0.1 M, 0.2 M, 0.3 M, 0.4 M, 0.5 M, 1 M, 2 M, 3 M, 4 M, 5 M, or 6 M). In certain embodiments, a buffer is included in the electrolyte solution to stabilize the pH. In certain embodiments, the buffer is 10 mM Tris/1 mM EDTA. In certain embodiments, the pH of the solution ranges from 5 to 9 (e.g. 5, 5.5, 6, 6.5, 7, 7.5, 8.0, 8.5, or 9.0). In certain embodiments, the pH of the solution can range from about 7 to 7.5 (e.g. 7.0, 7.1, 7.2, 7.3, 7.4, 7.5).

DC Voltage Bias

For a DC measurement system, the voltage bias is applied across the pore to produce a measurable current. The voltage bias is held constant for the measurement of the CNR. The voltage bias used in the nanopore residual current measurements can have an effect on the CNR measured. In general, as the bias is increased, the contrast between sections will increase and the average duration per polymer section will decrease.

Non-limiting examples of the bias ranges that can be used to measure the CNR include 20 millivolts (mV) to 300 mV or greater (e.g. 20 mV, 30 mV, 40 mV, 50 mV, 60 mV, 70 mV, 80 mV, 90 mV, 100 mV, 110 mV, 120 mV, 130 mV, 140 mV, 150 mV, 160 mV, 170 mV, 180 mV, 190 mV, 200 mV, 210 mV, 220 mV, 230 mV, 240 mV, 250 mV, 260 mV, 270 mV, 280 mV, 290 mV, 300 mV or greater).

AC Source Signal

In some embodiments, for an AC measurement system, a source signal that is periodic (e.g. sinusoidal or a square wave) is applied and is defined by an applied bias (e.g. an AC bias) and frequency. Non-limiting examples of the applied bias include 50 mV to 1000 mV (e.g. 50 mV, 60 mV, 70 mV, 80 mV, 90 mV, 100 mV, 110 mV, 120 mV, 130 mV, 140 mV, 150 mV, 160 mV, 170 mV, 180 mV, 190 mV, 200 mV, 300 mV, 400 mV, 500 mV, 600 mV, 700 mV, 800 mV, 900 mV, or 1000 mV).

In certain embodiments, non-limiting examples of the frequency can be 10 kHz to 300 kHz or greater (e.g. 10 kHz, 20 kHz, 30 kHz, 40 kHz, 50 kHz, 60 kHz, 70 kHz, 80 kHz, 90 kHz, 100 kHz, 150 kHz, 200 kHz, 250 kHz, 300 kHz or greater).

Translocation Control Methods

There are numerous methods known to control the rate of translocation of a polymer through a nanopore. These include the non-limiting examples of polymerases, exonucleases, single stranded binding proteins, helicases and hybridizing segments of complementary strands of DNA to portions of the single stranded DNA to control the rate of translocation. Any suitable method can be used to test the CNR of a nanopore.

Nanopores

In some embodiments, a nanopore is a protein pore. In some embodiments, a nanopore comprises one or more proteins or polypeptide subunits. In some embodiments a nanopore is an isolated protein. The term "isolated protein" as used herein can mean purified, partially purified, or substantially purified from other proteins or impurities. In some instances, the term "isolated protein" can refer to a recombinant protein in a purified, partially purified, or substantially purified form. In some instances an "isolated protein" as used herein can refer to native protein that is purified, partially purified, or substantially purified from it's native environment. A nanopore may include an isolated pore protein and one or more other components. Non-limiting examples of other components include those that form a vesicle, monolayer and/or bilayer structure (e.g., one or more lipids).

In certain embodiments, a protein pore includes a pore shaped, or shaped in part, by one or more beta barrels. Non-limiting examples of a protein pore include the beta barrel containing transmembrane proteins including the bacterial porins alpha hemolysin (e.g., from *Staphylococcus aureus*), MspA (e.g., from *Mycobacterium smegmatis*), OmpF (*E. coli*), PA63 (*B. anthracis*), and gramicidin A (*B. brevis*). In some embodiments a nanopore comprises a porin protein. In some embodiments a nanopore comprises a hemolysin protein. In some embodiments, a protein pore can be embedded in a lipid bilayer by known methods.

Porin Proteins

Porin proteins are proteins that fall into the beta-barrel class of transmembrane proteins. Porins act as a pore or channel through which molecules can diffuse. Unlike other membrane transport proteins, porins are large enough to allow passive diffusion. Porins typically control the diffusion of small metabolites, like sugars, ions, amino acids and the like. Porins sometimes are chemically selective. A particular porin sometimes transports only one group of molecules, and sometimes a porin is specific for only one molecule.

Porins typically are composed of beta sheets, which in turn, generally are linked together by beta turns on the cytoplasmic side and long loops of amino acids on the other side. The beta sheets lie in an anti-parallel fashion and form a cylindrical tube, called a beta barrel. The amino acid composition of the porin beta sheets is unique in that polar and nonpolar residues alternate along the beta sheets. This arrangement results in a conformation in which most or all of the nonpolar residues typically face outward so as to interact with the nonpolar lipid membrane, and most or all of the polar residues typically face inwards into the center of the beta barrel to interact with the aqueous channel.

Non-limiting examples of porin proteins include, malto-porins and other sugar specific porins (e.g., from gram negative bacteria (e.g., *E. coli, S. typhimurium*, and other bacteria), OmpG porin (e.g., gram negative bacteria), opacity porins (e.g., from *Neisseria* bacteria), nucleoside specific porin (e.g., from *E. coli* and other bacteria), MspA porin (e.g., from *Mycobacterium smegmatis*), and alpha hemolysin (e.g., from *Staphylococcus Aureus*).

Hemolysins and Alpha-Hemolysin

Hemolysins are exotoxins produced by bacteria that cause lysis of red blood cells in vitro or in vivo. Visualization of hemolysis of red blood cells in agar plates facilitates the categorization of some pathogenic bacteria such as *Streptococcus* and *Staphylococcus*. Although the lytic activity of some hemolysins on red blood cells may be important for nutrient acquisition or for causing certain conditions such as anemia, many hemolysin-producing pathogens do not cause significant lysis of red blood cells during infection. Although hemolysins are able to lyse red blood cells in vivo, the ability of hemolysins to target other cells, including white blood cells, often accounts for the effects of hemolysins in the host. Many hemolysins are pore forming proteins.

A non-limiting example of a porin protein useful for insertion into lipid bilayers is alpha-HL, sometimes also referred to as alpha toxin. Alpha-hemolysin (e.g., alpha-HL) forms a heptameric beta-barrel in biological membranes. Alpha-HL is secreted as a monomer that binds to the outer membrane of susceptible cells. Upon binding, the monomers oligomerize to form a water-filled transmembrane channel that facilitates uncontrolled permeation of water, ions, and small organic molecules. Rapid discharge of vital molecules, such as ATP, dissipation of the membrane potential and ionic gradients, and irreversible osmotic swelling leading to rupture or lysis of the cell wall, frequently causing death of the host cell. This pore-forming property has been identified as a major mechanism by which protein toxins cause damage to cells.

Several properties of alpha-HL make this membrane channel suitable for various biotechnological applications: assembled alpha-HL is stable over a wide range of pH and temperature, its transmembrane pore stays open at normal conditions, alpha-HL can insert into to various biological or synthetic lipid bilayers, the insertion proceeds spontaneously and does not require specific ionic conditions. Alpha-HL inserted into a lipid bilayer may prove useful as delivery systems, as a component of a stochastic sensor, and transporters or translocators. Alpha-HL has been shown to have the ability to translocate nucleic acids through the pore formed in a lipid bilayer.

Non-limiting examples of pore forming hemolysins include listeriolysin O (e.g., from *Listeria monocytogenes*), alpha toxin or alpha hemolysin (e.g., from *Staphylococcus aureus*), PVL cytotoxin (e.g., from *Staphylococcus aureus*), and cytolysin A (e.g., from *E. coli*).

Modifications of a Nanopore

In some embodiments, the at least one mutagenesis modification of a nanopore can increase the contrast signal, reduce the total noise value or both. In certain embodiments, the at least one modification increases the CNR.

In some embodiments, the at least one mutagenesis modification to the protein pore can include substituting at least one native amino acid within the protein pore. In some embodiments, the at least one mutagenesis modification to the protein pore can include substituting at least one native amino acid to increase the contrast signal. In some embodiments, the at least one mutagenesis modification to the protein pore can include substituting at least one native amino acid to reduce the total noise value. In certain embodiments, the at least one mutagenesis modification to the protein pore can include substituting at least one native amino acid to increase the CNR. In certain embodiments, the mutagenesis modification can include substituting a native amino acid with a naturally occurring amino acid or a synthetic amino acid. In certain embodiments, the synthetic amino acid can include chemically synthesized amino acids with non-natural side-chains.

In certain embodiments, the protein pore is alpha hemolysin. In some embodiments, alpha hemolysin can include a primary constriction. In some embodiments, the primary constriction includes at least one of the native amino acids E111, M113, K147 and T145. In some embodiments, a nanopore protein can include a secondary constriction. In some embodiments, alpha hemolysin can include a secondary constriction. In some embodiments, the secondary constriction includes at least one of the native amino acids N121, G137, N139, L135, N123, and T125. In some embodiments, a nanopore protein includes an exit region. In some embodiments, alpha hemolysin includes an exit region. The exit region can include at least the native amino acids D127, T129 and K131. In some embodiments, a nanopore protein can include one or more salt bridges. In some embodiments, alpha hemolysin includes one or more salt bridges. In some embodiments, the salt bridge includes a pair of native amino acids E111 and K147 and/or the pair of amino acids D127 and K131.

Modifications

In some embodiments, the at least one modification to an alpha hemolysin pore includes substituting at least one of the native amino acids in a primary constriction in the alpha hemolysin pore to simplify the primary constriction. Non-limiting examples of a substitution to simplify the primary constriction include an amino acid that reduces the charge compared to the native amino acid, an amino acid that eliminates the charge of the side chain of the native amino acid, an amino acid that reduces the hydrogen bonding between the amino acid and the polymer compared to the native amino acid and the polymer, an amino acid that is smaller in size than the native amino acid, and an amino acid that changes the hydrophobic interactions between the amino acid and the DNA. The substitution to simplify the primary constriction can increase the contrast signal, reduce the total noise value or both. In certain embodiments, the substitution to simplify the primary constriction can increase the CNR.

In some embodiments, the at least one modification to the alpha hemolysin pore can include substituting at least one of the native amino acids in a secondary constriction to enhance the secondary constriction. Non-limiting examples of a substitution to enhance a secondary constriction include an amino acid that changes the charge compared to the native amino acid, an amino acid that increases hydrogen bonding between the amino acid and the polymer compared to the native amino acid and the polymer, an amino acid that changes the hydrophobic interactions between the amino acid and the DNA and an amino acid that is larger in size than the native amino acid. In some embodiments, a substitution to enhance a secondary constriction can increase the contrast signal, reduce the total noise value or both. In certain embodiments, the substitution to enhance the secondary constriction can increase the CNR.

In some embodiments, an at least one modification to an alpha hemolysin pore includes substituting at least one of the native amino acids in a salt bridge to a different amino acid to change, disrupt, or move the salt bridge. In certain embodiments, a substitution to a salt bridge is changing one of the native amino acids in a salt bridge to the same charge as the other amino acid in the salt bridge (e.g. changing D127 (negative) to lysine (K, positive), which is the same charge as K131). In certain embodiments, a substitution to a salt bridge is changing one of the native amino acids in a salt bridge to a different amino acid with the same charge (e.g. changing E111 (negative) to aspartic acid (D), which is also negatively charged). In certain embodiments, at least one of the native amino acids is changed to move a salt bridge. In some embodiments, a salt bridge is moved, for example by changing K131 to a neutral amino acid (i.e. no charge) and substituting G133 to a charged amino acid to move the salt bridge. An amino acid substitution that changes, disrupts, or moves a salt bridge can increase the contrast signal, reduce the total noise value or both. In certain embodiments, the substitution to change or disrupt a salt bridge can increase the CNR.

In some embodiments, an at least one modification to an alpha hemolysin pore includes substituting at least one of the native amino acids to add at least one salt bridge to the pore. In certain embodiments, substituting at least one of the native amino acids to add at least one salt bridge can increase the contrast signal, reduce the total noise value or both. In certain embodiments, substituting at least one of the native amino acids to add at least one salt bridge can increase the CNR.

In some embodiments, the at least one modification to the alpha hemolysin pore can include a combination of substitutions to any of the native amino acids within the alpha hemolysin pore. Examples of substitutions that can be introduced include those presented in the following table. These mutated nanopores can be characterized according to methods presented here and incorporated by reference.

TABLE 2

Non-limiting examples of possible mutations that can be made to the alpha hemolysin protein pore.

Protein Nanopore

E111S/M113S/N121D/N123M/L135S/G137K/N139S/T145S/K147S
E111S/M113S/T125N/L135I/T145S/K147S
E111S/M113S/T145S/K147S/L135I
E111D/M113S/N121S/N123S/L135G/N139S
E111D/M113S/N121S/N139S
E111D/M113S/N121S/N123S/L135G/N139S
E111D/M113S/N121S/N123S/L135I/N139S
E111S/M113S/T145S/K147S/L135I/D127K
E111S/M113S/T145S/K147S/N121S/N139S

The amino acid sequence for wild type alpha hemolysin is provided for reference below:

SEQ ID NO. 1
MADSDINIKTGTTDIGSNTTVKTGDLVTYDKENGMHKKVFYSFIDDKNH

NKKLLVIRTKGTIAGQYRVYSEEGANKSGLAWPSAFKVQLQLPDNEVAQ

ISDYYPRNSIDTKEYMSTLTYGFNGNVTGDDTGKIGGLIGANVSIGHTL

KYVQPDFKTILESPTDKKVGWKVIFNNMVNQNWGPYDRDSWNPVYGNQL

FMKTRNGSMKAADNFLDPNKASSLLSSGFSPDFATVITMDRKASKQQTN

IDVIYERVRDDYQLHWTSTNWKGTNTKDKWTDRSSERYKIDWEKEEMTN

Nanopore Devices

In some embodiments, provided is a device or apparatus that includes a high CNR nanopore. Any suitable device capable of supporting a high CNR nanopore and allowing for sensing of an analyte can be utilized. In some embodiments, nanopore devices comprise a substrate that includes an aperture and one or more nanopore protein pores inserted in the aperture. In certain embodiments, the protein pore is inserted in a lipid monolayer and/or bilayer that traverses the aperture, and in some embodiments, the nanopore protein is retained within the aperture without a lipid monolayer and/or bilayer. In some embodiments, a substrate includes a well and one or more nanopore proteins inserted in the well opening within a lipid monolayer and/or bilayer that traverses the well opening. In certain embodiments, a substrate includes a well and one or more nanopore proteins inserted in the well opening without a lipid monolayer and/or bilayer that traverses the well opening.

In certain embodiments, the apparatus further comprises a DC measurement system. In some embodiments, the apparatus further comprises an AC measurement system. In certain embodiments, the apparatus further comprises an AC/DC measurement system.

In some embodiments, the substrate comprises glass, Si, $SiO_2$, $Si_3N_4$, alumina, nitrides, diamond, quartz, sapphire metals, ceramics, alumino-silicate, polymers (e.g., Teflon, polycarbonate), the like or combinations thereof. Non-limiting examples of glass types suitable for a substrate include fused silica glass, ninety-six percent silica glass, soda-lime silica glass, borosilicate glass, aluminosilicate glass, lead glass, doped glass comprising desired additives, functionalized glass comprising desired reactive groups, the like and combinations thereof. Non-limiting examples of minerals (e.g., quartz) suitable for a substrate include quartz, tridymite, cristobalite, coesite, lechatelierite, stishovite, the like and combinations thereof. The substrate can be manufactured from a pure substance or can be manufactured from a composite material.

In some embodiments the thickness of a substrate typically ranges from about 100 nanometer (nm) to 5 millimeters (mm) in thickness (e.g., about 100 nm, about 150 nm, about 200 nm, about 250 nm, about 300 nm, about 350 nm, about 400 nm, about 500 nm, about 600 nm, about 700 nm, about 800 nm, about 900 nm, about 1000 nm (e.g., about 1 µm), about 2 µm, about 3 µm, about 4 µm, about 5 µm, about 6 µm, about 7 µm, about 8 µm, about 9 µm, about 10 µm, about 15 µm, about 20 µm, about 25 µm, about 30 µm, about 35 µm, about 40 µm, about 45 µm, about 50 µm, about 60 µm, about 70 µm, about 80 µm, about 90 µm, 100 µm, about 110 µm, about 120 µm, about 130 µm, about 140 µm, about 150 µm, about 175 µm, about 200 µm, about 225 µm, about 250 µm, about 300 µm, about 350 µm, about 400 µm, about 450 µm, about 500 µm, about 600 µm, about 700 µm, about 800 µm, about 900 µm, 1000 µm (e.g. 1 mm), about 2 mm, about 3 mm, about, about 4 mm, or about 5 mm).

In certain embodiments, a substrate contains an aperture that separates two fluid reservoirs. In some embodiments, the aperture is a micron scale aperture, and sometimes the aperture is a nanoscale aperture. In some embodiments, the aperture is in a glass or quartz substrate. In certain embodiments, the aperture has a diameter of about 0.25 nanometer to about 50 µm (e.g., about 0.25 nanometers, about 0.5 nanometers, about 1 nanometer, about 1.5 nanometers, about 2 nanometers, about 2.5 nanometers, about 3 nanometers, about 3.5 nanometers, about 4 nanometers, about 4.5 nanometers, about 5 nanometers, about 6 nanometers, about 7 nanometers, about 8 nanometers, about 9 nanometers, about 10 nanometers, about 15 nanometers, about 20 nanometers, about 25 nanometers, about 30 nanometers, about 35 nanometers, about 40 nanometers, about 45 nanometers, about 50 nanometers, about 60 nanometers, about 70 nanometers, about 80 nanometers, about 90 nanometers, about 100 nanometers, about 125 nanometers, about 150 nanometers, about 175 nanometers, about 200 nanometers, about 250 nanometers, about 300 nanometers, about 350 nanometers, about 350 nanometers, about 400 nanometers, about 500 nanometers, about 600 nanometers, about 700 nanometers, about 800 nanometers, about 900 nanometers, about 1000 nanometers (e.g., 1 µm), about 2 µms, about 3 µm, about 4 µm, about 5 µm, about 10 µm, about 15 µm, about 20 µm, about 25 µm, about 30 µm, about 35 µm, about 40 µm, about 45 µm, or about 50 µm).

In certain embodiments, a substrate comprises a well. In some embodiments, the well has an aperture formed by the well opening with a diameter of about 100 nanometers to about 100 µm (e.g., about 100 nanometers, about 125 nanometers, about 150 nanometers, about 175 nanometers, about 200 nanometers, about 250 nanometers, about 300 nanometers, about 350 nanometers, about 350 nanometers, about 400 nanometers, about 500 nanometers, about 600 nanometers, about 700 nanometers, about 800 nanometers, about 900 nanometers, about 1000 nanometers (e.g., 1 µm), about 2 µms, about 3 µm, about 4 µm, about 5 µm, about 10 µm, about 15 µm, about 20 µm, about 25 µm, about 30 µm, about 35 µm, about 40 µm, about 45 µm, about 50 µm, about 60 µm, about 70 µm, about 80 µm, about 90 µm or about 100 µm).

The channel formed by an aperture in a substrate can be of any suitable geometry, and sometimes has a substantially circular, oval, square, rectangular, rhomboid, parallelogram, or other like cross-section. The channel in the substrate can be of any suitable profile, and sometimes has a substantially cylindrical or conical (e.g., tapering or expanding conical) profile.

A substrate sometimes comprises a coating that modifies the surface of an aperture or well structure. In some embodiments, a substrate comprises a surface that includes a hydrophobic substance. In certain embodiments, a substrate comprises a surface that includes a hydrophilic substance. In some embodiments, a substrate comprises a surface that includes hydrophobic and hydrophilic substances.

Thus, one or more portions of, or the entire, substrate can be treated or coated to adopt certain desirable characteristics, in some embodiments. In certain embodiments, the treatment or coating enhances formation of lipid structures across the aperture of the substrate. Physical and/or chemical modification of the surface properties of a substrate include, but are not limited to, modification of the electrical charge density, changes to the hydrophobicity, changes to the hydrophilicity, the like and combinations thereof. Any suitable substance can be utilized to modify one or more interior and/or exterior surfaces of the substrate. Non-limiting examples of suitable materials for modification of one or more substrate surfaces include silanes, silanes terminating in a cyano group, silanes terminating in a methyl group, thiols, the like, or combinations thereof. In some embodiments, an exterior surface of a substrate may be modified by a first entity. In certain embodiments, an interior surface of a substrate may be modified by a second entity. In some embodiments, the first and the second entity may be the same entities, and in certain embodiments, the first and the second entity may be different entities. In some embodiments utilizing a glass substrate, the first or second entities that can be used to modify the interior or exterior surfaces of a substrate include a variety of glass-reactive species, e.g., 3-cyano-propyldimethylchlorosilane, that react with the silanol groups of the glass surface. In some embodiments, a device comprises a lipid composition (e.g., monolayer, bilayer, combination thereof) over, across or spanning an aperture of a substrate. A lipid composition sometimes comprises a lipid monolayer, sometimes comprises a lipid bilayer, and in some embodiments comprises a lipid layer that partially is a monolayer and partially is a bilayer. In some devices comprising both monolayer and bilayer lipid structures, solvent may be trapped at a location (i.e., annulus) between the substrate and the lipid layer at or near the monolayer and bilayer interface, which is addressed in greater detail hereafter.

The lipid composition of a device often is relatively stable to mechanical disturbances, and can have a lifetime in excess of two weeks. Additionally, a device can be made with a lipid composition that is readily formed over or in an aperture and has a relatively small surface area, which can give rise to favorable electrical characteristics.

In some embodiments, lipids, having various chain lengths or various structures of polar heads, can be used to form various structures suitable for use with a device. For example, a monolayer, bilayer, or a combination of monolayer or bilayer can be formed on one or more exterior and/or interior surfaces of a substrate. In certain embodiments, a lipid composition that spans across the substrate aperture is a combination of a lipid bilayer and monolayer. In various embodiments, a lipid monolayer deposited on the exterior surface of a substrate and a lipid monolayer deposited on the interior surface of the nanopore that join together at about the edge of the nanopore opening can form a lipid bilayer spanning or suspended across the aperture. The bilayer formed across an aperture sometimes is referred to as a "spanning lipid bilayer" herein.

In a spanning bilayer structure, a bilayer often is present across the substrate aperture and a monolayer is present on substrate surfaces (e.g., chemically modified surfaces). In some embodiments, a chemically modified device corrals a single protein pore in the lipid bilayer region that spans across the aperture. An inserted protein (e.g., protein pore, alpha hemolysin) often is able to diffuse in the bilayer across the aperture but often cannot leave this area to enter the lipid monolayer. Insertion of a sensing entity (e.g., protein pore) often occurs only in the bilayer region. A thin layer (e.g., about 1 to about 10 nm thick) containing solvent and ions sometimes is formed between a spanning lipid bilayer and one or more surfaces of the substrate. The thickness of this layer is defined as the distance between the exterior surface and the lipid bilayer and often plays a role in determining the resistance of the bilayer seal and the stability and fluidity of the bilayer. A spanning bilayer also sometimes includes an annulus formed between monolayers and a nanopore surface, which can contain solvent (e.g., FIG. 15 of U.S. Pat. No. 7,777,505).

While a device often comprises a lipid composition traversing a substrate aperture, this composition may comprise any suitable amphiphilic materials into which a protein can be incorporated. A protein often is inserted into a structure (e.g., monolayer and/or bilayer) formed by the lipid or amphiphilic material composition. A protein that is inserted into the structure can be water soluble, detergent-solubilized or incorporated into a lipid vesicle, liposome or micelle in some embodiments.

An amphiphilic molecule generally is composed of a hydrophobic part and a polar part. The terms "amphiphilic material" or "amphiphilic materials" refer to materials made of molecules having a polar, water-soluble group attached to a nonpolar, water-insoluble hydrocarbon chain. Amphiphilic materials sometimes can be polymers. The amphiphilic materials may be a pure substance or a mixture of different amphiphilic materials. The polymeric materials may be a polymer with a uniform molecular weight distribution, or a polymer with a non-uniform molecular weight distribution, or a mixture of polymers which comprise different monomers. Non-limiting examples of amphiphilic molecules include lipids, detergents, surfactants, proteins, polysaccharides, and other chemical or biochemical materials that can be rendered amphiphilic. The terms "detergent" or "detergents" as used herein refer to a surfactant or a mixture of surfactants. The terms "surfactant" or "surfactants" as used herein refers to any compound that (i) lowers the surface tension of a liquid, allowing easier spreading, and/or (ii) lowers the interfacial tension between two liquids, or between a liquid and a solid. Surfactants may act as: detergents, wetting agents, emulsifiers, foaming agents, and dispersants. Surfactants often are categorized as ionic (anionic or cationic), zwitterionic or amphoteric, or non-ionic. Non-limiting examples of surfactants include ammonium lauryl sulfate, sodium lauryl sulfate (SDS), sodium laureth sulfate (e.g., also known as sodium lauryl ether sulfate (SLES)), sodium myreth sulfate, dioctyl sodium sulfosuccinate, perfluorooctanesulfonate (PFOS), perfluorobutanesulfonate, alkyl benzene sulfonates, alkyl aryl ether phosphate, alkyl ether phosphate, fatty acid salts (e.g., soaps), sodium stearate, sodium lauroyl sarcosinate, perfluorononanoate, perfluorooctanoate, octenidine dihydrochloride, cetyl trimethylammonium bromide (CTAB), cetyl trimethylammonium chloride (CTAC), Cetylpyridinium chloride (CPC), polyethoxylated tallow amine (POEA), benzalkonium chloride (BAC), benzethonium chloride (BZT); 5-Bromo-5-nitro-1,3-dioxane, dimethyldioctadecylammonium chloride, dioctadecyldimethylammonium bromide, 3-[(3-Cholamidopropyl)dimethylammonio]-1-propanesulfonate (e.g., CHAPS), cocamidopropyl hydroxysultaine, amino acids, imino acids, cocamidopropyl betaine, lecithin, fatty alcohols (e.g., cetyl alcohol, stearyl alcohol, and the like), the like and combinations thereof.

A lipid molecule typically comprises at least one hydrophobic chain and at least one polar head. When exposed to an aqueous environment, lipids often will self assemble into structures that minimize the surface area exposed to a polar (e.g., aqueous) medium. Lipids sometimes assemble into structures having a single or monolayer of lipid enclosing a non-aqueous environment, and lipids sometimes assemble into structures comprising a bilayer enclosing an aqueous environment. In a monolayer structure, the polar portion of lipids (e.g., the head of the molecule in the case of phospholipids and other lipids commonly found in cell substrates) often is oriented towards the polar, aqueous environment, allowing the non-polar portion of the lipid to contact the non-polar environment.

A lipid bilayer typically comprises a sheet of lipids, generally two molecules thick, arranged so the hydrophilic phosphate heads point towards a hydrophilic aqueous environment on either side of the bilayer and the hydrophobic tails point towards the hydrophobic core of the bilayer. This arrangement results in two "leaflets" that are each a single molecular layer. Lipids self-assemble into a bilayer structure due to the hydrophobic effect, which creates an energetically unfavorable interaction between the hydrophobic lipid tails and the surrounding water. Lipid bilayers typically are held together entirely by non-covalent forces that do not involve formation of chemical bonds between individual molecules. Lipid bilayers generally also are impermeable to ions, which allow cells to regulate various processes that involve salt concentrations or gradients and intracellular pH by pumping ions across cell substrates using ion transport mechanisms.

In some embodiments, lipid bilayers are natural, and in certain embodiments lipid bilayers are artificially generated. Natural bilayers often are made mostly of phospholipids, which have a hydrophilic head and two hydrophobic tails, and form a two-layered sheet as noted above, when exposed to water or an aqueous environment. The center of this bilayer contains almost no water and also excludes molecules like sugars or salts that dissolve in water, but not in oil. Artificial bilayers (e.g., sometimes also referred to as "model lipid bilayers") are any bilayers assembled through artificial means, as opposed to bilayers that occur naturally (e.g., cell substrates, lipid bilayers that cover various subcellular structures). An artificial bilayer can be made with synthetic and/or natural lipids, thus the process, not the material, defines an artificial or model system. The simplest model systems contain only a single pure synthetic lipid. The artificial bilayer also may contain a hydrophobic solvent, such as decane, hexadecane, pentane or other solvents and combinations thereof, that is used to disperse the lipid during bilayer formation and stabilize the formation of lipid bilayers across apertures in hydrophobic materials. The simplicity of a single lipid system is advantageous when determining physical or mechanical properties of bilayers. Model bilayers with greater physiological relevance can be generated utilizing mixtures of several synthetic lipids or, as mentioned, with natural lipids extracted from biological samples.

The presence of certain lipids or proteins sometimes can alter the surface chemistry of bilayers (e.g., viscosity or fluidity of lipid bilayers). Phospholipids with certain head groups can alter the surface chemistry of a bilayer. Non-limiting examples of substrate constituents that can alter the surface chemistry of bilayers include fats, lecithin, cholesterol, proteins, phospholipids (e.g., phosphatidic acid (phosphatidate), phosphatidylethanolamine (e.g., cephalin), phosphatidylcholine (e.g., lecithin), phosphatidylserine, and phosphoinositides such as phosphatidylinositol (PI), phosphatidylinositol phosphate (PIP), phosphatidylinositol bisphosphate (PIP2) and phosphatidylinositol triphosphate (PIP3), phosphatidylglycerol, ceramide phosphorylcholine, ceramide phosphorylethanolamine, ceramide phosphorylglycerol), surfactants, the like and combinations thereof.

Lipid tails also can affect lipid composition properties, by determining the phase of the bilayers, for example. A bilayer sometimes adopts a solid gel phase state at lower temperatures and undergoes a phase transition to a fluid state at higher temperatures. The packing of lipids within a bilayer also affects its mechanical properties, including its resistance to stretching and bending. Properties, such as stretching, bending or temperature induced phase transitions, have been studied with artificial "model" bilayers.

A device may include one or more types of molecules other than phospholipids. For example, cholesterol, which helps strengthen bilayers and decreases bilayer permeability can be included. Cholesterol also helps regulate the activity of certain integral substrate proteins. Different types or forms of lipid compositions (e.g., monolayers and/or bilayers) can be found naturally or generated artificially. Non-limiting examples of lipid compositions include monolayers (e.g., micelles) and bilayers including "black PLBs", vesicles (e.g., sometimes referred to as "liposomes"), supported lipid bilayers, linear lipid bilayers and the like.

Membrane proteins typically cannot be incorporated directly into the PLB during formation because immersion in an organic solvent would denature the protein. However, notable exceptions include alpha hemolysin, MspA, and gramicidin. Instead, the membrane protein often is solubilized with a detergent and added to the aqueous solution after the bilayer is formed. The dilution of the detergent stabilizing the protein forces the proteins to spontaneously insert into the bilayer over a period of minutes or hours, and often at a low frequency of success.

A vesicle is a lipid bilayer configured as a spherical shell enclosing a small amount of water or aqueous solution and separating it from the water or aqueous solution outside the vesicle. Because of the fundamental similarity to a cell substrate, vesicles have been used to study the properties of lipid bilayers. Vesicles also are relatively easy to make, adding to their attractiveness as an experimental system. A sample of dehydrated lipid spontaneously forms vesicles, when exposed to water. Spontaneously formed vesicles can be either unilamelar (single-walled) or multilamellar (many-walled) and are of a wide range of sizes from tens of nanometers to several micrometers.

A liposome is an artificially prepared vesicle, and also comprises a lipid bilayer, unlike micelles which comprise a lipid monolayer. Liposomes also can be made of naturally occurring or synthetic lipids, including phospholipids. There are four types of liposomes: MLV (multilamellar vesicles), SUV (Small Unilamellar Vesicles), LUV (Large Unilamellar Vesicles) and GUV (Giant Unilamellar Vesicles). Liposomes may also be used to form PLBs on a surface or across apertures.

Unlike a vesicle or a cell substrate in which the lipid bilayer forms an enclosed shell, a supported bilayer (e.g., SLB) is a planar structure in contact with a substrate. One advantage of the supported bilayer is its stability. SLBs often remain largely intact even when subject to high flow rates or vibration, and the presence of holes will not destroy the entire bilayer. Due to the stability of SLB's, experiments lasting weeks and even months can be conducted with supported bilayers, while BLM experiments sometimes are limited to hours. Another advantage of the supported bilayer is the greater number of methods and tools useable for characterization. In certain embodiments, a substrate may comprise a hydrophilic material, such as untreated glass, or it may be modified in a manner that renders one or more surfaces of the substrate (e.g., pore interior, pore exterior) hydrophilic (e.g. mildly hydrophilic, substantially hydrophilic). In certain embodiments, the bilayer is then formed over the hydrophilic surface and covers across the substrate aperture.

In certain embodiments, a substrate may include a hydrophobic material, such as Teflon, or it may be modified in a manner that renders one or more surfaces of the substrate (e.g., substrate channel interior, substrate channel exterior) hydrophobic (e.g. mildly hydrophobic, substantially hydrophobic). In some embodiments one or more surfaces of a substrate are coated with a hydrophobic substance, including without limitation an alkyl silane substance (e.g., 3-cyanopropyldimethylchlorosilane). Any suitable silane substance can be selected to render a substrate surface more hydrophobic and support interaction with lipids for formation of a lipid structure that spans the substrate aperture. In some embodiments, a spanning lipid structure contains a monolayer that interacts with an exterior surface of a substrate and a monolayer that interacts with an interior surface of the substrate, where the monolayers join together at about the edge of the opening of the aperture and form a lipid bilayer spanning the substrate aperture (e.g., U.S. Pat. No. 7,777,505, entitled "Nanopore platforms for ion channel recordings and single molecule detection and analysis," naming White et al. as inventors).

In certain embodiments, a nanopore apparatus comprises a Nanopore Membrane System as described in U.S. patent application Ser. No. 13/414,636 filed on Mar. 7, 2012, entitled "METHODS FOR VOLTAGE-INDUCED PROTEIN INCORPORATION INTO PLANAR LIPID BILAYERS," naming Ryan Dunnam et al. as inventors, the entirety of which herein is incorporated by reference, including all text, tables and drawings.

Methods of Use

A high CNR nanopore can be used in a polymer sequencing system or device to identify and/or sequence a polymer. A method for determining the sequence of a polymer, in some embodiments, comprises contacting a polymer with a device that comprises a high CNR nanopore. In certain embodiments, this method further comprises measuring the residual current of the nanopore under conditions in which the polymer translocates the nanopore. In certain embodiments, the conditions are the test conditions described above for measuring the CNR of a nanopore. In certain embodiments, the rate of translocation of a polymer is controlled. Non limiting examples of a method of controlling the rate of translocation of a polymer include adding one or more of the following to a nanopore device; a polymerase, an exonuclease, a single stranded binding protein, a helicase and/or a hybridizing segment of nucleic acid polymer (e.g. an oligonucleotide). In certain embodiments, the translocation rate of a polymer section that results from changing the translocation rate of a polymer is an average duration that is greater than 1 ms per section. In some embodiments a high CNR nanopore device comprises a method of controlling the rate of translocation of a polymer. In some embodiments a high CNR nanopore device comprises a method of controlling or slowing the rate of translocation of a polymer to a duration time of 1 ms or longer per section.

In certain embodiments, the sequence of all or part of the polymer is identified by identifying the discrete levels within the residual current measurement. In certain embodiments, the residual current of the polymer is measured one time. In certain embodiments, the residual current of the polymer is measured more than one time. In certain embodiments, known data analysis techniques are used to correlate the discrete levels to the sequence of the polymer.

EXAMPLES

The following Examples illustrate but do not limit the technology described herein.

Example 1: Materials and Methods

Provided hereafter are materials methods that can be utilized to construct nanopores characterized as exhibiting high CNR.

Apparatus

Glass nanopore membranes (GNMs) (as described in U.S. Pat. No. 7,777,505) were fabricated from soda lime glass or quartz as described by Zhang (B. Zhang, J. Galusha, P. G. Shiozawa et al., "Bench-Top Method for Fabricating Glass-Sealed Nanodisk Electrodes, Glass Nanopore Electrodes, and Glass Nanopore Membranes of Controlled Size," *Anal. Chem.*, vol. 79, no. 13, pp. 4778-4787, 2007) with radii between 500 nm and 1000 nm. The interior of the GNM was filled with an electrolyte solution of 3 M NaCl, 10 mM Tris, 1 mM EDTA and pH 7.1 and was inserted horizontally through the wall of a polycarbonate cell into a fluid reservoir. A Ag/AgCl electrode was produced by treating a 0.25 mm silver wire with household bleach and was placed interior to the GNM. A pipette holder provided a secure mounting for the GNM and Ag/AgCl electrode interior to the GNM, and a means of maintaining a constant back pressure from 0 to 200 mmHg on the GNM. The test cell had a reservoir of 250 microliters and inlet/outlet ports connected to syringes to allow for raising and lowering the fluid level in the reservoir. A second Ag/AgCl sintered disk electrode served as the reference electrode and was located in the test cell reservoir. The test cell reservoir was defined as the cis side and the interior of the GNM is the trans side.

The GNM electrode and reference electrode were connected to a custom resistive feedback headstage (F. J. Sigworth, "Design of the Patch Clamp," *Single-channel recording*, B. Sakmann and E. Neher, eds., pp. 3-35, New York: Plenum Press, 1995) that allows for applying a voltage bias between the electrodes and provides a low noise readout of the current between the two electrodes. The readout amplifier employed a feedback composed of a 10 GΩ resistor in parallel with a capacitance of approximately 1 pF. All voltages were referenced with respect to the electrode in the GNM. For example, a negative bias indicated that the test cell reservoir electrode was at a negative potential with respect to the electrode interior to the GNM.

DC System Parameters

For the DC system, the output voltage of the amplifier was digitized at a rate of 1.25 MHz using a PCI-6251 DAQ card (National Instruments) in a personal computer (Dell). The resulting data was filtered using an 8-pole Bessel filter at 100 kHz, the effective bandwidth, and down sampled to 500 kHz, the sampling frequency. A final digital differentiation step then converted the filtered signal to the current between the electrodes. The same PCI card was used to provide control of the voltage bias across the two electrodes. A custom LabView application handled voltage control, data acquisition, and simple signal processing such as filtering and conversion to current.

AC/DC System Parameters

For the AC/DC measurements, a sinusoidal source signal of 150 mV and a frequency of 50 kHz was applied. The AC signal was low pass filtered using a 1-pole analog filter for anti-aliasing with a cutoff frequency of 175 kHz. The data was then digitally acquired at an acquisition frequency of 800 kHz. The data was then demodulated using the source signal to produce the effective DC measurements of the residual currents at a sampling frequency of 50 kHz (equal to the source frequency). The data was then digitally low pass filtered using an 8-pole Bessel filter to 10 kHz. The CNR was then computed at a set filter frequency of 10 kHz.

Bilayer Formation 1,2-diphytanoyl-sn-glycero-3-phosphocholine (DPhPC) was diluted in decane to a concentration of 5 milligrams/milliliter. A small (<0.5 microliters) drop of the lipid/decane mixture was added to the surface of electrolyte. The fluid level in the test cell reservoir was lowered below the face of the GNM and then raised above the face of the GNM. This action typically resulted in a bilayer, although in some cases additional lipid was added and the raising and lowering repeated. The bilayer formation method was detailed in U.S. patent application Ser. No. 12/325,792 and is herein incorporated by reference.

Alpha Hemolysin Protein Pore Preparation and Incorporation

Alpha hemolysin protein monomers were generated through coupled in vitro transcription and translation (IVTT) using a bacterial extract kit and then assembled into homo-heptamers on rabbit red blood cell membranes (rRBCM) based on established protocols (B. Walker, and H. Bayley, "Key Residues for Membrane Binding, Oligomerization, and Pore Forming Activity of Staphylococcal alpha-Hemolysin Identified by Cysteine Scanning Mutagenesis and Targeted Chemical Modification," *J. Biol. Chem.*, vol. 270, no. 39, pp. 23065-23071, Sep. 29, 1995, 1995). Plasmid DNA (>95% supercoiled) of wild type and mutant alpha hemolysin were made by GenScript. For most IVTT reactions, 4 micrograms of the DNA were mixed with contents of the kit according to the manufacturer's recommendation and supplemented with a mixture of a complete set of amino acids and 4 microCi of $S^{35}$-Methionine (American Radiolabeled Chemicals). The mixture was incubated at 37° C. for one hour, then mixed with rRBCM and further incubated for three hours. At the end of the incubation period, membranes were washed twice with MOPS buffer followed by solubilization with SDS loading buffer. The latter was loaded onto a 5% polyacrylamide gel and proteins separated by applying a 60 V voltage overnight at room temperature. Gels were dried under vacuum at 60° C. for 3-4 hours and exposed to X-ray film (Kodak) overnight at −80° C. Gels were developed manually using Kodak Development and Wash solutions. Bands corresponding to alpha hemolysin can be observed on the developed film due to the incorporation of the radioactive Methioine. The film was used as a template to cut out a portion of the dried gel containing the alpha hemolysin protein. Proteins were recovered from this portion by overnight electro-elution using an Elutrap Electro-elution system and concentrated down to a volume of 10-20 microliters using microfuge concentrators. Proteins were stored at −80° C. until use.

Alpha hemolysin incorporation in the bilayer was achieved by applying a back pressure (10-200 mmHg) to the interior of the GNM relative to the test cell reservoir. The precise pressure applied was determined by measuring the pressure at which the bilayer fails and using a pressure ~10 mmHg lower. After a single alpha hemolysin protein pore was incorporated as determined by a large jump in conducted current, the pressure was reduced to maintain a single protein insertion. This holding pressure was determined by measuring the pressure at which alpha hemolysin was forced out of the bilayer. In some cases, the protein concentration was too low to allow for incorporation by applying a back pressure alone. In this case a high bias (>200 mV) was applied across the bilayer to promote protein insertion, as described in U.S. patent application Ser. No. 13/414,636, herein incorporated by reference.

For the following Examples 2, 3 and 4, the nanopores were modified alpha hemolysin proteins.

For Example 2 (using the DC measurement system), the modified protein was M113S/E111S/K147S/T145S/L135I, termed the 4SL135I in this application. This nanopore includes five mutagenesis modifications. The native amino acids M113, E111, K147 and T145 were all modified to serine (S) to simplify the primary constriction. The L135 native amino acid was modified to isoleucine (I) to enhance the secondary constriction.

For Example 3 (using the AC/DC measurement system), the modified protein was M113S/E111S/K147S/T145S/L135I/D127K, termed the 4SL135I-D127K in this application. The native amino acids M113, E111, K147 and T145 were all modified to serine (S) to simplify the primary constriction. The L135 native amino acid was modified to isoleucine (I) to enhance the secondary constriction. The D127 native amino acid (negatively charged) was modified to lysine (K, positively charged) to change one of the salt bridges within the pore.

For Example 4 (using the AC/DC measurement system), the modified protein was M113S/E111S/K147S/T145S/N121S/N139S, termed the 4S-N121S-N139S in this application. The native amino acids M113, E111, K147 and T145 were all modified to serine (S) to simplify the primary constriction. The native amino acids N121 and N139 were both modified to serine (S) to enhance the secondary constriction.

Example 2: 4SL135I Analyzed by DC System

Oligonucleotides and Measurement

The single stranded DNA homopolymers, polyA100 (SEQ ID NO: 2) and polyC100 (SEQ ID NO: 3), and the heteropolymer polyA40C80A40 (SEQ ID NO: 4) (GeneLink) were PAGE purified and delivered in a 10 mM Tris, 1 mM EDTA solution buffered to pH 8.5 at a concentration of 100 microMolar. These solutions were stored at −80° C. For measurements of single stranded DNA translocation, approximately 10.0 microliters of the DNA stock solution was added to the ~250 microliter test cell well, yielding a concentration of approximately 4 microMolar. Experiments were run with the polyA100 (SEQ ID NO: 2) and polyC100 (SEQ ID NO: 3) in the same experiment with the 4SL135I protein and separately with the polyA40C80A40 (SEQ ID NO: 4) with the 4SL135I protein. The homopolymers were measured to be able to correlate the discrete levels within the heteropolymer (polyA40C80A40 (SEQ ID NO: 4)) to the actual composition of the sections of the polymer.

Once a 4SL135I insertion was obtained and homopolymer events were observed, data was acquired at 20° C. for approximately 30 minutes. Another experiment was then setup with a single 4SL135I insertion and heteropolymer events were recorded at 20° C. for approximately 30 minutes. The effective bandwidth for the data for both experiments was 100 kHz.

Homopolymer Measurements (polyA100 (SEQ ID NO: 2) and polyC100 (SEQ ID NO: 3))

Figure 1B:
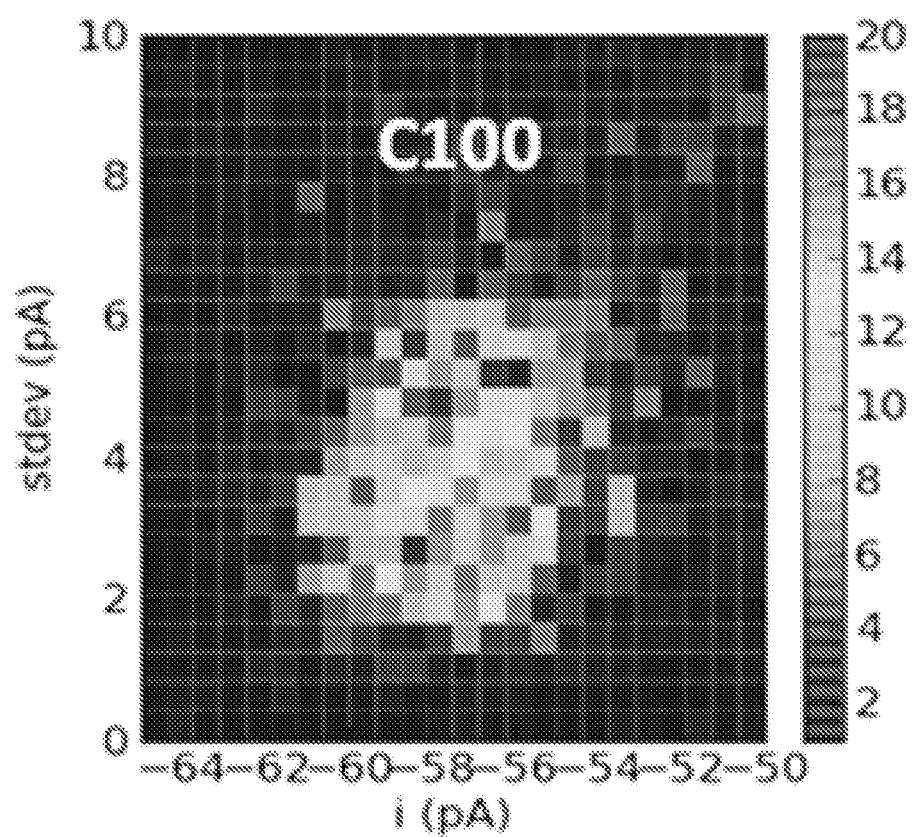
FIG. 1B shows the joint probability density plot of the amplitude and the noise at 10 kHz for polyC100 (SEQ ID NO: 3).
Figure 1C:
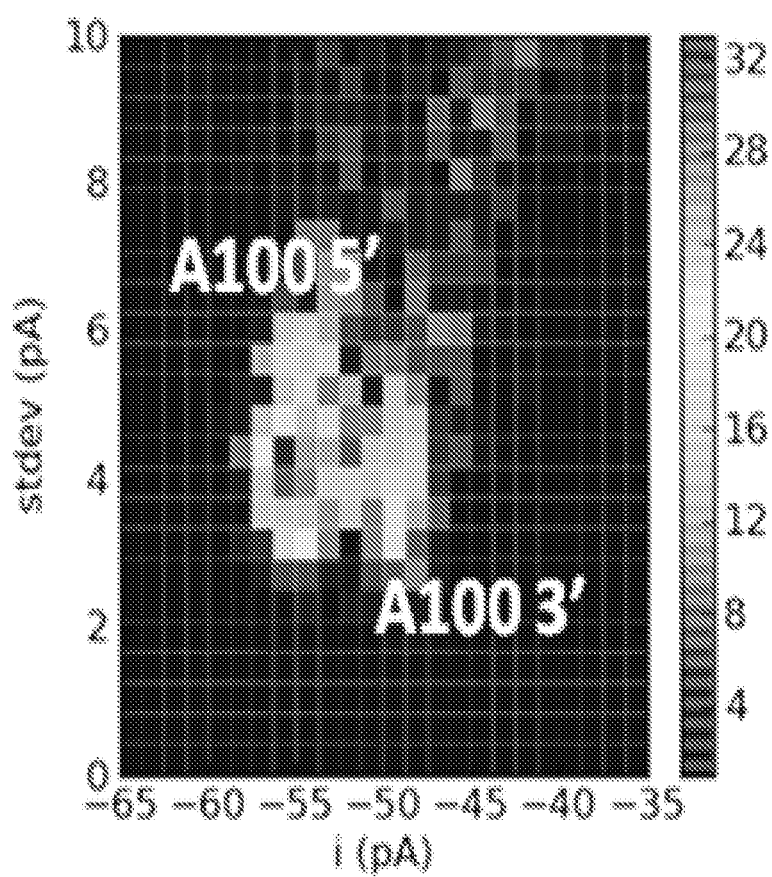
FIG. 1C shows the joint probability density plot of the amplitude and the noise at 10 kHz for polyA100 (SEQ ID NO: 2) 3' and 5'.

The residual current measurements for 1432 polyA100 (SEQ ID NO: 2) events (3' end entering the nanopore first) and 1330 polyC100 (SEQ ID NO: 3) events were recorded (FIG. 1). The orientation of the polyC100 (SEQ ID NO: 3) polymer could not be determined due to a lack of separation by duration or amplitude. The average residual current measurement for polyA100 (SEQ ID NO: 2) over those events at the effective bandwidth of 100 kHz was approximately −49.4 pA (FIG. 1C) and for polyC100 (SEQ ID NO: 3) it was approximately −58.5 pA (FIG. 1B). These values for polyA100 (SEQ ID NO: 2) and polyC100 (SEQ ID NO: 3) were estimated from joint probability density plots of the amplitude and the noise at a 10 kHz bandwidth (e.g. set filter frequency) as shown in FIG. 1B and FIG. 1C. This yielded an absolute difference between polyA100 (SEQ ID NO: 2) and polyC100 (SEQ ID NO: 3) of 9.1 pA.

Figure 2:
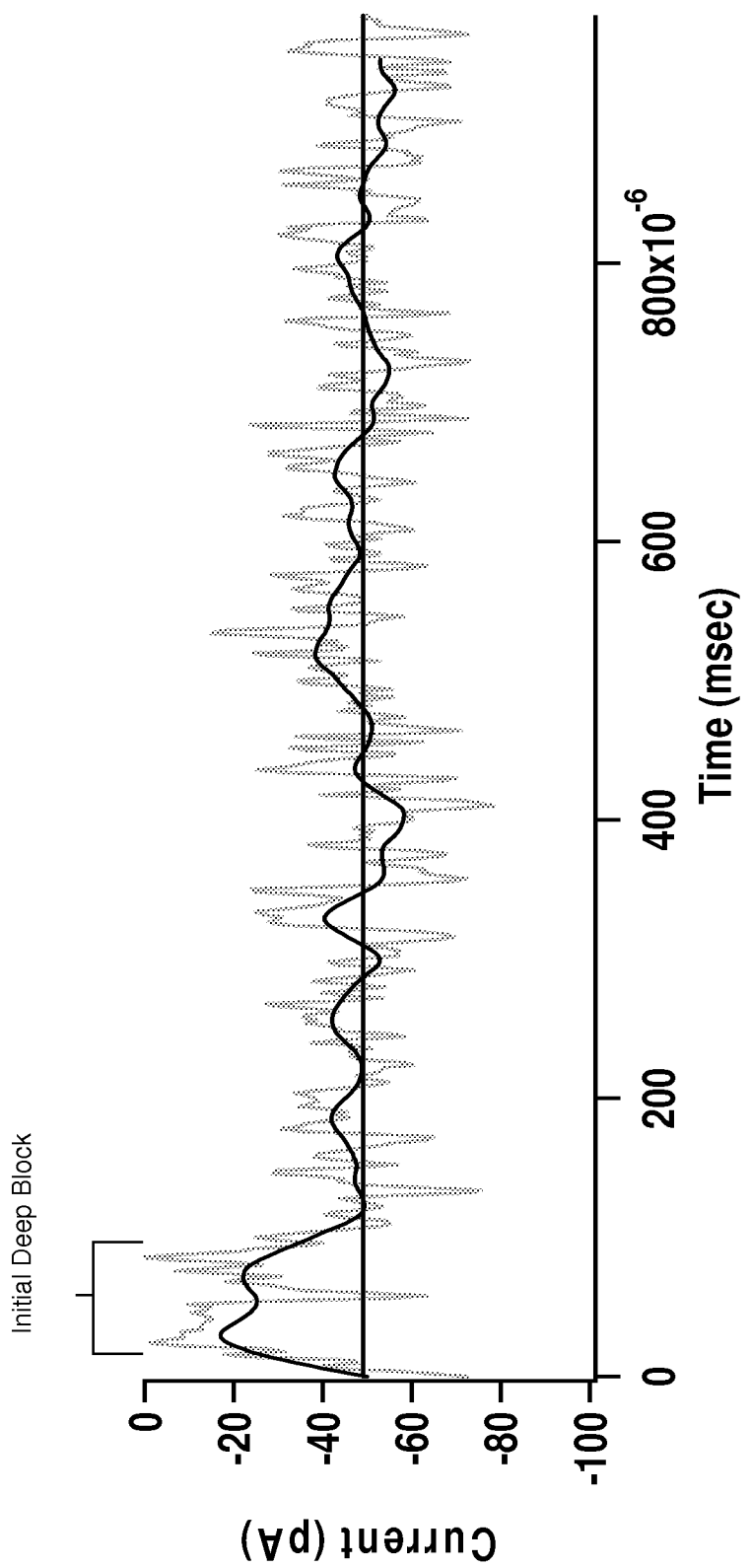
FIG. 2 shows a representative event of polyA100 (SEQ ID NO: 2) 3' translocating the 4SL135I nanopore.

The polyA100 (SEQ ID NO: 2) events showed one of the previously discussed artifacts that can be seen in the data. At the beginning of the majority of the events, a period of deeper blocking was seen, as shown in FIG. 2. The light gray line is the data at the effective bandwidth of 100 kHz, while the smoother black line is the data low pass filtered to the set filter frequency of 10 kHz. At the beginning of the majority of the events, an initial deeper blockade was seen. This may be due to interactions occurring as the single stranded DNA was attempting to enter the nanopore. However, it was not believed to be due to the composition of the polymer since the polymer was comprised of only one type of monomer, the nucleotide containing an A base. Thus, for the average residual current values for polyA100 (SEQ ID NO: 2), this initial deeper block was removed from the calculation of the average value.

Heteropolymer Measurements (polyA40C80A40 (SEQ ID NO: 4))

The CNR for the 4SL135I was demonstrated using the single stranded DNA polymer polyA40C80A40 (SEQ ID NO: 4). The residual current measurements for 389 polyA40C80A40 (SEQ ID NO: 4) measurements, where the 3' end entered the nanopore first, were recorded. Of these 389 measurements, 313 or 80.4%, demonstrated at least the expected number of occurrences of the discrete levels for polyA40C80A40 (SEQ ID NO: 4): I_A40 (SEQ ID NO: 5) to I_C80 (SEQ ID NO: 6) and then back to I_A40 (SEQ ID NO: 5). All 313 events were used to compute the contrast signal and total noise value.

Figure 3A:
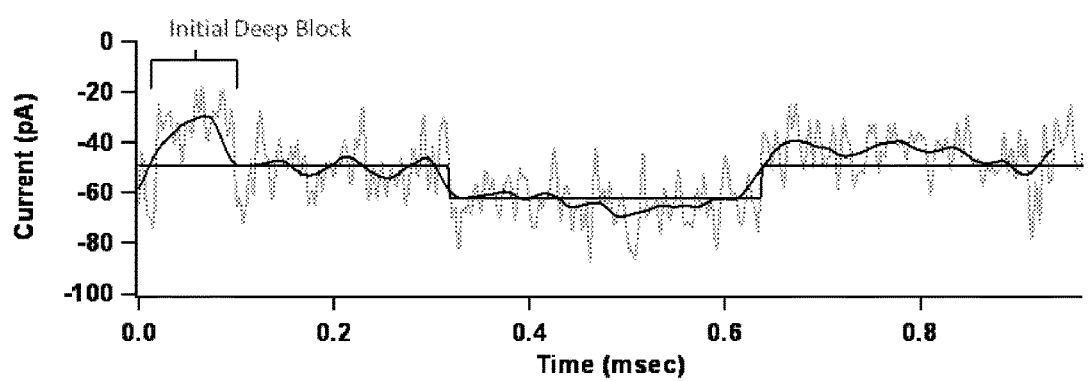
FIG. 3A shows a typical residual current measurement of the polymer polyA40C80A40 (SEQ ID NO: 4) through the 4SL135I nanopore.
Figure 3B:
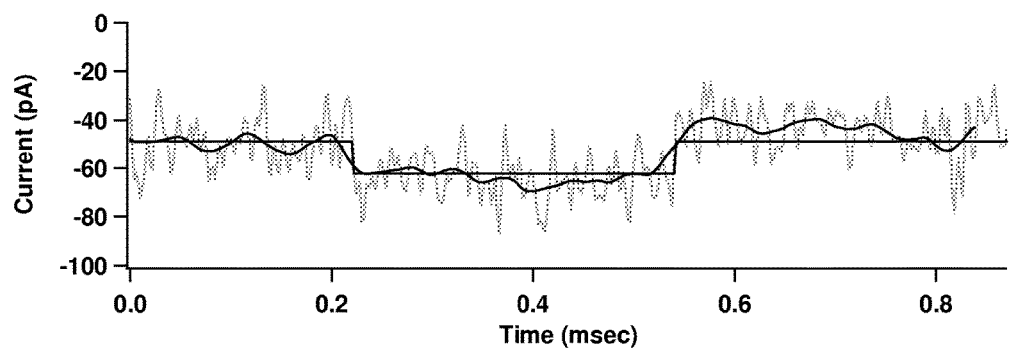
FIG. 3B shows the residual current measurement shown in FIG. 3A with the initial deeper blocking removed.

While many of the events showed more complex residual current measurements than the homopolymers, it was difficult to distinguish the actual discrete levels in an unbiased manner by the untrained eye. A Viterbi algorithm based on the results from a modified Hidden Markov Model was used to identify the discrete levels within the measurements using the levels predicted by the homopolymer measurements (FIG. 3). FIG. 3A shows a typical residual current measurement of the polymer polyA40C80A40 (SEQ ID NO: 4) through the 4SL135I nanopore. At the beginning of the majority of the events, a deeper blocking occurred, as was seen with the polyA100 (SEQ ID NO: 2) measurements. Since this artifact was not due to the composition of the polymer, it was removed from the measurements before computing the contrast signal and total noise value. FIG. 3B shows the residual current measurement shown in FIG. 3A with the initial deeper blocking removed. The light gray line is the data at the effective bandwidth of 100 kHz, while the smoother black line is the data low pass filtered to the set filter frequency of 10 kHz. The solid straight black line is the estimate of the current levels for the A40 (SEQ ID NO: 5), C80 (SEQ ID NO: 6) and A40 (SEQ ID NO: 5) sections according to the Hidden Markov Model, discussed in the next section.

Hidden Markov Model Used in this Example for 4SL 135I

Initial values were set for the model parameters of the Hidden Markov Model (HMM) based on the expected discrete levels and their expected durations given the composition of the polymer. The HMM was then used to analyze a set of residual current measurements. By using the Viterbi algorithm, we can identify the most probable sequence of states or discrete levels for each measurement. At this point, the estimates of the initial model parameters can be refined if necessary.

Figure 4:
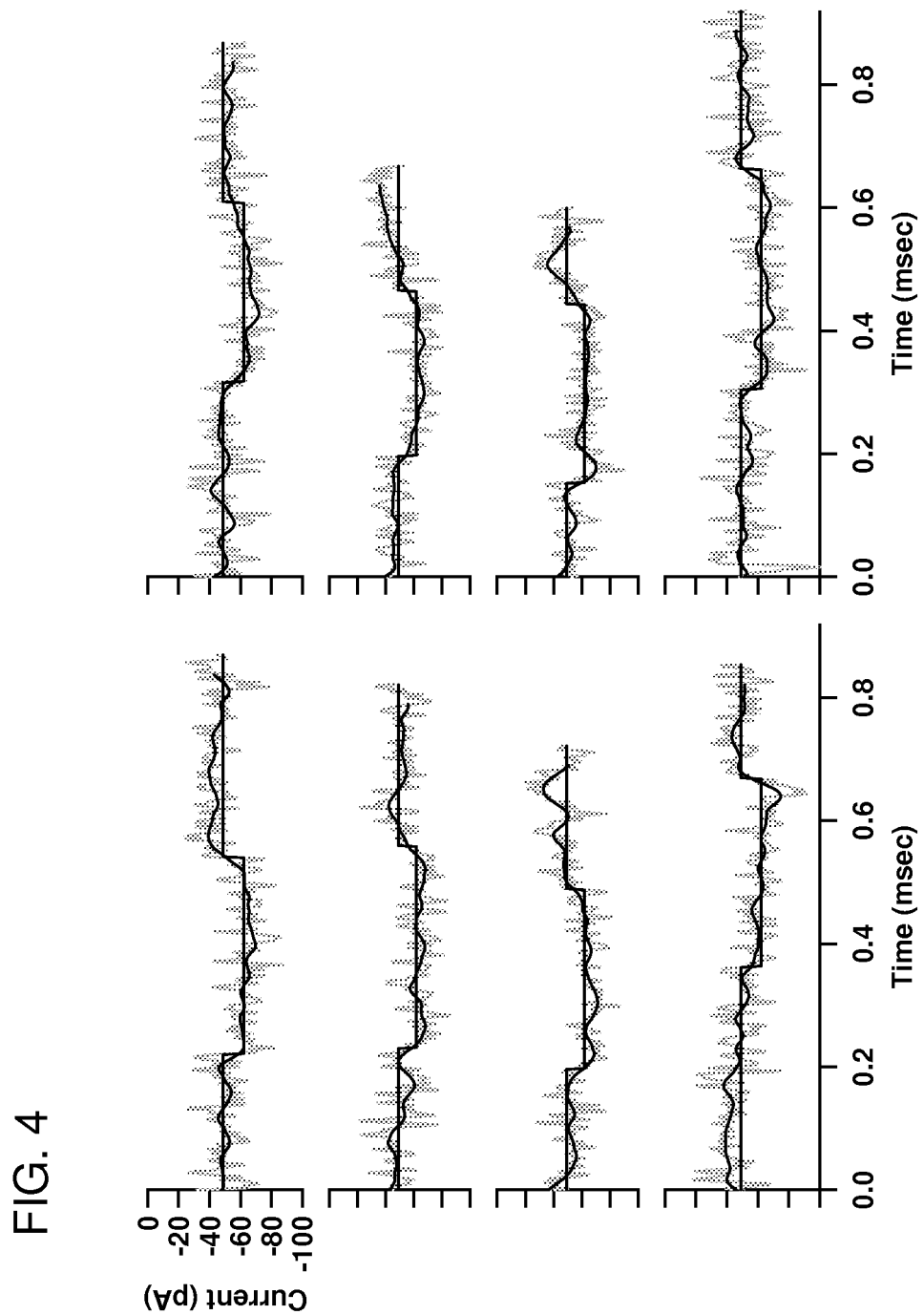
FIG. 4 shows eight individual residual current measurements representative of the data for polyA40C80A40 (SEQ ID NO: 4).

Residual Current Measurements of polyA40C80A40 (SEQ ID NO: 4) Through the 4SL135I Nanopore As mentioned above, the residual current measurements again showed the artifact at the beginning of the events as seen with the polyA100 (SEQ ID NO: 2) measurements. Since this level was not associated with the actual composition of the polymer, it was again removed from the data analysis. The data analysis with the HMM showed that approximately 80% of the events showed at least the expected number of occurrences of the discrete levels within the measurement, a discrete level for the A40 (SEQ ID NO: 5) section, followed by a discrete level for the C80 (SEQ ID NO: 6) section, and then the same discrete level for the second A40 (SEQ ID NO: 5) section as for the first A40 (SEQ ID NO: 5) section. All events that showed at least the expected number of occurrences of the discrete levels were used in the computation of the discrete levels for the A40 (SEQ ID NO: 5) and C80 (SEQ ID NO: 6) sections. Eight individual residual current measurements representative of the data for polyA40C80A40 (SEQ ID NO: 4) are shown in FIG. 4. The light gray line is the data at the effective bandwidth of 100 kHz, while the smoother black line is the data low pass filtered to the set filter frequency of 10 kHz. The solid straight black line is the estimate of the current levels for the A40 (SEQ ID NO: 5), C80 (SEQ ID NO: 6) and A40 (SEQ ID NO: 5) sections according to the Hidden Markov Model, discussed in the above section.

Contrast Signal

The average for the first level for the A40 (SEQ ID NO: 5) section was calculated by averaging the levels for the A40 (SEQ ID NO: 5) section in all of the measurements at the 100 kHz effective bandwidth. The average for the second level corresponding to the C80 (SEQ ID NO: 6) section was also calculated by averaging the levels for the C80 (SEQ ID NO: 6) section in all of the measurements at the 100 kHz effective bandwidth. The average I_A40 (SEQ ID NO: 5) was −49 pA and the average I_C80 (SEQ ID NO: 6) was −61 pA. The contrast signal was the absolute difference between the two discrete levels, yielding a contrast signal of 12 pA. These average I_A40 (SEQ ID NO: 5) and average I_C80 (SEQ ID NO: 6) values were correlated to the composition of the polymer by comparing them to the analysis of the homopolymer data. While the contrast signal was slightly higher for the A40 (SEQ ID NO: 5) and C80 (SEQ ID NO: 6) sections than the polyA100 (SEQ ID NO: 2) and polyC100 (SEQ ID NO: 3) data (9.1 pA contrast signal), the current levels were close to the homopolymer data and were considered correlated.

Total Noise Value

The residual current measurements were filtered to a set filter frequency of 10 kHz using a 3-pole Bessel filter. A beginning portion and an end portion of each discrete level within each measurement were removed to eliminate the transitions from creating an artificially high noise value. Approximately ½ of a time period of the set filter frequency, or about 50 microseconds, was removed from both the beginning and end of each discrete level.

Figure 5:
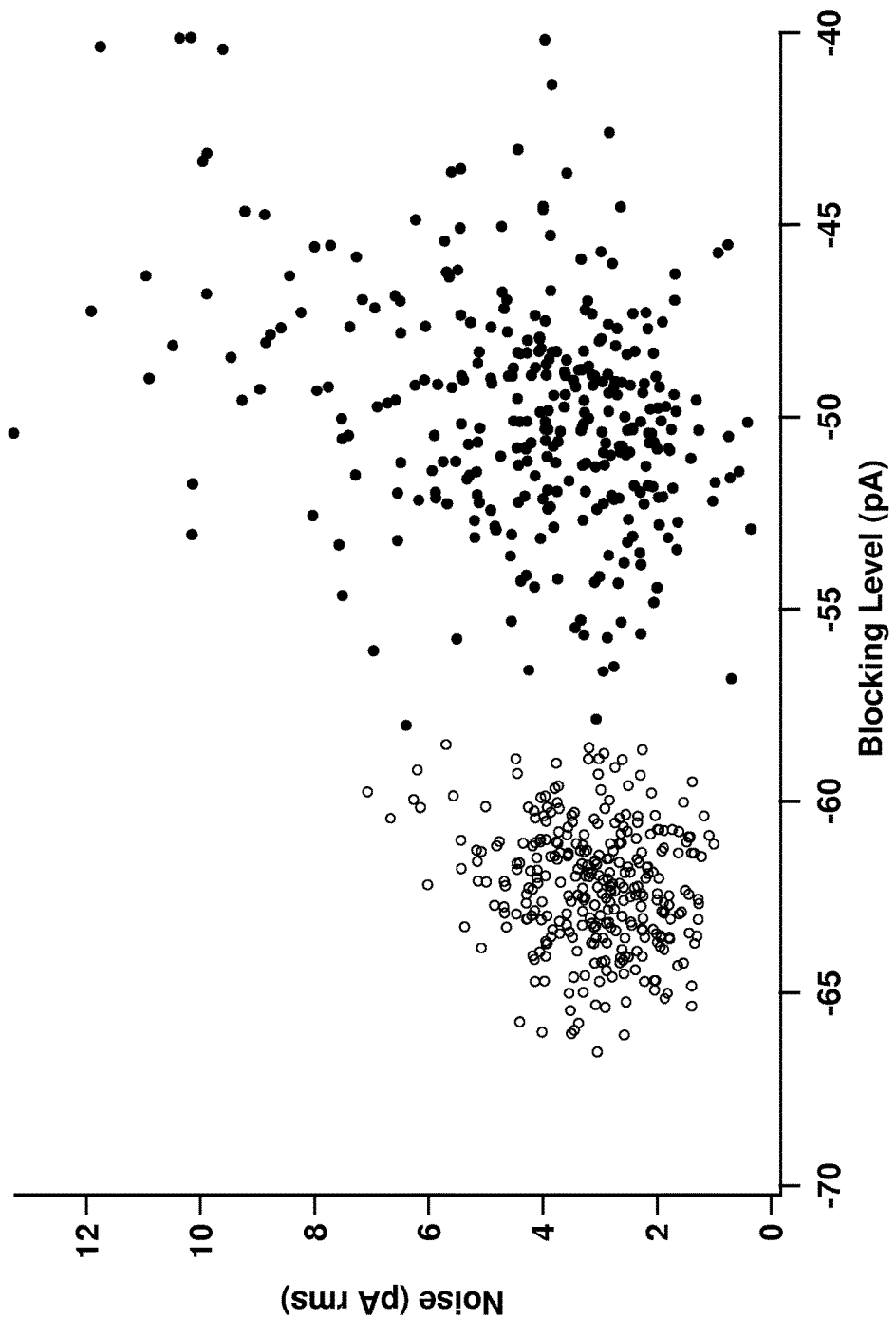
FIG. 5 shows a plot of the residual currents and noise levels for section A40 (SEQ ID NO: 5) (solid data points) and section C80 (SEQ ID NO: 6) (non-filled data points).

The root mean square noise value for each of the discrete levels within each of the measurements was computed and the root mean square noise values for the A40 (SEQ ID NO: 5) discrete levels were averaged over all measurements and the root mean square noise values for the C80 (SEQ ID NO: 6) levels were averaged over all measurements. The average root mean square noise value for the A40 (SEQ ID NO: 5) discrete level at 10 kHz was 4.8 pA and the average root mean square noise value for the C80 (SEQ ID NO: 6) discrete level at 10 kHz was 3.2 pA (FIG. 5). FIG. 5 shows a plot of the residual currents and noise levels for section A40 (SEQ ID NO: 5) (solid data points) and section C80 (SEQ ID NO: 6) (non-filled data points). The average noise value for section A40 (SEQ ID NO: 5) and the average noise value for section C80 (SEQ ID NO: 6) were computed from the data contained in this plot.

The total noise value was calculated by taking the square root of the sum of the squares of the average root mean square noise values for the two discrete levels. Thus, the total noise value was the $\mathrm{sqrt}(4.8^2+3.2^2)$, which equals 5.77 pA at the set filter frequency of 10 kHz.

CNR

The CNR was the contrast signal divided by the total noise value at the set filter frequency. Thus for the 4SL135I, the CNR at a set filter frequency of 10 kHz was 2.08 (12 pA divided by 5.77 pA). This CNR was above the set threshold of 2.

Average Duration

Figure 6A:
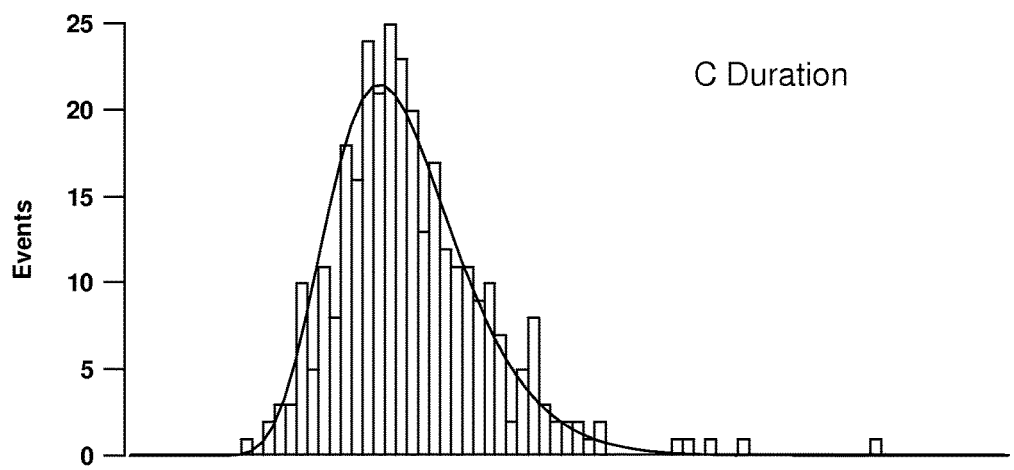
FIG. 6A shows the translocation fit for the durations of the C80 (SEQ ID NO: 6) section.
Figure 6B:
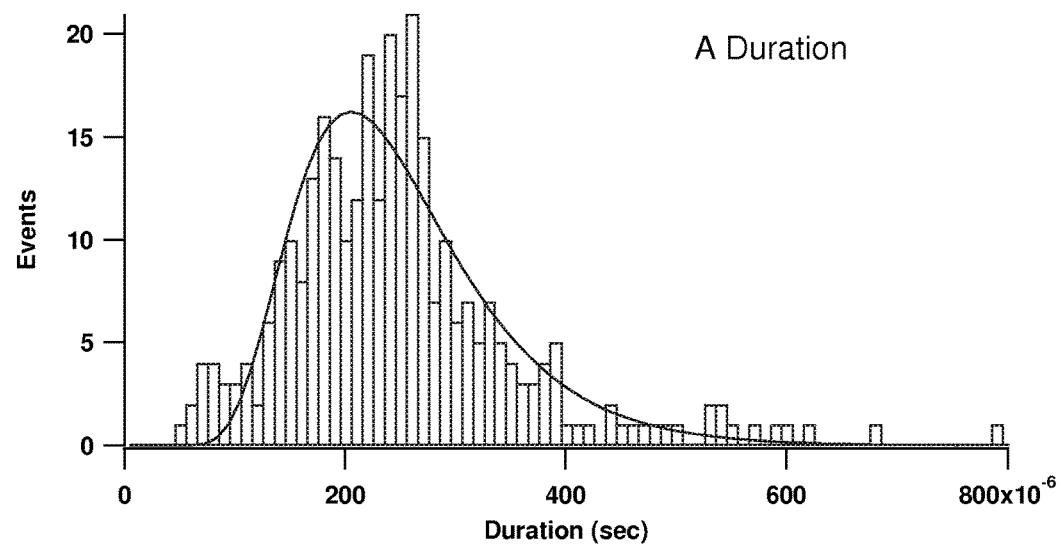
FIG. 6B shows the translocation fit for the durations of the A40 (SEQ ID NO: 5) section.

The duration times were measured for each A40 (SEQ ID NO: 5) section in the measurements used to calculate the CNR. The distribution of durations were found to fit well to a Lubensky translocation model according to Lubensky et al, (D. K. Lubensky, and D. R. Nelson, "Driven Polymer Translocation Through a Narrow Pore," *Biophys. J.*, vol. 77, no. 4, pp. 1824-1838, Oct. 1, 1999, 1999). FIG. 6B shows the translocation fit for the durations of the A40 (SEQ ID NO: 5) section. The Tmax value for the A40 (SEQ ID NO: 5) section durations was 244 microseconds (FIG. 6B). The duration times were measured for each C80 (SEQ ID NO: 6) section in the measurements used to calculate the CNR. The distribution of durations were found to fit well to a Lubensky translocation model. FIG. 6A shows the translocation fit for the durations of the C80 (SEQ ID NO: 6) section. The Tmax value for the C80 (SEQ ID NO: 6) section was computed in the same manner and was determined to be 259 microseconds (FIG. 6A). Thus, the average duration for one of the discrete levels used to calculate the CNR, the duration for section A40 (SEQ ID NO: 5), was below the threshold set of 1 millisecond. In this particular Example, the average duration for both of the discrete levels used to calculate the CNR was below the threshold set of 1 millisecond.

Thus, the 4SL135I nanopore was a high contrast nanopore according to the definition set forth in this application.

Example 3: 4SL135I-D127K Analyzed by AC/DC System

Oligonucleotides and Measurement

The single stranded DNA homopolymers, polyA100 (SEQ ID NO: 2) and polyC100 (SEQ ID NO: 3), and the heteropolymer polyA50C70 (SEQ ID NO: 7) (GeneLink) were PAGE purified and delivered in a 10 mM Tris, 1 mM EDTA solution buffered to pH 8.5 at a concentration of 100 microMolar. These DNA strands also included a Biotin molecule on the 5' end of the polyA100 (SEQ ID NO: 2) and polyC100 (SEQ ID NO: 3) strands and Biotin Tetraethylene Glycol (TEG) molecules on the 5' end of polyA50C70 (SEQ ID NO: 7). These solutions were stored at −80° C. Prior to use, the DNA was diluted to a concentration of 20 microMolar. Approximately 5.0 microliters of the DNA was mixed with 2.5 microliters of a 100 microMolar streptavidin solution and incubated at room temperature for approximately 10 minutes. Approximately 6 microliters of the DNA/steptavidin solution was then added to the approximately 250 microliter test cell. The attachment of a streptavidin molecule to the DNA provides a hard stop for the DNA as it enters the pore with the 3' end first. This allows the translocation measurement to begin at a known starting point when the voltage bias polarity was reversed. Experiments were run with the polyA100 (SEQ ID NO: 2) and polyC100 (SEQ ID NO: 3) in the same experiment with the 4SL135I-D127K protein and separately with the polyA50C70 (SEQ ID NO: 7) with the 4SL135I-D127K protein. The homopolymers were measured to be able to correlate the discrete levels within the heteropolymer (polyA50C70 (SEQ ID NO: 7)) to the actual composition of the sections of the polymer.

Once a 4SL135I-D127K insertion was obtained and homopolymer events were observed, data was acquired at 20° C. for approximately 10 minutes. With the AC/DC measurement system, the DNA was captured by applying a 120 mV DC bias. Once the DNA was in the pore, an AC signal of 150 mV at a frequency of 50 kHz was applied along with a −30 mV DC bias for the homopolymers. The opposite polarity DC bias helps to direct the motion of the DNA back out of the pore in order to measure DNA translocating the pore. Another experiment was then setup with a single 4SL135I-D127K insertion and heteropolymer events were recorded at 20° C. for approximately 30 minutes. The conditions were identical to the homopolymer experiment with the exception that a −40 mV DC bias was used rather than a −30 mV DC bias. The effective bandwidth for the data for both experiments was 10 kHz.

Homopolymer Measurements (polyA100 (SEQ ID NO: 2) and polyC100 (SEQ ID NO: 3))

Figure 7A:
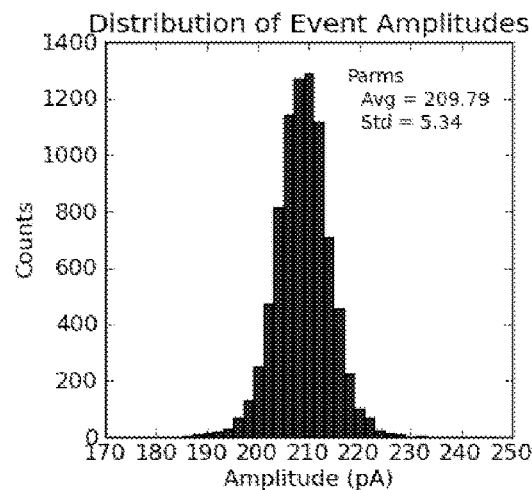
FIG. 7A shows an all points histogram of the residual current measurements for polyA100 (SEQ ID NO: 2) 3' (3' end entering the nanopore first) through the 4SL135I-D127K nanopore.
Figure 7B:
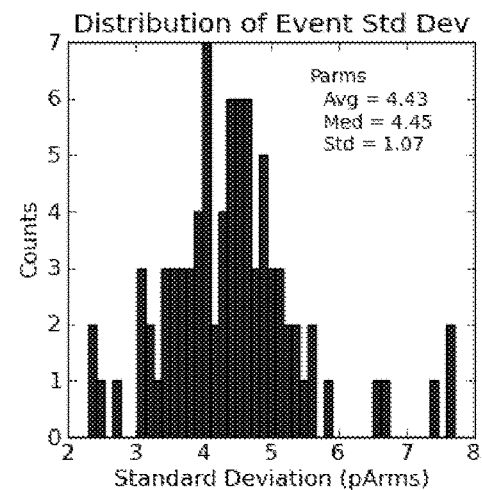
FIG. 7B shows the distribution of event standard deviation (i.e. noise values) for polyA100 (SEQ ID NO: 2) 3' at 10 kHz.
Figure 7C:
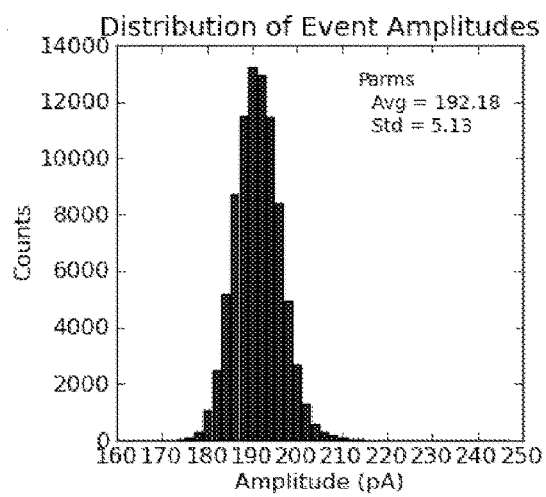
FIG. 7C shows an all points histogram of the residual current measurements for polyC100 (SEQ ID NO: 3) 3' (3' end entering the nanopore first).
Figure 7D:
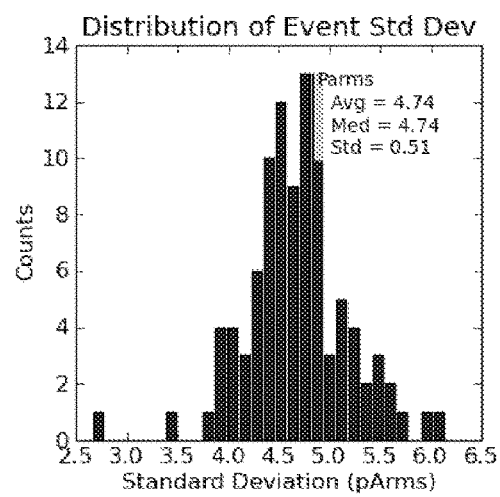
FIG. 7D shows the distribution of event standard deviation (i.e. noise values) for polyC100 (SEQ ID NO: 3) 3' at 10 kHz.

The residual current measurements for polyA100 (SEQ ID NO: 2) events and polyC100 (SEQ ID NO: 3) events were recorded. The distribution of event amplitudes for polyA100 (SEQ ID NO: 2) 3' and polyC100 (SEQ ID NO: 3) 3' (3' end entering the nanopore first) are shown in FIG. 7A and FIG. 7C respectively. The average current values for polyA100 (SEQ ID NO: 2) and polyC100 (SEQ ID NO: 3) were estimated from the all points histograms of the event amplitudes (FIG. 7A and FIG. 7C respectively). The average residual current measurement for polyA100 (SEQ ID NO: 2) over those events at the effective bandwidth of 10 kHz was approximately 209.8 pA and for polyC100 (SEQ ID NO: 3) it was approximately 192.2 pA. With the AC/DC measurements, the open channel current was nominally set to 0 pA. The distribution of event standard deviation (i.e. noise values) for polyA100 (SEQ ID NO: 2) 3' and polyC100 (SEQ ID NO: 3) 3' at 10 kHz are shown in FIG. 7B and FIG. 7D respectively. This yielded an absolute difference between the polyA100 (SEQ ID NO: 2) and polyC100 (SEQ ID NO: 3) of 17.6 pA.

Heteropolymer Measurements (polyA50C70 (SEQ ID NO: 7))

Figure 8A:
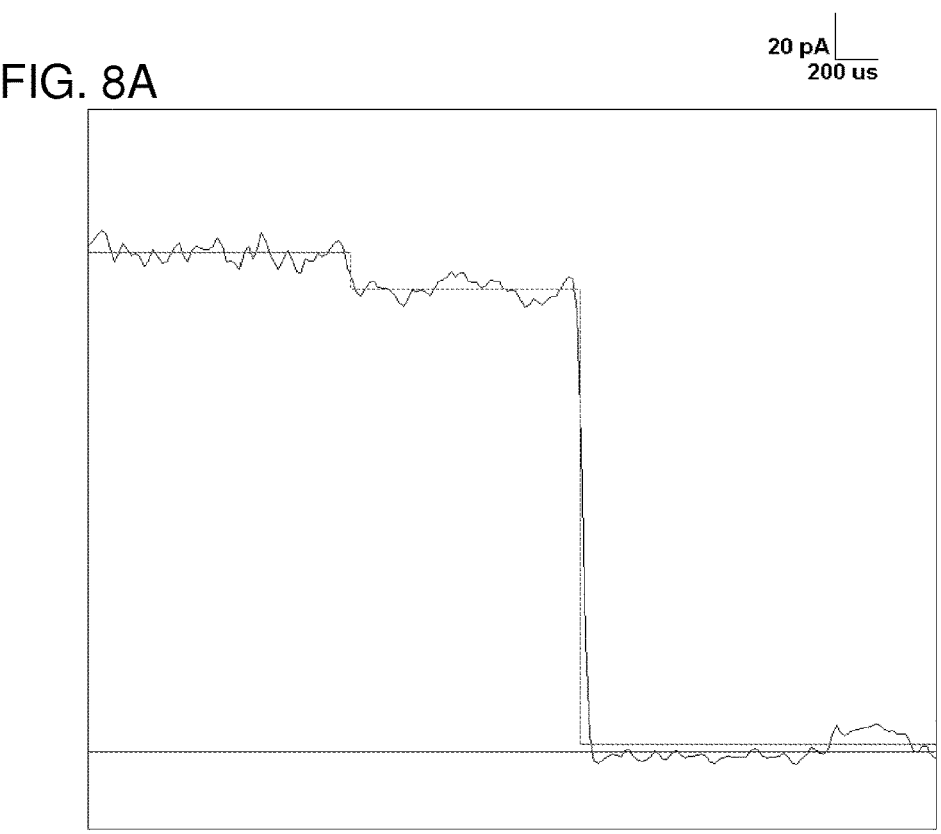
FIG. 8A and FIG. 8B show examples of the residual current measurements for the single stranded DNA polymer polyA50C70 (SEQ ID NO: 7) through the 4SL135I-D127K nanopore.
Figure 8B:
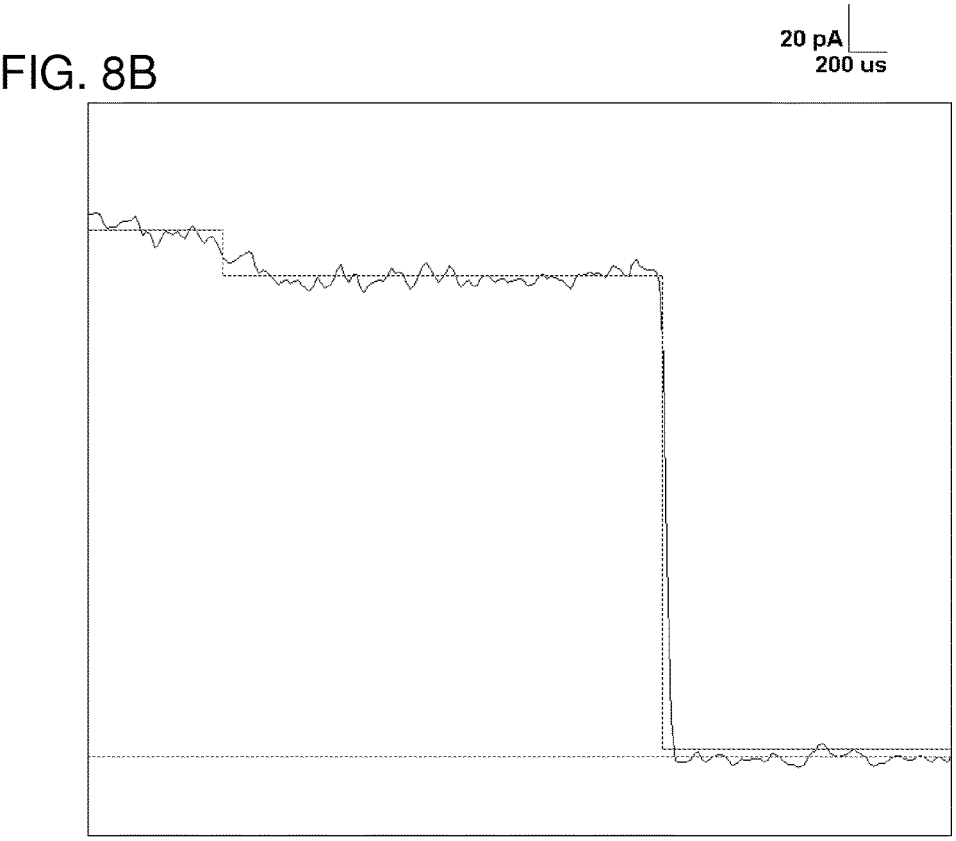

The CNR for the 4SL135I-D127K was demonstrated using the single stranded DNA polymer polyA50C70 (SEQ ID NO: 7). The residual current measurements for 102 polyA50C70 (SEQ ID NO: 7) measurements showing the expected number of transitions (I_A50 (SEQ ID NO: 8) followed by I_C70 (SEQ ID NO: 9)) were analyzed. Example traces are presented in FIG. 8A and FIG. 8B. FIG. 8A shows a typical residual current measurement of the polymer polyA50C70 (SEQ ID NO: 7) through the 4SL135I-D127K nanopore. The beginning of the trace showed the level for A50 (SEQ ID NO: 8) followed by the level for C70 (SEQ ID NO: 9). The current trace returned to open (right side of trace) once the DNA exited the pore. FIG. 8B shows another example of the event type described for FIG. 8A. The straight line that stair steps in both FIG. 8A and FIG. 8B shows the idealization trace of the data implemented by a Hidden Markov model to determine the current levels for each section. The bottom straight line represents the open channel current level.

Contrast Signal

Figure 9A:
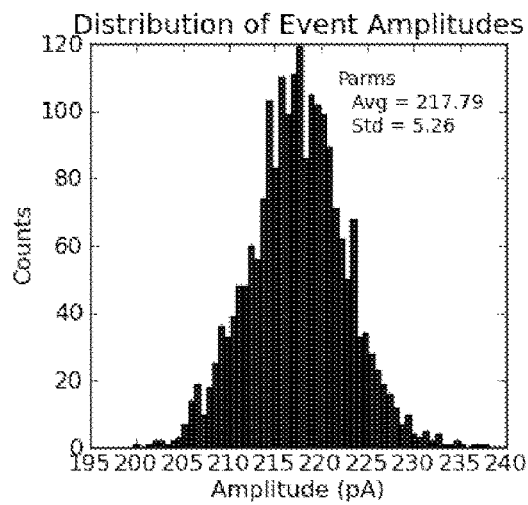
FIG. 9A shows the distribution of event amplitudes for the A50 (SEQ ID NO: 8) section.
Figure 9B:
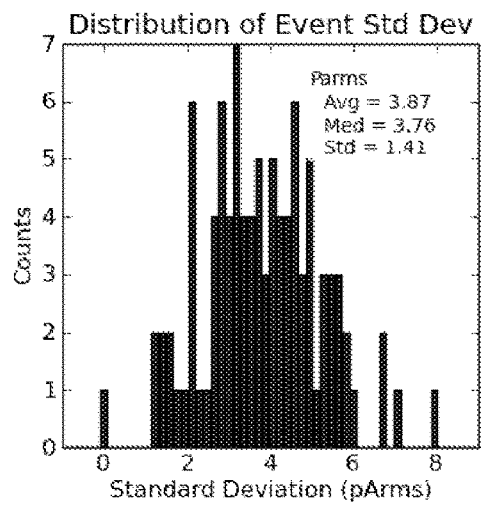
FIG. 9B shows the distribution of event standard deviation (i.e. noise values) for the A50 (SEQ ID NO: 8) section at 10 kHz.
Figure 9C:
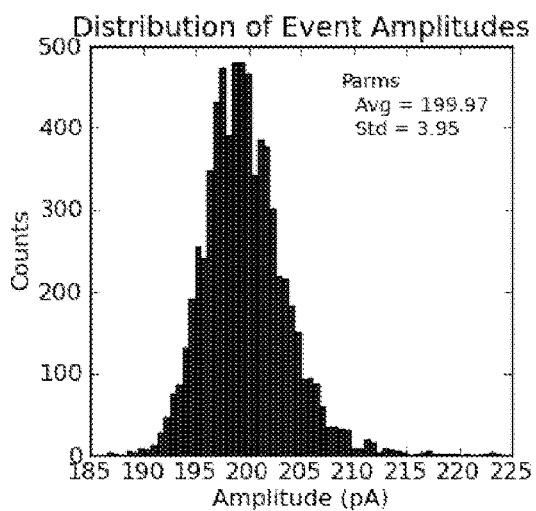
FIG. 9C shows an all points histogram of the residual current measurements for the C70 (SEQ ID NO: 9) section.
Figure 9D:
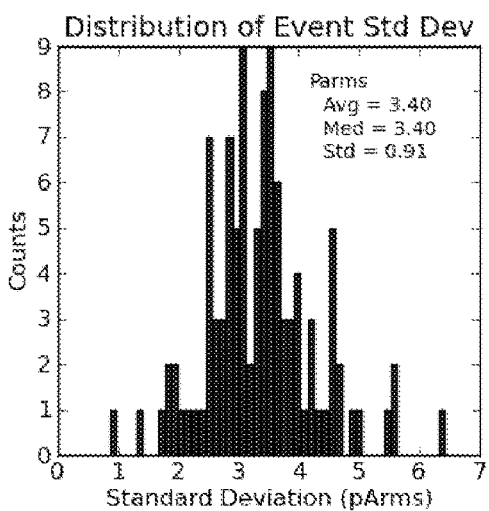
FIG. 9D shows the distribution of event standard deviation (i.e. noise values) for the C70 (SEQ ID NO: 9) section at 10 kHz.

The average for the first discrete level for the A50 (SEQ ID NO: 8) section was calculated by averaging all of the points for the discrete levels for the A50 (SEQ ID NO: 8) section in all of the measurements at the 10 kHz effective bandwidth. The average for the second discrete level corresponding to the C70 (SEQ ID NO: 9) section was also calculated by averaging all of the points for the discrete levels for the C70 (SEQ ID NO: 9) section in all of the measurements at the kHz effective bandwidth. The average I_A50 (SEQ ID NO: 8) was 217.8 pA and the average I_C70 (SEQ ID NO: 9) was 200 pA (FIGS. 9A and 9C respectively). The contrast signal was the absolute difference between the two average discrete levels, yielding a contrast signal of 17.8 pA. These average I_A50 (SEQ ID NO: 8) and average I_C70 (SEQ ID NO: 9) values were correlated to the composition of the polymer by comparing them to the analysis of the homopolymer data. While the absolute current levels were slightly different between the homopolymer and heteropolymer experiments, the contrast values (17.6 pA and 17.8 pA respectively) were almost identical. Thus, the discrete levels have been correlated to the composition of the polymer.

Total Noise Value

The residual current measurements were filtered to a set filter frequency of 10 kHz using a 3-pole Bessel filter. A beginning portion and an end portion of each discrete level within each measurement were removed to eliminate the transitions from creating an artificially high noise value. Approximately ½ of a time period of the set filter frequency, or about 50 microseconds, was removed from both the beginning and end of each discrete level.

The root mean square noise value for each of the discrete levels within each of the measurements was computed and the root mean square noise values for the A50 (SEQ ID NO: 8) discrete levels were averaged over all measurements and the root mean square noise values for the C70 (SEQ ID NO: 9) levels were averaged over all measurements. The average root mean square noise value for the A50 (SEQ ID NO: 8) discrete level at 10 kHz was 3.87 pA and the average root mean square noise value for the C70 (SEQ ID NO: 9) discrete level at 10 kHz was 3.40 pA (FIG. 9B and FIG. 9C respectively).

The total noise value was calculated by taking the square root of the sum of the squares of the average root mean square noise values for the two discrete levels. Thus, the total noise value was the sqrt($3.87^2+3.40^2$), which equals 5.15 pA at the set filter frequency of 10 kHz.

CNR

The CNR was the contrast signal divided by the total noise value at the set filter frequency. Thus for 4SL135I-D127K, the CNR at a set filter frequency of 10 kHz was 3.46 (17.8 pA divided by 5.15 pA). This CNR was above the set threshold of 2.

Average Duration

Figure 10A:
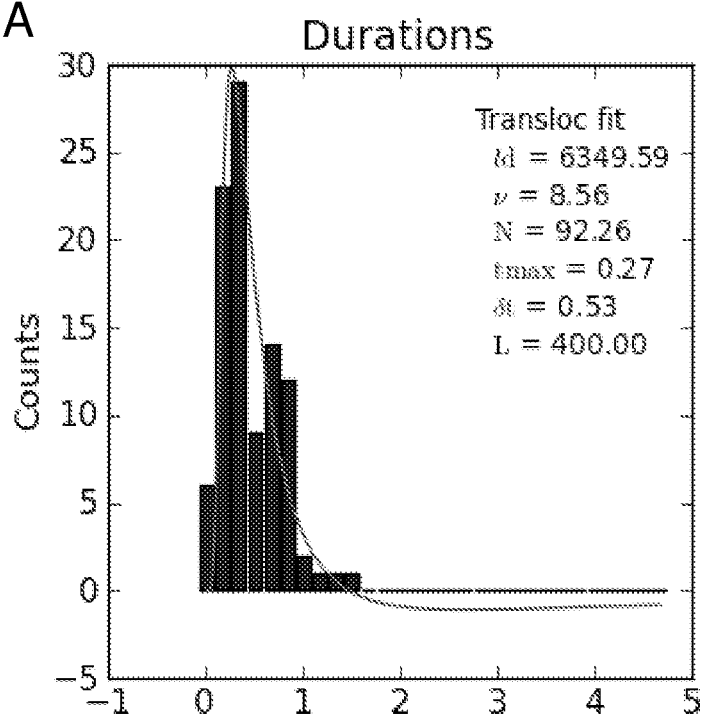
FIG. 10A shows the translocation fit for the durations of the A50 (SEQ ID NO: 8) section.
Figure 10B:
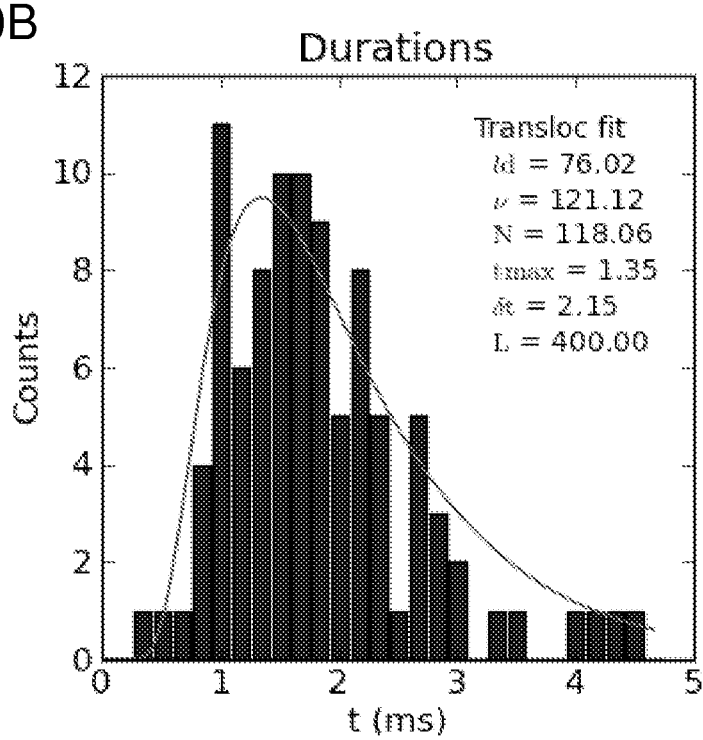
FIG. 10B shows the translocation fit for the durations of the C70 (SEQ ID NO: 9) section.

The duration times were measured for each A50 (SEQ ID NO: 8) section (FIG. 10A) in the measurements used to calculate the CNR. The distribution of durations were found to fit well to a Lubensky translocation model according to Lubensky et al, (D. K. Lubensky, and D. R. Nelson, "Driven Polymer Translocation Through a Narrow Pore," *Biophys. J.*, vol. 77, no. 4, pp. 1824-1838, Oct. 1, 1999). The Tmax value for the A50 (SEQ ID NO: 8) section durations was 270 microseconds. The duration times were measured for each C70 (SEQ ID NO: 9) section in the measurements used to calculate the CNR. The distribution of durations were found to fit well to a Lubensky translocation model. The Tmax value for the C70 (SEQ ID NO: 9) section was computed in the same manner (FIG. 10B) and was determined to be 1350 microseconds. Thus, the average duration for one of the discrete levels used to calculate the CNR, the duration for section A50 (SEQ ID NO: 8), was below the threshold set of 1 millisecond.

Thus, the 4SL135I-D127Ks nanopore was a high contrast nanopore according to the definition set forth in this application.

Example 4: 4S-N121S-N139S Analyzed by AC/DC System

The example for the protein pore 4S-N121S-N139S was completed using the same protocols for the 4SL135I-D127K protein pore shown above for the heteropolymer and CNR analysis. The measurements were also carried out using the AC/DC system. Two differences to be noted include: the heteropolymer used was polyA40C50A25 (SEQ ID NO: 11) (rather than polyA50C70 (SEQ ID NO: 7)) and the DC bias used was −30 mV (rather than −40 mV with the heteropolymer). Another difference was that the correlation of the discrete levels to the composition of the sections of the polymer were completed using the immobilized method with the DC system with polyA40 (SEQ ID NO: 5) and polyC40 (SEQ ID NO: 10), both with Biotin on the 5' end.

Immobilized Homopolymer Measurements (polyA40 (SEQ ID NO: 5) and polyC40 (SEQ ID NO: 10), Completed with DC System)

The single stranded DNA homopolymers, polyA40 (SEQ ID NO: 5) and polyC40 (SEQ ID NO: 10) (GeneLink) were PAGE purified and delivered in a 10 mM Tris, 1 mM EDTA solution buffered to pH 8.5 at a concentration of 100 microMolar. These DNA strands also included a Biotin molecule on the 5' end. These solutions were stored at −80° C. Prior to use, the DNA was diluted to a concentration of 20 microMolar. Approximately 5.0 microliters of the DNA was mixed with 2.5 microliters of a 100 microMolar streptavidin solution and incubated at room temperature for approximately 10 minutes. Approximately 6 microliters of the polyC40 (SEQ ID NO: 10) DNA/steptavidin solution was then added to the approximately 250 microliter test cell.

A single 4S-N121S-N139S insertion was obtained. A DC voltage bias of −120 mV was applied to drive the DNA into the nanopore. The DNA would translocate through the pore until the streptavidin was prevented from going through the nanopore. The residual current of the immobilized strand was recorded for approximately 1 second. The DC bias was then reversed to 120 mV to eject the DNA from the pore. The bias was again reversed back to −120 mV to obtain another DNA measurement. This was repeated for approximately 20 to 30 minutes. This measurement was taken to ensure that the level for polyC40 (SEQ ID NO: 10) was known prior to adding the polyA40 (SEQ ID NO: 5). Approximately 6 microliters of the polyA40 (SEQ ID NO: 5) DNA/steptavidin solution was then added to the approximately 250 microliter test cell with the polyC40 (SEQ ID NO: 10) still in solution. The measurement process was then repeated with both strands in solution, thus obtaining measurements of both polyA40 (SEQ ID NO: 5) and polyC40 (SEQ ID NO: 10), for approximately 30 minutes.

Figure 11:
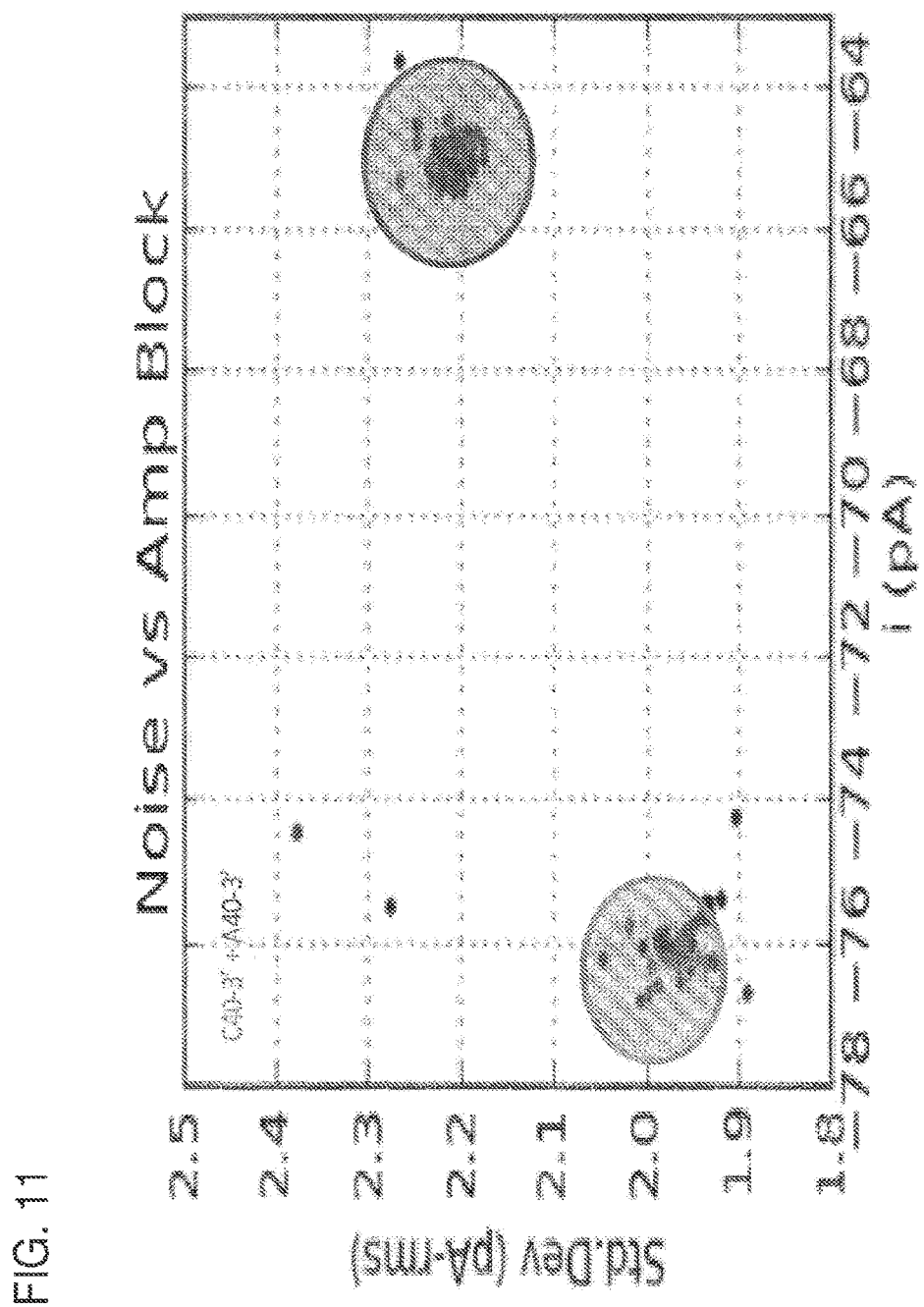
FIG. 11 shows the noise vs. current blockade level for polyC40 (SEQ ID NO: 10) (left hand population) and polyA40 (SEQ ID NO: 5) (right hand population) in the 4S-N121S-N139S nanopore.

The average residual current measurement for polyC40 (SEQ ID NO: 10) over those events at the effective bandwidth of 10 kHz was approximately −76.0 pA and for polyA40 (SEQ ID NO: 5) it was approximately −65.1 pA, (FIG. 11). With the DC measurements, the open channel current for this pore was −266.8 pA. The average noise values at the effective bandwidth of 10 kHz for polyC40 (SEQ ID NO: 10) and polyA40 (SEQ ID NO: 5) were 2.0 pA and 2.2 pA respectively. This yielded an absolute difference between the polyA40 (SEQ ID NO: 5) and polyC40 (SEQ ID NO: 10) of 10.9 pA.

Heteropolymer Measurements (polyA40C50A25 (SEQ ID NO: 11))

Figure 12A:
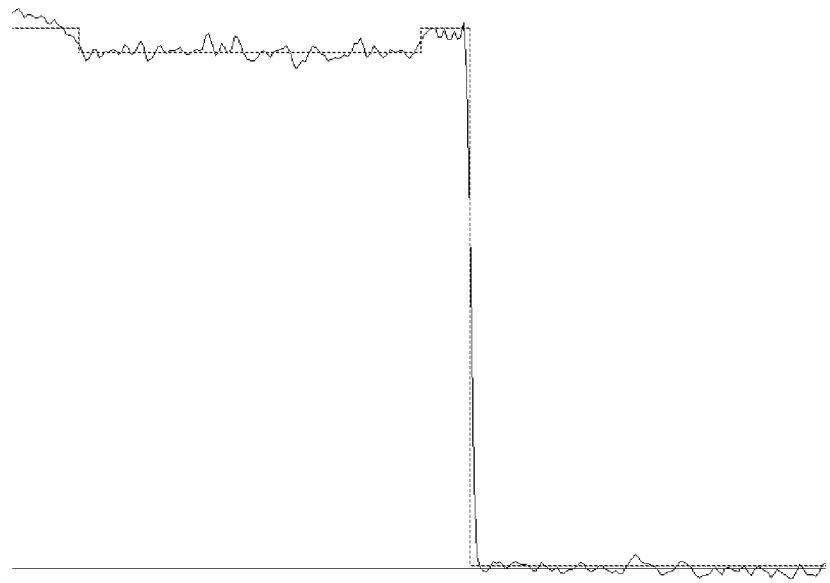
FIG. 12A and FIG. 12B show a typical residual current measurement of the polymer polyA40C50A25 (SEQ ID NO: 11) through the 4S-N121S-N139S nanopore.
Figure 12B:
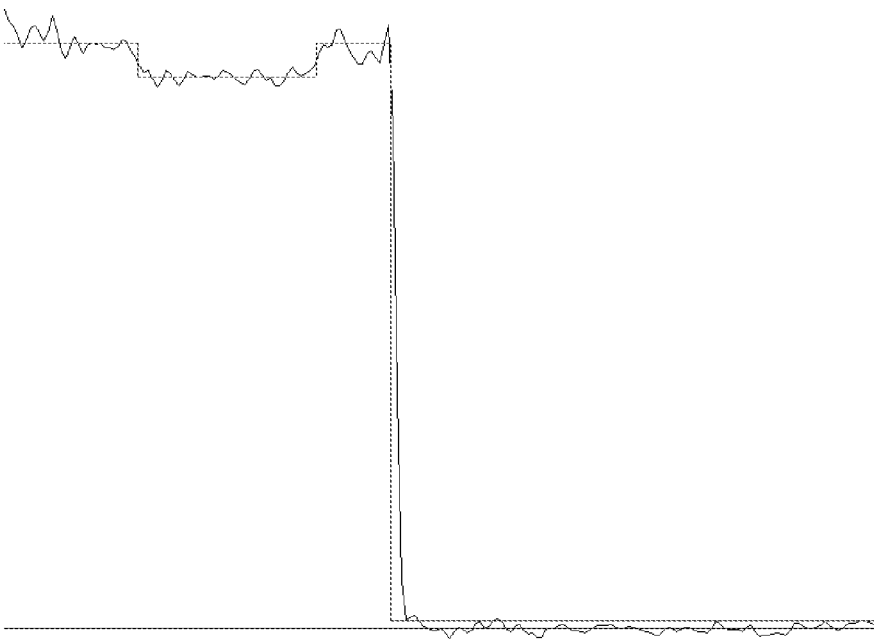
Figure 13A:
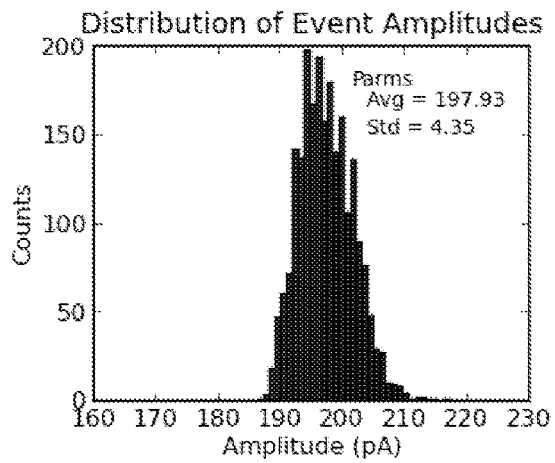
FIG. 13A shows the distribution of event amplitudes for the A40 (SEQ ID NO: 5) section.
Figure 13B:
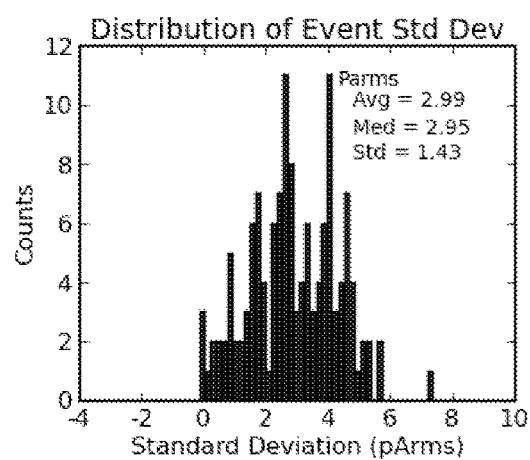
FIG. 13B the distribution of event standard deviation (noise) for the A40 (SEQ ID NO: 5) section at 10 kHz.
Figure 13C:
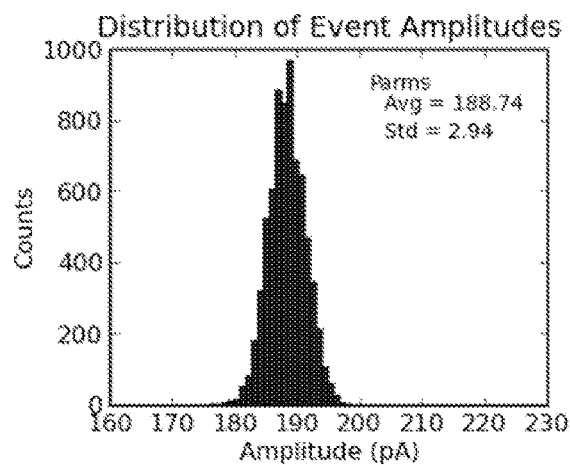
FIG. 13C shows the distribution of event amplitudes for the C50 (SEQ ID NO: 12) section.

The CNR for the 4S-N121S-N139S was demonstrated using the single stranded DNA polymer polyA40C50A25 (SEQ ID NO: 11). The residual current measurements for 76 polyA40C50A25 (SEQ ID NO: 11) measurements showing the expected number of transitions (I_A40 (SEQ ID NO: 5) followed by I_C50 (SEQ ID NO: 12) and then I_A25 (SEQ ID NO: 45)) were analyzed. FIG. 12A shows a typical residual current measurement of the polymer polyA40C50A25 (SEQ ID NO: 11) through the 4S-N121S-N139S nanopore. The beginning of the trace shows the level for A40 (SEQ ID NO: 5) followed by the level for C50 (SEQ ID NO: 12) and then the level for A25 (SEQ ID NO: 45). The current trace returns to open (right side of trace) once the DNA exits the pore. FIG. 12B shows another example of the event type described for FIG. 12A. The straight line that stair steps in both FIG. 12A and FIG. 12B shows the idealization trace of the data implemented by a Hidden Markov model to determine the current levels for each section. The bottom straight line represents the open channel current level Contrast Signal The average I_A40 (SEQ ID NO: 5) was 197.9 pA and the average I_C50 (SEQ ID NO: 12) was 188.7 pA (FIG. 13A and FIG. 13C respectively). The contrast signal was the absolute difference between the two average discrete levels, yielding a contrast signal of 9.2 pA.

These average I_A40 (SEQ ID NO: 5) and average I_C50 (SEQ ID NO: 12) values were correlated to the composition of the polymer by comparing them to the analysis of the immobilized homopolymer data. While the contrast using immobilized homopolymers polyA40 (SEQ ID NO: 5) and polyC40 (SEQ ID NO: 10) was slightly higher than the contrast using heteropolymers (10.9 pA vs. 9.2 pA), the levels were close. In addition, in both experiments, the adenine bases blocked a larger amount than the cytosine bases. Thus, the discrete levels have been correlated to the composition of the polymer.

Total Noise Value

The residual current measurements were filtered to a set filter frequency of 10 kHz using a 3-pole Bessel filter. A beginning portion and an end portion of each discrete level within each measurement were removed to eliminate the transitions from creating an artificially high noise value. Approximately ½ of a time period of the set filter frequency, or about 50 microseconds, was removed from both the beginning and end of each discrete level.

Figure 13D:
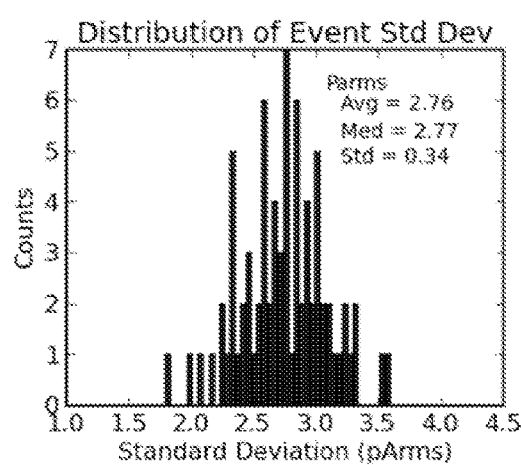
FIG. 13D shows the distribution of event standard deviation for C50 (SEQ ID NO: 12) section at 10 kHz.

The average root mean square noise value for the A40 (SEQ ID NO: 5) discrete level at 10 kHz was 2.99 pA (FIG. 13B) and the average root mean square noise value for the C50 (SEQ ID NO: 12) discrete level at 10 kHz was 2.76 pA (FIG. 13D).

The total noise value was the sqrt($2.99^2+2.76^2$), which equals 4.07 pA at the set filter frequency of 10 kHz.

CNR

The CNR was the contrast signal divided by the total noise value at the set filter frequency. Thus for the 4S-N121S-N139S, the CNR at a set filter frequency of 10 kHz was 2.25 (9.2 pA divided by 4.07 pA). This CNR was above the set threshold of 2.

Average Duration

Figure 14A:
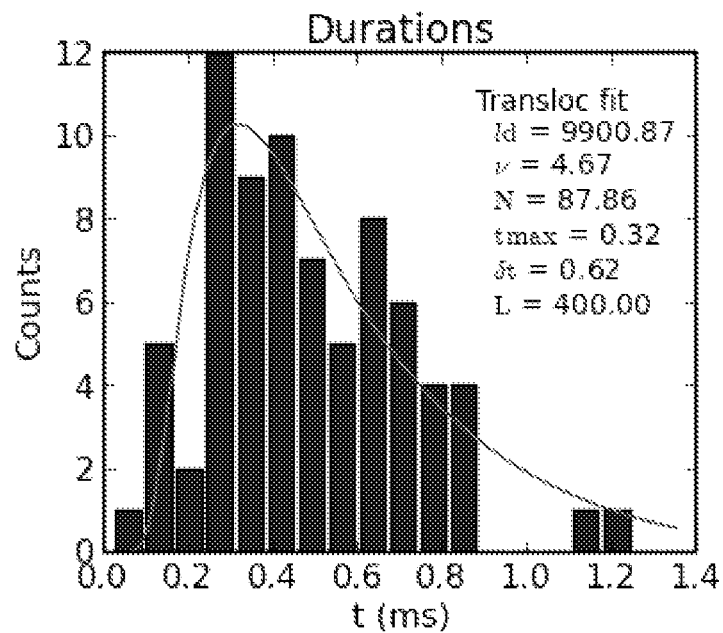
FIG. 14A shows the translocation fit for the durations of the A40 (SEQ ID NO: 5) section.
Figure 14B:
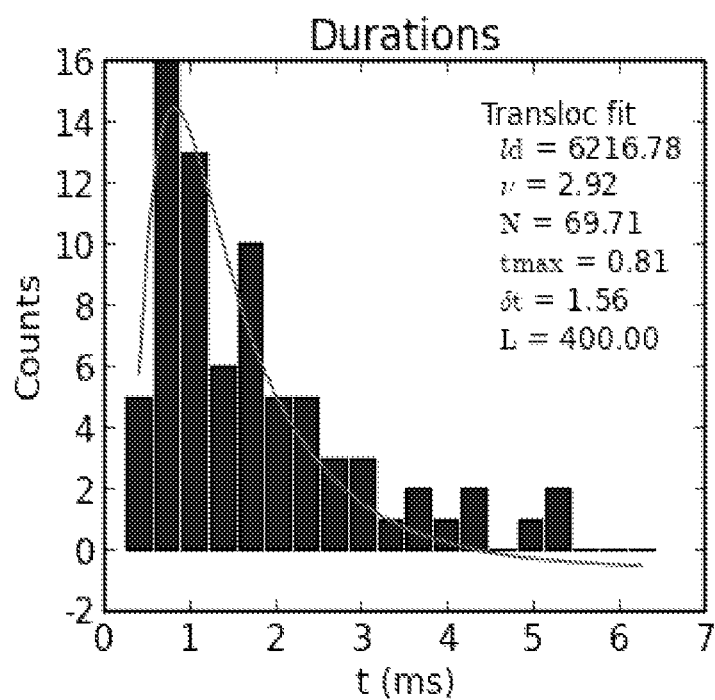
FIG. 14B shows the translocation fit for the durations of the C50 (SEQ ID NO: 12) section.

The duration times were measured for each A40 (SEQ ID NO: 5) section in the measurements used to calculate the CNR. The distribution of durations were found to fit well to a translocation model according to Lubensky et al, (D. K. Lubensky, and D. R. Nelson, "Driven Polymer Translocation Through a Narrow Pore," *Biophys. J.*, vol. 77, no. 4, pp. 1824-1838, Oct. 1, 1999). The Tmax value for the A40 (SEQ ID NO: 5) section durations was 320 microseconds (FIG. 14A). The duration times were measured for each C50 (SEQ ID NO: 12) section in the measurements used to calculate the CNR. The distribution of durations were found to fit well to a translocation model. The Tmax value for the C50 (SEQ ID NO: 12) section was 810 microseconds (FIG. 14B). Thus, the average duration for one of the discrete levels used to calculate the CNR, the duration for section A40 (SEQ ID NO: 5), was below the threshold set of 1 millisecond. In this example, the average duration for the C50 (SEQ ID NO: 12) section was also below the threshold set of 1 millisecond. The duration times were measured for each A50 (SEQ ID NO: 8) section (FIG. 10A) in the measurements used to calculate the CNR. The distribution of durations were found to fit well to a translocation model according to Lubensky et al, (D. K. Lubensky, and D. R. Nelson, "Driven Polymer Translocation Through a Narrow Pore," *Biophys. J.*, vol. 77, no. 4, pp. 1824-1838, Oct. 1, 1999). The Tmax value for the A50 (SEQ ID NO: 8) section durations was 270 microseconds. The duration times were measured for each C70 (SEQ ID NO: 9) section in the measurements used to calculate the CNR. The distribution of durations were found to fit well to a translocation model.

Thus, the 4S-N121S-N129S nanopore was a high contrast nanopore according to the definition set forth in this application.

Example 5: Examples of Embodiments

Provided hereafter are non-limiting examples of certain embodiments.

A1. A nanopore comprising one or more amino acid modifications that permit measurement of a first level and a second level within a residual current of the nanopore, as a polymer translocates through the nanopore, with a contrast signal to noise ratio (CNR) of two (2) or greater computed at a predetermined filter frequency;

which polymer comprises two or more sections, each of which sections comprises at least a portion of a monomer;

which CNR is calculated as a contrast signal divided by a total noise value;

which contrast signal is calculated as the absolute difference between the first level and the second level, wherein:

each level used for calculating the CNR correlates to a composition of a section of the polymer, each level is an average of measurements within the residual current for each section of the polymer, the first level and the second level are measurably distinct, and at least one of the first level and the second level has an average duration of one millisecond or less; and which total noise value is the square root of the sum of the squares of a first average root mean square noise value of the first level at the predetermined filter frequency and a second average root mean square noise value of the second level at the predetermined filter frequency.

A2. The nanopore of embodiment A1, which is an isolated protein.

A3. The nanopore of embodiment A1 or A2, wherein the pore of the nanopore comprises a beta barrel.

A4. The nanopore of embodiment A2, wherein the nanopore is chosen from alpha hemolysin, MspA, OmpF, PA63 and gramicidin A.

A5. The nanopore of embodiment A4, wherein the nanopore is a modified alpha hemolysin.

A6. The nanopore of any one of embodiments A1 to A5, wherein the average of measurements of the first level and the second level are computed at the predetermined filter frequency.

A7. The nanopore of embodiment A6, wherein one quarter of a time period of the predetermined filter frequency is removed from the beginning and end of first levels and second levels prior to computing the first level and second level.

A7.1 The nanopore of embodiment A6, wherein one half of a time period of the predetermined filter frequency is removed from the beginning and end of first levels and second levels prior to computing the first level and second level.

A8. The nanopore of any one of embodiments A1 to A7.1, wherein one quarter of a time period of the predetermined filter frequency is removed from the beginning and end of first levels and second levels within individual current measurements prior to computing the average root mean square noise values for each level.

A9. The nanopore of any one of embodiments A1 to A8, wherein one half of a time period of the predetermined filter frequency is removed from the beginning and end of first levels and second levels within individual current measurements prior to computing the average root mean square noise values for each level.

A10. The nanopore of any one of embodiments A1 to A9, which permits measurement of the first level and the second level for at least two sets of two distinct sections within the polymer with a CNR of 2 or greater.

A11. The nanopore of any one of embodiments A1 to A10, which permits measurement of the first level and the second level for at least three sets of two distinct sections within the polymer with a CNR of 2 or greater.

A12. The nanopore of any one of embodiments A1 to A11, which permits measurement of the first level and the second level for at least four sets of two distinct sections within the polymer with a CNR of 2 or greater.

A13. The nanopore of any one of embodiments A1 to A12, which permits measurement of the first level and the second level for at least five sets of two distinct sections within the polymer with a CNR or 2 or greater.

A13.1. The embodiments of any one of A10 to A13 wherein at least one of the sets of two distinct sections is on a different polymer.

A14. The nanopore of any one of embodiments A1 to A13, wherein the CNR is 2.5 or greater.

A15. The nanopore of any one of embodiments A1 to A14, wherein the CNR is 3.0 or greater.

A16. The nanopore of any one of embodiments A1 to A15, wherein the CNR is 3.5 or greater.

A17. The nanopore of any one of embodiments A1 to A16, wherein the CNR is 4.0 or greater.

A18. The nanopore of any one of embodiments A1 to A17, wherein the CNR is 5.0 or greater.

A19. The nanopore of any one of embodiments A1 to A18, wherein the CNR is 6.0 or greater.

A20. The nanopore of any one of embodiments A1 to A19, wherein the CNR is 7.0 or greater.

A21. The nanopore of any one of embodiments A1 to A20, wherein the CNR is 8.0 or greater.

A22. The nanopore of any one of embodiments A1 to A21, wherein the CNR is 9.0 or greater.

A23. The nanopore of any one of embodiments A1 to A22, wherein the CNR is 10.0 or greater.

A24. The nanopore of any one of embodiments A1 to A23, wherein the predetermined filter frequency is chosen from about 1 kHz to about 500 kHz.

A25. The nanopore of embodiment A24, wherein the predetermined filter frequency is 10 kHz.

A26. The nanopore of embodiment A24, wherein the predetermined filter frequency is 100 kHz.

A27. The nanopore of any one of embodiments A1 to A26, wherein data is filtered to the predetermined filter frequency using a low pass 3 pole Bessel filter.

A28. The nanopore of any one of embodiments A1 to A27, wherein the polymer is a protein or peptide.

A28.1. The nanopore of any one of embodiments A1 to A27, wherein the polymer is a nucleic acid.

A28.2. The nanopore of embodiment A28.1, wherein the polymer is DNA or RNA

A29. The nanopore of embodiment A28.1 or A28.2, wherein the polymer is single stranded or double stranded DNA.

A29.1 The nanopore of embodiment A28.1 or A28.2, wherein the polymer is single stranded DNA.

A30. The nanopore of any one of embodiments A1 to A29.1, wherein the monomer is chosen from a nucleotide, monophosphate nucleotide, oxidized nucleotide, methylated nucleotide or modified nucleotide.

A31. The nanopore of embodiment A30, wherein the nucleotide is comprised of a base chosen from adenine, cytosine, thymine, guanine or uracil.

A32. The nanopore of any one of embodiments A1 to A31, wherein the average duration of each level is calculated from the average of the duration times for each of the measurements used to calculate each level.

A32.1. The nanopore of embodiment A1 to A31, wherein the average duration of each level is calculated from the arithmetic mean of the duration times for each of the measurements used to calculate each level.

A33. The nanopore of embodiments A1 to A31, wherein the average duration of each level is calculated by fitting the distribution of duration times to a mathematical model.

A33.1 The nanopore of embodiments A33, wherein the mathematical model is an exponential model and the average duration of the level is set to the time constant Tau value of the fit.

A34. The nanopore of embodiments A33 or A33.1, wherein the mathematical model is a translocation model and the average duration of the level is set to the Tmax value.

A34.1. The nanopore of any one of embodiments A33 to A34, wherein the mathematical model is a Lubensky translocation model and the average duration of the level is set to the Tmax value.

A35. The nanopore of any one of embodiments A1 to A34.1, wherein the average duration is at most 900 microseconds.

A36. The nanopore of any one of embodiments A1 to A34.1, wherein the average duration is at most 800 microseconds.

A37. The nanopore of any one of embodiments A1 to A34.1, wherein the average duration is at most 700 microseconds.

A38. The nanopore of any one of embodiments A1 to A34.1, wherein the average duration is at most 600 microseconds.

A39. The nanopore of any one of embodiments A1 to A34.1, wherein the average duration is at most 500 microseconds.

A40. The nanopore of any one of embodiments A1 to A34.1, wherein the average duration is at most 400 microseconds.

A41. The nanopore of any one of embodiments A1 to A34.1, wherein the average duration is at most 300 microseconds.

A42. The nanopore of any one of embodiments A1 to A34.1, wherein the average duration is at most 200 microseconds.

A43. The nanopore of any one of embodiments A1 to A34.1, wherein the average duration is at most 100 microseconds.

A44. The nanopore of any one of embodiments A1 to A34.1, wherein the average duration is at most 50 microseconds.

A45. The nanopore of any one of embodiments A1 to A34.1, wherein the average duration is at most 10 microseconds.

A46. The nanopore of any one of embodiments A1 to A45, wherein the one or more amino acid modifications to the nanopore is substitution of one or more native amino acids.

A46.1. The nanopore of any one of embodiments A1 to A46, wherein the nanopore is an alpha hemolysin pore.

A47. The nanopore of embodiment A46 or A46.1, wherein one or more native amino acids are substituted with a non-native amino acid.

A48. The nanopore of any one of embodiments A46 to A47, wherein at least one of the native amino acids in a primary constriction in the nanopore is substituted to simplify the primary constriction.

A49. The nanopore of embodiment A48, wherein the substitution to simplify the primary constriction is chosen from: an amino acid that reduces the charge compared to the native amino acid, an amino acid that eliminates the charge of the side chain of the native amino acid, an amino acid that reduces hydrogen bonding between the amino acid and the polymer compared to the native amino acid and the polymer, an amino acid smaller in size than the native amino acid, and an amino acid that changes hydrophobic interactions between the amino acid and the DNA.

A50. The nanopore of embodiment A48 or A49, wherein the substitution to simplify the primary constriction increases the contrast signal.

A51. The nanopore of any one of embodiments A48 to A50, wherein the substitution to simplify the primary constriction reduces the total noise value.

A52. The nanopore of any one of embodiments A48 to A51, wherein the substitution to simplify the primary constriction increases the CNR.

A53. The nanopore of any one of embodiments A46 to A52, wherein one or more native amino acids in a secondary constriction is substituted to enhance the secondary constriction.

A54. The nanopore of embodiment A53, wherein the substitution to enhance the secondary constriction is chosen from: an amino acid that changes the charge compared to the native amino acid, an amino acid that increases hydrogen bonding between the amino acid and the polymer compared to the native amino acid and the polymer, and an amino acid that is larger in size than the native amino acid.

A55. The nanopore of embodiment A53 or A54, wherein the substitution to enhance the secondary constriction increases the contrast signal.

A56. The nanopore of any one of embodiments A53 to A55, wherein the substitution to enhance the secondary constriction reduces the total noise value.

A57. The nanopore of any one of embodiments A53 to A56, wherein the substitution to enhance the secondary constriction increases the CNR.

A58. The nanopore of any one of embodiments A48 to A57, wherein at least one of the native amino acids in a salt bridge in the alpha hemolysin pore is substituted to change or disrupt the salt bridge.

A58.1. The nanopore of any one of embodiments A48 to A57, wherein at least one of the native amino acids in a salt bridge in the alpha hemolysin pore is substituted to move the salt bridge.

A58.2. The nanopore of any one of embodiments A48 to A57, wherein at least one of the native amino acids in the alpha hemolysin pore is substituted to add a salt bridge.

A58.3. The nanopore of any one of embodiments A48 to A57, wherein at least one amino acid is deleted from or added to an alpha hemolysin pore protein to change, disrupt, add or remove a salt bridge.

A59. The nanopore of embodiment A58, wherein the substitution to change or disrupt the salt bridge is chosen from: an amino acid that changes the charge of one of the native amino acids in the salt bridge to the same charge as the other amino acid in the salt bridge, and an amino acid change that changes one of the native amino acids in the salt bridge without changing its charge.

A60. The nanopore of any one of embodiments A58 to A59, wherein the change, disruption, moving, adding or removing the salt bridge increases the contrast signal.

A61. The nanopore of any one of embodiments A58 to A60, wherein the change, disruption, moving, adding or removing the salt bridge reduces the total noise value.

A62. The nanopore of any one of embodiments A58 to A61, wherein the change, disruption, moving, adding or removing the salt bridge increases the CNR.

A63. The nanopore of any one of embodiments A48 to A62, wherein the nanopore is alpha hemolysin and the native amino acids M113, E111, K147 and T145 in the primary constriction independently are substituted with a non-native amino acid.

A64. The nanopore of any one of embodiments A48 to A63, wherein the nanopore is alpha hemolysin and the native amino acids M113, E111, K147 and T145 in the primary constriction independently are substituted with a non-native amino acid and the native amino acid L135 in the secondary constriction is substituted with a non-native amino acid.

A65. The nanopore of embodiment A64, wherein the nanopore is alpha hemolysin and the native amino acids M113, E111, K147 and T145 in the primary constriction are substituted with serine and the native amino acid L135 in the secondary constriction is substituted with isoleucine.

A66 The nanopore of any one of embodiments A48 to A65, wherein the nanopore is alpha hemolysin and the native amino acids M113, E111, K147 and T145 in the primary constriction independently are substituted with a non-native amino acid and the native amino acid L135 in the secondary constriction is substituted with a non-native amino acid and the native amino acid D127 in the salt bridge is substituted with a non-native amino acid.

A67. The nanopore of embodiment A66, wherein the nanopore is alpha hemolysin and the native amino acids M113, E111, K147 and T145 in the primary constriction are substituted with serine and the native amino acid L135 in the secondary constriction is substituted with isoleucine and the native amino acid D127 in the salt bridge is substituted with lysine.

A68. The nanopore of embodiment A63, wherein the nanopore is alpha hemolysin and the native amino acids N121 and N139 in the secondary constriction are substituted with a non-native amino acid.

A69. The nanopore of embodiment A68, wherein the nanopore is alpha hemolysin and the native amino acids N121 and N139 in the secondary constriction are substituted with serine.

A70. The nanopore of any one of embodiments A1 to A69, wherein the first level and the second level are computed from at least 50 measurements.

A70.1. The nanopore of any one of embodiments A1 to A69, wherein the first level and the second level are computed from at least 75 measurements.

A70.2. The nanopore of any one of embodiments A1 to A69, wherein the first level and the second level are computed from at least 100 measurements.

A70.3. The nanopore of any one of embodiments A1 to A69, wherein the first level and the second level are computed from at least 200 measurements.

A70.4. The nanopore of any one of embodiments A1 to A69, wherein the first level and the second level are computed from at least 500 measurements.

A71. The nanopore of embodiment A70, wherein the measurements used to calculate the first level and the second level each demonstrate the expected number of levels for the polymer.

A72. The nanopore of embodiment A71, wherein every measurement that demonstrates at least the expected number of occurrences of the levels for the polymer is used to calculate the first level and the second level.

A73. The nanopore of any one of embodiments A1 to A72, wherein the CNR at the predetermined filter frequency is calculated under a specific set of test conditions.

A74. The nanopore of embodiment A73, wherein the test conditions include an electrolyte, a known polymer, and an applied bias.

A75. The nanopore of embodiment A74, wherein the electrolyte is chosen from sodium chloride, potassium chloride, lithium chloride and combinations thereof.

A76. The nanopore of any one of embodiments A74 to A75, wherein the electrolyte has a concentration of about 0.1 Molar (M) to about 6 M.

A77. The nanopore of any one of embodiments A74 to A76, wherein the electrolyte includes a buffer to stabilize the pH of the solution.

A78. The nanopore of embodiment A74, wherein the applied bias is a DC bias and is about 20 mV to about 300 greater.

A79. The nanopore of embodiment A74, wherein the polymer is single stranded DNA.

A80. The nanopore of embodiment A79, wherein the single stranded DNA comprises at least two different types of monomers.

A81. The nanopore of embodiment A80, wherein the single stranded DNA is chosen from the following sequences: polyA40C80A40 (SEQ ID NO: 4), polyA20C120A20 (SEQ ID NO: 28), polyA40C120A10 (SEQ ID NO: 29), polyA40GA40 (SEQ ID NO: 23), polyA40G4A10C60 (SEQ ID NO: 30), polyA40G4A40 (SEQ ID NO: 18), polyC40T40C40 (SEQ ID NO: 31), polyT40C40T40 (SEQ ID NO: 32), polyT50G4T50 (SEQ ID NO: 33), polyA20C40A20C40A20 (SEQ ID NO: 34), polyACACACACACACACACACACACACACAC (SEQ ID NO: 35), polyA40CA40 (SEQ ID NO: 36), polyA40C2A40 (SEQ ID NO: 37), polyT40CT40 (SEQ ID NO: 38), polyT40C2T40 (SEQ ID NO: 39), polyT40GT40 (SEQ ID NO: 40), polyC40AC40 (SEQ ID NO: 41), polyC40TC40 (SEQ ID NO: 42), polyC40A2C40 (SEQ ID NO: 43), and polyC40T2C40 (SEQ ID NO: 44).

A82. The nanopore of any one of embodiments A73 to A81, wherein translocation of the polymer within the nanopore is controlled.

A83. The nanopore of embodiment A82, wherein the polymer is associated with a molecule chosen from an exonuclease, a polymerase, a single stranded binding protein, an enzyme, hybridizing segments of complementary strands to portions of single stranded polymer, the like or combinations thereof.

A84. The nanopore of embodiment A77, wherein the electrolyte is 3 M sodium chloride, the buffer is 10 mM Tris and 1 mM EDTA, the polymer is single stranded DNA and the applied bias is 120 mV.

A85. The nanopore of embodiment A84, wherein the single stranded DNA is polyA40C80A40 (SEQ ID NO: 4).

A86. The nanopore of embodiment A84, wherein the single stranded DNA is polyA20C120A20 (SEQ ID NO: 28).

A87. The nanopore of embodiment A84, wherein the single stranded DNA is polyA40G4A40 (SEQ ID NO: 18).

A88. The nanopore of embodiment A84, wherein the single stranded DNA is polyT40C80T40 (SEQ ID NO: 46).

A89. The nanopore of embodiment A84, wherein the single stranded DNA is polyC80A40C80 (SEQ ID NO: 47).

A89.1. The nanopore of embodiment A84, wherein the single stranded DNA is polyA40G4C40 (SEQ ID NO: 48).

A89.2. The nanopore of embodiment A84, wherein the single stranded DNA is polyA50C70 (SEQ ID NO: 7).

A90. The nanopore of any one of embodiments A1 to A89.2, wherein the first level and the second level are correlated to each corresponding composition of the respective sections of the polymer by measuring the residual current of a first homopolymer and a second homopolymer translocating the nanopore where the first homopolymer comprises the same monomer or monomers in a first section of the polymer that produced the first level used to compute the CNR and the second homopolymer comprises the same monomer or monomers in a second section of the polymer that produced the second discrete level used to compute the CNR.

A91. The nanopore of any one of embodiments A1 to A89.2, wherein the discrete levels are correlated to each corresponding composition of the sections of the polymer by measuring the residual current of a first homopolymer and a second homopolymer immobilized within the nanopore where the first homopolymer is comprised of the same monomer or monomers that comprises the first section of the polymer that produced the first discrete level used to compute the CNR and the second homopolymer is comprised of the same monomer or monomers that comprises the second section of the polymer that produced the second discrete level used to compute the CNR A92. The nanopore of any one of embodiments A1 to A89.2, wherein the first level and the second level are correlated to each corresponding composition of the respective sections of the polymer by mapping the nanopore with an immobilized polymer that comprises the same monomer or monomers in the sections of the polymer that produce the first discrete level used to computer the CNR and the second discrete level used to compute the CNR.

A93. The nanopore of embodiment A74 to A92, wherein the applied bias is an AC bias and is about 50 mV to about 1000 mV.

A94. The nanopore of embodiment A93, wherein the AC bias is applied with a periodic source signal with a frequency of about 10 kHz to about 300 kHz or greater.

A95. The nanopore of embodiment A93 or A94, further comprising an applied DC bias.

A96. The nanopore of embodiment A95, wherein the applied DC bias is about 1 mV to about 300 mV.

A97. The nanopore of embodiment A95, wherein the applied DC bias is about 10 mV.

A98. The nanopore of embodiment A95, wherein the applied DC bias is about 40 mV.

A99. The nanopore of any one of embodiments A1 to A98, wherein the sections of the polymer consist of 200 monomers or less.

B1. A device comprising a nanopore of any one of embodiments A1 to A99.

B2. The device of embodiment B1, comprising a lipid bilayer in which the nanopore resides.

B3. The device of B1 or B2 wherein the device comprises a polymerase, exonuclease, single stranded binding protein, helicase and/or one or more hybridizing segments of complementary strands of DNA with a portion of the polymer.

B4. The device of B3 wherein the rate of translocation of a polymer through the nanopore is controlled.

B5. The device of B4 wherein the rate of translocation of a polymer through the nanopore is slowed to an average duration of about 2 ms or slower per section.

B6. The device of embodiment B5 wherein the duration threshold is below 1 ms.

C1. A method for determining the sequence of a polymer, comprising:
 (a) contacting a polymer with a device of embodiment B1 to B6
 (b) measuring the residual current of the nanopore under conditions in which the polymer translocates the nanopore;
 (c) determining the sequence of at least a portion of the polymer based on levels within the residual current measurement.

C2. The method of embodiment C1, further comprising controlling the rate of translocation of the polymer.

C3. The method of embodiment C2, wherein controlling the rate of translocation of the polymer comprises associating a polymerase, exonuclease, single stranded binding protein, helicase and/or one or more hybridizing segments of complementary strands of DNA with a portion of the polymer.

C4. The method of any one of embodiments C1 to C3, wherein the polymer is measured at least one time.

C5. The method of any one of embodiments C1 to C4, further comprising applying a data analysis technique to correlate the levels to the composition of the polymer to determine the sequence of the polymer.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A nanopore comprising a modified *Staphylococcus aureus* alpha hemolysin polypeptide, wherein:
   non-native amino acids are substituted for native amino acids at positions M113, E111, K147 and T145 of a wild-type *Staphylococcus aureus* alpha hemolysin polypeptide, wherein the amino acid positions of the wild-type *Staphylococcus aureus* alpha hemolysin polypeptide align with corresponding positions of the amino acid sequence of the *Staphylococcus aureus* alpha hemolysin polypeptide of SEQ ID NO. 1; and
   the modified alpha hemolysin polypeptide permits measurement of at least a first level and a second level within a residual current of the nanopore, as a polymer translocates through the nanopore, with a contrast signal to noise ratio (CNR) of two (2) or greater computed at a predetermined filter frequency;
   which polymer comprises two or more sections, each of which sections comprises at least a portion of a monomer;
   which CNR is calculated as a contrast signal divided by a total noise value; and
   which contrast signal is calculated as the absolute difference between the first level and the second level, wherein:
      each level used for calculating the CNR correlates to a composition of a section of the polymer,
      each level is an average of measurements within the residual current for each section of the polymer,
      the first level and the second level are measurably distinct, and
      at least one of the first level and the second level has an average duration of one millisecond or less; and
   which total noise value is the square root of the sum of the squares of a first average root mean square noise value of the first level at the predetermined filter frequency and a second average root mean square noise value of the second level at the predetermined filter frequency.

2. The nanopore of claim 1, further comprising a non-native amino acid substitution at position L135 of a wild-type *Staphylococcus aureus* alpha hemolysin polypeptide, wherein the amino acid position of the wild-type *Staphylococcus aureus* alpha hemolysin polypeptide aligns with a corresponding position of the amino acid sequence of the *Staphylococcus aureus* alpha hemolysin polypeptide of SEQ ID NO. 1.

3. The nanopore of claim 1, wherein the average of measurements of the first level and the second level are computed at the predetermined filter frequency and one half of a time period of the predetermined filter frequency is removed from the beginning and end of first levels and second levels prior to computing the first level and second level.

4. The nanopore of claim 1, which permits measurement of the first level and the second level for at least two sets of two distinct sections within the polymer with a CNR of 2 or greater.

5. The nanopore of claim 1, wherein the CNR is 3.0 or greater.

6. The nanopore of claim 1, wherein the predetermined filter frequency is 10 kHz.

7. The nanopore of claim 1, wherein data is filtered to the predetermined filter frequency using a low pass 3 pole Bessel filter.

8. The nanopore of claim 1, wherein the polymer is DNA or RNA.

9. The nanopore of claim 8, wherein the polymer is single stranded DNA.

10. The nanopore of claim 1, wherein the average duration is at most 500 microseconds.

11. The nanopore of claim 1, wherein the non-native amino acids are chosen from: an amino acid that reduces the charge compared to the native amino acid, an amino acid that eliminates the charge of the side chain of the native amino acid, an amino acid that reduces hydrogen bonding between the amino acid and the polymer compared to the native amino acid and the polymer, an amino acid smaller in size than the native amino acid, or an amino acid that changes hydrophobic interactions between the amino acid and the DNA, wherein the substitution increases the CNR.

12. The nanopore of claim 1, wherein the first level and the second level are computed from at least 50 measurements.

13. The nanopore of claim 1, wherein the CNR at the predetermined filter frequency is calculated under test conditions comprising an electrolyte, a known polymer, an applied bias and a buffer, and wherein the electrolyte is 3 M sodium chloride, the buffer is 10 mM Tris and 1 mM EDTA, the known polymer is a polyA40C80A40 single stranded DNA and the applied bias is 120 mV.

14. The nanopore of claim 1, wherein the first level and the second level are correlated to each corresponding composition of the respective sections of the polymer by measuring the residual current of a first homopolymer and a second homopolymer translocating the nanopore where the first homopolymer comprises the same monomer or monomers in a first section of the polymer that produced the first level used to compute the CNR and the second homopolymer comprises the same monomer or monomers in a second section of the polymer that produced the second discrete level used to compute the CNR.

15. The nanopore of claim 1, wherein the discrete levels are correlated to each corresponding composition of the sections of the polymer by measuring the residual current of a first homopolymer and a second homopolymer immobilized within the nanopore where the first homopolymer is comprised of the same monomer or monomers that comprises the first section of the polymer that produced the first discrete level used to compute the CNR and the second homopolymer is comprised of the same monomer or monomers that comprises the second section of the polymer that produced the second discrete level used to compute the CNR.

16. The nanopore of claim 1, wherein the first level and the second level are correlated to each corresponding composition of the respective sections of the polymer by mapping the nanopore with an immobilized polymer that comprises the same monomer or monomers in the sections of the polymer that produce the first discrete level used to compute the CNR and the second discrete level used to compute the CNR.

17. The nanopore of claim 11, wherein the substituted non-native amino acid comprises an amino acid that reduces the charge compared to the native amino acid.

18. The nanopore of claim 11, wherein the substituted non-native amino acid comprises an amino acid that eliminates the charge of the side chain of the native amino acid.

19. The nanopore of claim 11, wherein the substituted non-native amino acid comprises an amino acid that reduces hydrogen bonding between the amino acid and the polymer compared to the native amino acid and the polymer.

20. The nanopore of claim 11, wherein the substituted non-native amino acid comprises an amino acid smaller in size than the native amino acid.

21. The nanopore of claim 11, wherein the substituted non-native amino acid comprises an amino acid that changes hydrophobic interactions between the amino acid and the DNA.

22. The nanopore of claim 1, wherein at least one of the non-native amino acids that are substituted for native amino acids comprise serine.

23. The nanopore of claim 22, wherein all the non-native amino acids that are substituted for native amino acids comprises serine.

24. The nanopore of claim 23, further comprising a non-native amino acid substitution at position L135 of a wild-type *Staphylococcus aureus* alpha hemolysin polypeptide, wherein the amino acid position of the wild-type *Staphylococcus aureus* alpha hemolysin polypeptide aligns with a corresponding position of the amino acid sequence of the *Staphylococcus aureus* alpha hemolysin polypeptide of SEQ ID NO. 1.

25. The nanopore of claim 24, wherein the non-native amino acid is isoleucine.

26. The nanopore of claim 1, wherein non-native amino acids are further substituted for native amino acids at one or more positions comprising N121, N123, T125, D127, T129, K131, G133, G137 and N139 of a wild-type *Staphylococcus aureus* alpha hemolysin polypeptide, wherein the amino acid positions of the wild-type *Staphylococcus aureus* alpha hemolysin polypeptide align with corresponding positions of the amino acid sequence of the *Staphylococcus aureus* alpha hemolysin polypeptide of SEQ ID NO. 1.

27. The nanopore of claim 2, wherein non-native amino acids are further substituted for native amino acids at one or more positions comprising N121, N123, T125, D127, T129, K131, G133, G137 and N139 of a wild-type *Staphylococcus aureus* alpha hemolysin polypeptide, wherein the amino acid positions of the wild-type *Staphylococcus aureus* alpha hemolysin polypeptide align with corresponding positions of the amino acid sequence of the *Staphylococcus aureus* alpha hemolysin polypeptide of SEQ ID NO. 1.

28. The nanopore of claim 14, wherein the first section does not comprise the same monomer and the second section does not comprise the same monomer.

29. The nanopore of claim 14, wherein the first and the second levels of the residual current are each associated with the measurement of a single monomer.

30. The nanopore of claim 14, wherein the first section and the second section of the polymer comprise different monomers.

* * * * *

SEQUENCE LISTING

```
<160> NUMBER OF SEQ ID NOS: 48

<210> SEQ ID NO 1
<211> LENGTH: 294
<212> TYPE: PRT
<213> ORGANISM: Staphylococcus aureus

<400> SEQUENCE: 1

Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
            20                  25                  30

Asn Gly Met His Lys Lys Val Phe Tyr Ser Phe Ile Asp Asp Lys Asn
        35                  40                  45

His Asn Lys Lys Leu Leu Val Ile Arg Thr Lys Gly Thr Ile Ala Gly
    50                  55                  60

Gln Tyr Arg Val Tyr Ser Glu Glu Gly Ala Asn Lys Ser Gly Leu Ala
65                  70                  75                  80

Trp Pro Ser Ala Phe Lys Val Gln Leu Gln Leu Pro Asp Asn Glu Val
                85                  90                  95

Ala Gln Ile Ser Asp Tyr Tyr Pro Arg Asn Ser Ile Asp Thr Lys Glu
            100                 105                 110

Tyr Met Ser Thr Leu Thr Tyr Gly Phe Asn Gly Asn Val Thr Gly Asp
        115                 120                 125

Asp Thr Gly Lys Ile Gly Gly Leu Ile Gly Ala Asn Val Ser Ile Gly
    130                 135                 140

His Thr Leu Lys Tyr Val Gln Pro Asp Phe Lys Thr Ile Leu Glu Ser
145                 150                 155                 160

Pro Thr Asp Lys Lys Val Gly Trp Lys Val Ile Phe Asn Asn Met Val
                165                 170                 175

Asn Gln Asn Trp Gly Pro Tyr Asp Arg Asp Ser Trp Asn Pro Val Tyr
            180                 185                 190

Gly Asn Gln Leu Phe Met Lys Thr Arg Asn Gly Ser Met Lys Ala Ala
        195                 200                 205
```

Asp Asn Phe Leu Asp Pro Asn Lys Ala Ser Ser Leu Leu Ser Ser Gly
    210                 215                 220

Phe Ser Pro Asp Phe Ala Thr Val Ile Thr Met Asp Arg Lys Ala Ser
225                 230                 235                 240

Lys Gln Gln Thr Asn Ile Asp Val Ile Tyr Glu Arg Val Arg Asp Asp
                245                 250                 255

Tyr Gln Leu His Trp Thr Ser Thr Asn Trp Lys Gly Thr Asn Thr Lys
            260                 265                 270

Asp Lys Trp Thr Asp Arg Ser Ser Glu Arg Tyr Lys Ile Asp Trp Glu
        275                 280                 285

Lys Glu Glu Met Thr Asn
    290

<210> SEQ ID NO 2
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa                         100

<210> SEQ ID NO 3
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
cccccccccc cccccccccc cccccccccc cccccccccc cccccccccc cccccccccc    60
cccccccccc cccccccccc cccccccccc cccccccccc                         100

<210> SEQ ID NO 4
<211> LENGTH: 160
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
aaaaaaaaaa aaaaaaaaaa aaaaaaaaaa aaaaaaaaaa cccccccccc cccccccccc    60
cccccccccc cccccccccc cccccccccc cccccccccc cccccccccc cccccccccc   120
aaaaaaaaaa aaaaaaaaaa aaaaaaaaaa aaaaaaaaaa                         160

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aaaaaaaaaa aaaaaaaaaa aaaaaaaaaa aaaaaaaaaa                          40

<210> SEQ ID NO 6
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cccccccccc cccccccccc cccccccccc cccccccccc cccccccccc cccccccccc      60
cccccccccc cccccccccc                                                   80

<210> SEQ ID NO 7
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
aaaaaaaaaa aaaaaaaaaa aaaaaaaaaa aaaaaaaaaa aaaaaaaaaa cccccccccc      60
cccccccccc cccccccccc cccccccccc cccccccccc cccccccccc cccccccccc     120

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aaaaaaaaaa aaaaaaaaaa aaaaaaaaaa aaaaaaaaaa aaaaaaaaaa                  50

<210> SEQ ID NO 9
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cccccccccc cccccccccc cccccccccc cccccccccc cccccccccc cccccccccc      60
cccccccccc                                                              70

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cccccccccc cccccccccc cccccccccc cccccccccc                             40

<210> SEQ ID NO 11
<211> LENGTH: 115
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
aaaaaaaaaa aaaaaaaaaa aaaaaaaaaa aaaaaaaaaa cccccccccc cccccccccc      60
cccccccccc cccccccccc cccccccccc aaaaaaaaaa aaaaaaaaaa aaaaa           115

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cccccccccc cccccccccc cccccccccc cccccccccc cccccccccc                 50

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaaaaaaaaa ggggaaaaaa aaaaaaaaaa aaaaaaaaaa                            40

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aaaaaaaaaa aaaaaaaaaa aaaaaaaaaa aaaaaagggg                            40

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aaaaaaaaaa aaaaaaaaaa aaaaaaaaaa aaaaaa                                36

<210> SEQ ID NO 16
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
aaaaaaaaaa aaaaaaaaaa aaaaaaaaaa aaaaaaaaaa aaaaaaaaaa cccccccccc      60
cccccccccc cccccccccc cccccccccc cccccccccc                            100

<210> SEQ ID NO 17
<211> LENGTH: 150
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 17
aaaaaaaaaa aaaaaaaaaa aaaaaaaaaa aaaaaaaaaa aaaaaaaaaa cccccccccc        60
cccccccccc cccccccccc cccccccccc cccccccccc cccccccccc cccccccccc       120
cccccccccc cccccccccc cccccccccc                                        150

<210> SEQ ID NO 18
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aaaaaaaaaa aaaaaaaaaa aaaaaaaaaa aaaaaaaaaa gggaaaaaa aaaaaaaaaa         60 aaaaaaaaaa aaaaaaaaaa aaaa                                               84

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19 aagggggaaaa aaaaaaaaaa aaaaaaaaaa aaaaaaaaaa                             40

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20 aaagggaaa aaaaaaaaaa aaaaaaaaaa aaaaaaaaaa                               40

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aaagggggaa aaaaaaaaaa aaaaaaaaaa aaaaaaaaaa                              40

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22 aaaagggga aaaaaaaaaa aaaaaaaaaa aaaaaaaaaa                               40
```

```
<210> SEQ ID NO 23
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aaaaaaaaaa aaaaaaaaaa aaaaaaaaaa aaaaaaaaaa gaaaaaaaaa aaaaaaaaaa        60
aaaaaaaaaa aaaaaaaaaa a                                                  81

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aaaaagaaaa aaaaagaaaa aaaaaaaaaa aaaaaaaaaa                              40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aaaaagaaaa aaaaaataaa aaaaaaaaaa aaaaaaaaaa                              40

<210> SEQ ID NO 26
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aaaaaaaaaa                                                               10

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aaaaaaaaaa aaaaaaaaaa                                                    20

<210> SEQ ID NO 28
<211> LENGTH: 160
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
aaaaaaaaaa aaaaaaaaaa cccccccccc cccccccccc cccccccccc cccccccccc        60
```
cccccccccc cccccccccc cccccccccc cccccccccc cccccccccc      120
cccccccccc cccccccccc aaaaaaaaaa aaaaaaaaaa                  160

<210> SEQ ID NO 29
<211> LENGTH: 170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
aaaaaaaaaa aaaaaaaaaa aaaaaaaaaa aaaaaaaaaa cccccccccc cccccccccc   60
cccccccccc cccccccccc cccccccccc cccccccccc cccccccccc cccccccccc  120
cccccccccc cccccccccc cccccccccc cccccccccc aaaaaaaaaa             170

<210> SEQ ID NO 30
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
aaaaaaaaaa aaaaaaaaaa aaaaaaaaaa aaaaaaaaaa ggggaaaaaa aaaccccccc   60
cccccccccc cccccccccc cccccccccc cccccccccc cccccccccc cccc       114

<210> SEQ ID NO 31
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
cccccccccc cccccccccc cccccccccc cccccccccc tttttttttt tttttttttt   60
tttttttttt tttttttttt cccccccccc cccccccccc cccccccccc cccccccccc  120

<210> SEQ ID NO 32
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
tttttttttt tttttttttt tttttttttt tttttttttt cccccccccc cccccccccc   60
cccccccccc cccccccccc tttttttttt tttttttttt tttttttttt tttttttttt  120

<210> SEQ ID NO 33
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
tttttttttt tttttttttt tttttttttt tttttttttt tttttttttt ggggtttttt   60 ttttttttt ttttttttt ttttttttt ttttttttt tttt    104

<210> SEQ ID NO 34
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
aaaaaaaaaa aaaaaaaaaa cccccccccc cccccccccc cccccccccc cccccccc    60 aaaaaaaaaa aaaaaaaaaa cccccccccc cccccccccc cccccccccc cccccccccc    120
aaaaaaaaaa aaaaaaaaaa    140

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
acacacacac acacacacac acacacacac    30

<210> SEQ ID NO 36
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aaaaaaaaaa aaaaaaaaaa aaaaaaaaaa aaaaaaaaaa caaaaaaaaa aaaaaaaaaa    60
aaaaaaaaaa aaaaaaaaaa a    81

<210> SEQ ID NO 37
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aaaaaaaaaa aaaaaaaaaa aaaaaaaaaa aaaaaaaaaa ccaaaaaaaa aaaaaaaaaa    60
aaaaaaaaaa aaaaaaaaaa aa    82

<210> SEQ ID NO 38
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tttttttttt tttttttttt tttttttttt tttttttttt ctttttttt tttttttttt    60 tttttttttt tttttttttt t    81

```
<210> SEQ ID NO 39
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tttttttttt tttttttttt tttttttttt tttttttttt ccttttttttt tttttttttt      60 tttttttttt tttttttttt tt                                                82

<210> SEQ ID NO 40
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tttttttttt tttttttttt tttttttttt tttttttttt gtttttttttt tttttttttt      60 tttttttttt tttttttttt t                                                 81

<210> SEQ ID NO 41
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cccccccccc cccccccccc cccccccccc cccccccccc acccccccccc cccccccccc      60 cccccccccc cccccccccc c                                                 81

<210> SEQ ID NO 42
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cccccccccc cccccccccc cccccccccc cccccccccc tcccccccccc cccccccccc      60 cccccccccc cccccccccc c                                                 81

<210> SEQ ID NO 43
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cccccccccc cccccccccc cccccccccc cccccccccc aacccccccc cccccccccc       60
cccccccccc cccccccccc cc                                                82

<210> SEQ ID NO 44
<211> LENGTH: 82
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 44
cccccccccc cccccccccc cccccccccc cccccccccc ttcccccccc cccccccccc      60
cccccccccc cccccccccc cc                                               82

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aaaaaaaaaa aaaaaaaaaa aaaaa                                            25

<210> SEQ ID NO 46
<211> LENGTH: 160
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
tttttttttt tttttttttt tttttttttt tttttttttt cccccccccc cccccccccc      60
cccccccccc cccccccccc cccccccccc cccccccccc cccccccccc cccccccccc     120
tttttttttt tttttttttt tttttttttt tttttttttt                           160

<210> SEQ ID NO 47
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
cccccccccc cccccccccc cccccccccc cccccccccc cccccccccc cccccccccc      60
cccccccccc cccccccccc aaaaaaaaaa aaaaaaaaaa aaaaaaaaaa aaaaaaaaaa     120
cccccccccc cccccccccc cccccccccc cccccccccc cccccccccc cccccccccc     180
cccccccccc cccccccccc                                                 200

<210> SEQ ID NO 48
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aaaaaaaaaa aaaaaaaaaa aaaaaaaaaa aaaaaaaaaa ggggcccccc cccccccccc      60
cccccccccc cccccccccc cccc                                             84
```